(12) United States Patent
O'Brien et al.

(10) Patent No.: US 7,935,531 B2
(45) Date of Patent: May 3, 2011

(54) METHODS FOR THE EARLY DIAGNOSIS OF OVARIAN CANCER

(75) Inventors: Timothy J. O'Brien, Little Rock, AR (US); Martin J. Cannon, Little Rock, AR (US); Alessandro Santin, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 130 days.

(21) Appl. No.: 10/135,795

(22) Filed: Apr. 30, 2002

(65) Prior Publication Data

US 2003/0077618 A1 Apr. 24, 2003

Related U.S. Application Data

(60) Continuation-in-part of application No. 10/102,283, filed on Mar. 20, 2002, now Pat. No. 6,875,609, which is a continuation-in-part of application No. 09/919,048, filed on Jul. 30, 2001, now Pat. No. 6,787,354, which is a continuation-in-part of application No. 09/861,966, filed on May 21, 2001, now Pat. No. 6,518,028, which is a division of application No. 09/510,738, filed on Feb. 22, 2000, now Pat. No. 6,268,165.

(51) Int. Cl.
*C12N 15/00* (2006.01)
*A01N 63/00* (2006.01)
(52) U.S. Cl. .................................. 435/455; 424/93.1
(58) Field of Classification Search ............... 536/23.1; 435/320.1; 424/93.1, 184.1; 530/300, 350
See application file for complete search history.

(56) References Cited

U.S. PATENT DOCUMENTS 5,981,830 A * 11/1999 Wu et al. ................. 800/18
6,232,456 B1 * 5/2001 Cohen et al. ............. 536/23.2

FOREIGN PATENT DOCUMENTS

WO WO 9854307 A1 * 12/1998

OTHER PUBLICATIONS

Resitfo et al. (2000) The Promise of nucleic acid vaccines. Gene Therapy. 7:89-92.*
Paglia et al. (1996) Murine Dendritic Cells Loaded in vitro with soluble protein prime cytotoxic T lymphocytes against Tumor antigen in vivo. J. Exp. Med. 183:317-322.*
Jain RK (1994) Barrier to Drug Delivery in Solid Tumors. Sci Am. 1291:58-65.*
Gura T. 1997) Systems for identifying new drugs are often faulty. Science. 278:1041-1042.*
Sequence alignment from Us Patent 6,232,456; issued May 2001.*
Sequence alignement with International Patent Application No. WO 98/54307; published Dec. 3, 1998.*
McCluskie et al. (1999) Route and Method of Delivery of DNA Vaccine Influence Immune Responses in Mice and Non-Human Primates. Molecular Medicine. 5:287-300.*
Verma et al., Gene therapy-promises, problems and prospects. (1997) Nature. 389:239-242.*
Orkin et al., Report and Reccommendations of the Panel to assess the NIH invextment in Research on Gene Therapy (1998) 1-41.*
Marshall., Gene Therapy's Growing Pains (1995) Science 269:1050-1055.*
Markiewicz et al. (2004) Progress in the development of immunotherapy of cancer using Ex-vivo-Generated Dendritic Cells Expressing Multiple Tumor Atnigen Epitopes. Cancer Investigation. 22:417-434.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Ginestier et al. (2002) Am. J. of Pathology 161:1223-1233.*
Lucentini (2004) "Gene Association Studies are Typically Wrong", The Scientist, 18(24):20.*
Li et al. (2005) Biochem. et Biophys. Acta 1681:157-165.*
Foldvari et al, (Curr Drug Delivery, 3: 17-28, 2006.*
Hurk et al (Immunological Reviews, 199: 113-125, 2004.*
McCarthy et al, (British Journal of Haematology, 123: 770-781, 2003.*
Vasioukhin (Cell Cycle, 3(11): 1394-1397, 2004.*
Lowe et al, (Journal of Cellular Biochemistry, 98: 235-242, 2006.*
Bocchia et al, (Haematologica, 85(11): 1172-1206, 2000.*
Crammer et al, (Cancer Immunol Immunother, 53: 275-306, 2004.*
Yang et al, (Int. J. Cancer, 83: 532-540, 1999).*
Jardetzky et al (Nature, 353(6342): 326-329, 1991).*
Tanimoto et al, (Cancer Res, 57: 2884-2887, 1997).*
Winchester et al, (Current Opinion in Rheumatology, 11: 251-256, 1999).*
Krummel (Cell, 129: 653-655, 2007).*
Disis et al (Lancet, 373: 673-683, 2009).*

* cited by examiner

*Primary Examiner* — Anne-Marie Falk
*Assistant Examiner* — Magdalene Sgagias
(74) *Attorney, Agent, or Firm* — Benjamin Aaron Adler

(57) ABSTRACT

The disclosed nucleic acid primer sets, used in combination with quantitative amplification (PCR) of tissue cDNA, can indicate the presence of specific proteases in a tissue sample. Specifically, the present invention relates to expression of hepsin protease. The detected proteases are themselves specifically over-expressed in certain cancers, and the presence of their genetic precursors may serve for early detection of associated ovarian and other malignancies, and for the design of interactive therapies for cancer treatment.

1 Claim, 24 Drawing Sheets

TADG12

1.  ↓  .15
. .  . 
VVTAAHCVYDLYLPK

16                .30
 .                 .
SWTIQVGLVSLLDNP     ↓ indicates the site of insert in TADG12

31                .45          H & D are the conserved regions of
 .                 .           Serine protease.
APSHLVEKIVYHSKY 46        57
 .         .
KPKRLGNDIALL

```
  1  6    10                         53    57
  _ _ H CVY D LYL _ _ _ _ _ _ _ _ _  D _ _ _ .
      *      ⬆                       *
     site of 133 bp insert in TADG12
```

Fig. 15

SEQUENCE LISTING

```
<160> NUMBER OF SEQ ID NOS: 191

<210> SEQ ID NO 1
<211> LENGTH: 23
<212> TYPE: DNA
<213> ORGANISM: Artificial sequence
<220> FEATURE:
<221> NAME/KEY: primer_bind
<222> LOCATION: 6, 9, 12, 15, 18
<223> OTHER INFORMATION: sense oligonucleotide primer for amplifying
      serine proteases, n = Inosine

<400> SEQUENCE: 1
tgggtngtna cngcngcnca ytg                                              23

<210> SEQ ID NO 2
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 15, 18
<223> OTHER INFORMATION: antisense oligonucleotide primer for amplifying
      serine proteases, n = Inosine

<400> SEQUENCE: 2
arnarngcna tntcnttncc                                                  20

<210> SEQ ID NO 3
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 18
<223> OTHER INFORMATION: antisense oligonucleotide primer for amplifying
      serine proteases, n = Inosine

<400> SEQUENCE: 3
arnggnccnc cnswrtcncc                                                  20
```

```
<210> SEQ ID NO 4
<211> LENGTH: 24
<212> TYPE: DNA
<213> ORGANISM: Artificial sequence
<220> FEATURE:
<221> NAME/KEY: primer_bind
<222> LOCATION: 6, 15, 18
<223> OTHER INFORMATION: sense oligonucleotide primer for amplifying
      cysteine proteases, n = Inosine

<400> SEQUENCE: 4
carggncart gyggnwsntg ytgg                                          24

<210> SEQ ID NO 5
<211> LENGTH: 20
<212> TYPE: DNA
<213> ORGANISM: Artificial sequence
<220> FEATURE:
<221> NAME/KEY: primer_bind
<222> LOCATION: 3, 6, 15
<223> OTHER INFORMATION: antisense oligonucleotide primer for amplifying
      cysteine proteases, n = Inosine

<400> SEQUENCE: 5
tanccnccrt trcanccytc                                               20

<210> SEQ ID NO 6
<211> LENGTH: 20
<212> TYPE: DNA
<213> ORGANISM: Artificial sequence
<220> FEATURE:
<221> NAME/KEY: primer_bind
<222> LOCATION: 3, 6, 12, 15, 18
<223> OTHER INFORMATION: sense oligonucleotide primer for amplifying
      metallo-proteases, n = Inosine

<400> SEQUENCE: 6
ccnmgntgyg gnrwnccnga                                               20

<210> SEQ ID NO 7
<211> LENGTH: 17
<212> TYPE: DNA
<213> ORGANISM: Artificial sequence
<220> FEATURE:
<221> NAME/KEY: primer_bind
<222> LOCATION: 6, 9, 11
<223> OTHER INFORMATION: antisense oligonucleotide primer for amplifying
      metallo-proteases, n = Inosine

<400> SEQUENCE: 7
ttrtgnccna nytcrtg                                                  17

<210> SEQ ID NO 8
<211> LENGTH: 20
<212> TYPE: DNA
<213> ORGANISM: Artificial sequence
<220> FEATURE:
<223> OTHER INFORMATION: sense oligonucleotide primer specific for
      hepsin

<400> SEQUENCE: 8
tgtcccgatg gcgagtgttt                                               20

<210> SEQ ID NO 9
<211> LENGTH: 20
<212> TYPE: DNA
<213> ORGANISM: Artificial sequence
<220> FEATURE:
<223> OTHER INFORMATION: antisense oligonucleotide primer specific for
      hepsin
```

```
<400> SEQUENCE: 9
cctgttggcc atagtactgc                                              20

<210> SEQ ID NO 10
<211> LENGTH: 20
<212> TYPE: DNA
<213> ORGANISM: Artificial sequence
<220> FEATURE:
<223> OTHER INFORMATION: sense oligonucleotide primer specific for SCCE

<400> SEQUENCE: 10
agatgaatga gtacaccgtg                                              20

<210> SEQ ID NO 11
<211> LENGTH: 20
<212> TYPE: DNA
<213> ORGANISM: Artificial sequence
<220> FEATURE:
<223> OTHER INFORMATION: antisense oligonucleotide primer specific for
      SCCE

<400> SEQUENCE: 11
ccagtaagtc cttgtaaacc                                              20

<210> SEQ ID NO 12
<211> LENGTH: 20
<212> TYPE: DNA
<213> ORGANISM: Artificial sequence
<220> FEATURE:
<223> OTHER INFORMATION: sense oligonucleotide primer specific for CompB

<400> SEQUENCE: 12
aagggacacg agagctgtat                                              20

<210> SEQ ID NO 13
<211> LENGTH: 20
<212> TYPE: DNA
<213> ORGANISM: Artificial sequence
<220> FEATURE:
<223> OTHER INFORMATION: antisense oligonucleotide primer specific for
      CompB

<400> SEQUENCE: 13
aagtggtagt tggaggaagc                                              20

<210> SEQ ID NO 14
<211> LENGTH: 20
<212> TYPE: DNA
<213> ORGANISM: Artificial sequence
<220> FEATURE:
<223> OTHER INFORMATION: sense oligonucleotide primer specific for
      Cath-L

<400> SEQUENCE: 14
attggagaga gaaaggctac                                              20

<210> SEQ ID NO 15
<211> LENGTH: 20
<212> TYPE: DNA
<213> ORGANISM: Artificial sequence
<220> FEATURE:
<223> OTHER INFORMATION: antisense oligonucleotide primer specific for
      Cath-L

<400> SEQUENCE: 15
cttgggattg tacttacagg                                              20
```

<210> SEQ ID NO 16
<211> LENGTH: 20
<212> TYPE: DNA
<213> ORGANISM: Artificial sequence
<220> FEATURE:
<223> OTHER INFORMATION: sense oligonucleotide primer specific for
      PUMP-1

<400> SEQUENCE: 16
cttccaaagt ggtcacctac                                          20

<210> SEQ ID NO 17
<211> LENGTH: 20
<212> TYPE: DNA
<213> ORGANISM: Artificial sequence
<220> FEATURE:
<223> OTHER INFORMATION: antisense oligonucleotide primer specific for
      PUMP-1

<400> SEQUENCE: 17
ctagactgct accatccgtc                                          20

<210> SEQ ID NO 18
<211> LENGTH: 17
<212> TYPE: DNA
<213> ORGANISM: Artificial sequence
<220> FEATURE:
<223> OTHER INFORMATION: sense oligonucleotide primer specific for
      (-tubulin

<400> SEQUENCE: 18
tgcattgaca acgaggc                                             17

<210> SEQ ID NO 19
<211> LENGTH: 17
<212> TYPE: DNA
<213> ORGANISM: Artificial sequence
<220> FEATURE:
<223> OTHER INFORMATION: antisense oligonucleotide primer specific for
      (-tubulin

<400> SEQUENCE: 19
ctgtcttgac attgttg                                             17

<210> SEQ ID NO 20
<211> LENGTH: 20
<212> TYPE: DNA
<213> ORGANISM: Artificial sequence
<220> FEATURE:
<223> OTHER INFORMATION: sense oligonucleotide primer specific for
      Protease M

<400> SEQUENCE: 20
ctgtgatcca ccctgactat                                          20

<210> SEQ ID NO 21
<211> LENGTH: 20
<212> TYPE: DNA
<213> ORGANISM: Artificial sequence
<220> FEATURE:
<223> OTHER INFORMATION: antisense oligonucleotide primer specific for
      Protease M

<400> SEQUENCE: 21
caggtggatg tatgcacact                                          20

```
<210> SEQ ID NO 22
<211> LENGTH: 20
<212> TYPE: DNA
<213> ORGANISM: Artificial sequence
<220> FEATURE:
<223> OTHER INFORMATION: sense oligonucleotide primer specific for
      TADG-12

<400> SEQUENCE: 22
gcgcactgtg tttatgagat                                                 20

<210> SEQ ID NO 23
<211> LENGTH: 20
<212> TYPE: DNA
<213> ORGANISM: Artificial sequence
<220> FEATURE:
<223> OTHER INFORMATION: antisense oligonucleotide primer specific for
      TADG-12

<400> SEQUENCE: 23
ctctttggct tgtacttgct                                                 20

<210> SEQ ID NO 24
<211> LENGTH: 20
<212> TYPE: DNA
<213> ORGANISM: Artificial sequence
<220> FEATURE:
<223> OTHER INFORMATION: sense oligonucleotide primer specific for
      TADG-13

<400> SEQUENCE: 24
tgagggacat cattatgcac                                                 20

<210> SEQ ID NO 25
<211> LENGTH: 20
<212> TYPE: DNA
<213> ORGANISM: Artificial sequence
<220> FEATURE:
<223> OTHER INFORMATION: antisense oligonucleotide primer specific for
      TADG-13

<400> SEQUENCE: 25 caagtttttcc ccataattgg                                                20

<210> SEQ ID NO 26
<211> LENGTH: 20
<212> TYPE: DNA
<213> ORGANISM: Artificial sequence
<220> FEATURE:
<223> OTHER INFORMATION: sense oligonucleotide primer specific for
      TADG-14

<400> SEQUENCE: 26
acagtacgcc tgggagacca                                                 20

<210> SEQ ID NO 27
<211> LENGTH: 20
<212> TYPE: DNA
<213> ORGANISM: Artificial sequence
<220> FEATURE:
<223> OTHER INFORMATION: antisense oligonucleotide primer specific for
      TADG-14

<400> SEQUENCE: 27
ctgagacggt gcaattctgg                                                 20
```

```
<210> SEQ ID NO 28
<211> LENGTH: 9
<212> TYPE: PRT
<213> ORGANISM: Homo sapiens
<220> FEATURE:
<223> OTHER INFORMATION: Residues 170-178 of the hepsin protein

<400> SEQUENCE: 28

Ser Leu Gly Arg Trp Pro Trp Gln Val
                5

<210> SEQ ID NO 29
<211> LENGTH: 9
<212> TYPE: PRT
<213> ORGANISM: Homo sapiens
<220> FEATURE:
<223> OTHER INFORMATION: Residues 191-199 of the hepsin protein

<400> SEQUENCE: 29

Ser Leu Leu Ser Gly Asp Trp Val Leu
                5

<210> SEQ ID NO 30
<211> LENGTH: 9
<212> TYPE: PRT
<213> ORGANISM: Homo sapiens
<220> FEATURE:
<223> OTHER INFORMATION: Residues 229-237 of the hepsin protein

<400> SEQUENCE: 30

Gly Leu Gln Leu Gly Val Gln Ala Val
                5

<210> SEQ ID NO 31
<211> LENGTH: 9
<212> TYPE: PRT
<213> ORGANISM: Homo sapiens
<220> FEATURE:
<223> OTHER INFORMATION: Residues 392-400 of the hepsin protein

<400> SEQUENCE: 31

Lys Val Ser Asp Phe Arg Glu Trp Ile
                5

<210> SEQ ID NO 32
<211> LENGTH: 9
<212> TYPE: PRT
<213> ORGANISM: Homo sapiens
<220> FEATURE:
<223> OTHER INFORMATION: Residues 308-316 of the hepsin protein

<400> SEQUENCE: 32

Val Leu Gln Glu Ala Arg Val Pro Ile
                5

<210> SEQ ID NO 33
<211> LENGTH: 9
<212> TYPE: PRT
<213> ORGANISM: Homo sapiens
<220> FEATURE:
<223> OTHER INFORMATION: Residues 130-138 of the hepsin protein

<400> SEQUENCE: 33

Arg Leu Leu Glu Val Ile Ser Val Cys
                5
```

```
<210> SEQ ID NO 34
<211> LENGTH: 9
<212> TYPE: PRT
<213> ORGANISM: Homo sapiens
<220> FEATURE:
<223> OTHER INFORMATION: Residues 98-106 of the hepsin protein

<400> SEQUENCE: 34

Ala Leu Thr His Ser Glu Leu Asp Val
                5

<210> SEQ ID NO 35
<211> LENGTH: 9
<212> TYPE: PRT
<213> ORGANISM: Homo sapiens
<220> FEATURE:
<223> OTHER INFORMATION: Residues 211-219 of the hepsin protein

<400> SEQUENCE: 35

Val Leu Ser Arg Trp Arg Val Phe Ala
                5

<210> SEQ ID NO 36
<211> LENGTH: 9
<212> TYPE: PRT
<213> ORGANISM: Homo sapiens
<220> FEATURE:
<223> OTHER INFORMATION: Residues 26-34 of the hepsin protein

<400> SEQUENCE: 36

Leu Leu Leu Leu Thr Ala Ile Gly Ala
                5

<210> SEQ ID NO 37
<211> LENGTH: 9
<212> TYPE: PRT
<213> ORGANISM: Homo sapiens
<220> FEATURE:
<223> OTHER INFORMATION: Residues 284-292 of the hepsin protein

<400> SEQUENCE: 37

Ala Leu Val Asp Gly Lys Ile Cys Thr
                5

<210> SEQ ID NO 38
<211> LENGTH: 9
<212> TYPE: PRT
<213> ORGANISM: Homo sapiens
<220> FEATURE:
<223> OTHER INFORMATION: Residues 145-153 of the hepsin protein

<400> SEQUENCE: 38

Phe Leu Ala Ala Ile Cys Gln Asp Cys
                5

<210> SEQ ID NO 39
<211> LENGTH: 9
<212> TYPE: PRT
<213> ORGANISM: Homo sapiens
<220> FEATURE:
<223> OTHER INFORMATION: Residues 192-200 of the hepsin protein

<400> SEQUENCE: 39

Leu Leu Ser Gly Asp Trp Val Leu Thr
                5
```

```
<210> SEQ ID NO 40
<211> LENGTH: 9
<212> TYPE: PRT
<213> ORGANISM: Homo sapiens
<220> FEATURE:
<223> OTHER INFORMATION: Residues 20-28 of the hepsin protein

<400> SEQUENCE: 40

Ala Leu Thr Ala Gly Thr Leu Leu Leu
                5

<210> SEQ ID NO 41
<211> LENGTH: 9
<212> TYPE: PRT
<213> ORGANISM: Homo sapiens
<220> FEATURE:
<223> OTHER INFORMATION: Residues 259-267 of the hepsin protein

<400> SEQUENCE: 41

Ala Leu Val His Leu Ser Ser Pro Leu
                5

<210> SEQ ID NO 42
<211> LENGTH: 9
<212> TYPE: PRT
<213> ORGANISM: Homo sapiens
<220> FEATURE:
<223> OTHER INFORMATION: Residues 277-285 of the hepsin protein

<400> SEQUENCE: 42

Cys Leu Pro Ala Ala Gly Gln Ala Leu
                5

<210> SEQ ID NO 43
<211> LENGTH: 9
<212> TYPE: PRT
<213> ORGANISM: Homo sapiens
<220> FEATURE:
<223> OTHER INFORMATION: Residues 230-238 of the hepsin protein

<400> SEQUENCE: 43

Leu Gln Leu Gly Val Gln Ala Val Val
                5

<210> SEQ ID NO 44
<211> LENGTH: 9
<212> TYPE: PRT
<213> ORGANISM: Homo sapiens
<220> FEATURE:
<223> OTHER INFORMATION: Residues 268-276 of the hepsin protein

<400> SEQUENCE: 44

Pro Leu Thr Glu Tyr Ile Gln Pro Val
                5

<210> SEQ ID NO 45
<211> LENGTH: 9
<212> TYPE: PRT
<213> ORGANISM: Homo sapiens
<220> FEATURE:
<223> OTHER INFORMATION: Residues 31-39 of the hepsin protein

<400> SEQUENCE: 45

Ala Ile Gly Ala Ala Ser Trp Ala Ile
                5
```

```
<210> SEQ ID NO 46
<211> LENGTH: 9
<212> TYPE: PRT
<213> ORGANISM: Homo sapiens
<220> FEATURE:
<223> OTHER INFORMATION: Residues 285-293 of the hepsin protein

<400> SEQUENCE: 46

Leu Val Asp Gly Lys Ile Cys Thr Val
                5

<210> SEQ ID NO 47
<211> LENGTH: 9
<212> TYPE: PRT
<213> ORGANISM: Homo sapiens
<220> FEATURE:
<223> OTHER INFORMATION: Residues 27-35 of the hepsin protein

<400> SEQUENCE: 47

Leu Leu Leu Thr Ala Ile Gly Ala Ala
                5

<210> SEQ ID NO 48
<211> LENGTH: 9
<212> TYPE: PRT
<213> ORGANISM: Homo sapiens
<220> FEATURE:
<223> OTHER INFORMATION: Residues 191-199 of the hepsin protein

<400> SEQUENCE: 48

Ser Leu Leu Ser Gly Asp Trp Val Leu
                5

<210> SEQ ID NO 49
<211> LENGTH: 9
<212> TYPE: PRT
<213> ORGANISM: Homo sapiens
<220> FEATURE:
<223> OTHER INFORMATION: Residues 163-171 of the hepsin protein

<400> SEQUENCE: 49

Ile Val Gly Gly Arg Asp Thr Ser Leu
                5

<210> SEQ ID NO 50
<211> LENGTH: 9
<212> TYPE: PRT
<213> ORGANISM: Homo sapiens
<220> FEATURE:
<223> OTHER INFORMATION: Residues 392-400 of the hepsin protein

<400> SEQUENCE: 50

Lys Val Ser Asp Phe Arg Glu Trp Ile
                5

<210> SEQ ID NO 51
<211> LENGTH: 9
<212> TYPE: PRT
<213> ORGANISM: Homo sapiens
<220> FEATURE:
<223> OTHER INFORMATION: Residues 64-72 of the hepsin protein

<400> SEQUENCE: 51

Met Val Phe Asp Lys Thr Glu Gly Thr
                5
```

```
<210> SEQ ID NO 52
<211> LENGTH: 9
<212> TYPE: PRT
<213> ORGANISM: Homo sapiens
<220> FEATURE:
<223> OTHER INFORMATION: Residues 236-244 of the hepsin protein

<400> SEQUENCE: 52

Ala Val Val Tyr His Gly Gly Tyr Leu
                5

<210> SEQ ID NO 53
<211> LENGTH: 9
<212> TYPE: PRT
<213> ORGANISM: Homo sapiens
<220> FEATURE:
<223> OTHER INFORMATION: Residues 55-63 of the hepsin protein

<400> SEQUENCE: 53

Gln Val Ser Ser Ala Asp Ala Arg Leu
                5

<210> SEQ ID NO 54
<211> LENGTH: 9
<212> TYPE: PRT
<213> ORGANISM: Homo sapiens
<220> FEATURE:
<223> OTHER INFORMATION: Residues 130-138 of the hepsin protein

<400> SEQUENCE: 54

Arg Leu Leu Glu Val Ile Ser Val Cys
                5

<210> SEQ ID NO 55
<211> LENGTH: 9
<212> TYPE: PRT
<213> ORGANISM: Homo sapiens
<220> FEATURE:
<223> OTHER INFORMATION: Residues 230-238 of the hepsin protein

<400> SEQUENCE: 55

Leu Gln Leu Gly Val Gln Ala Val Val
                5

<210> SEQ ID NO 56
<211> LENGTH: 9
<212> TYPE: PRT
<213> ORGANISM: Homo sapiens
<220> FEATURE:
<223> OTHER INFORMATION: Residues 20-28 of the hepsin protein

<400> SEQUENCE: 56

Ala Leu Thr Ala Gly Thr Leu Leu Leu
                5

<210> SEQ ID NO 57
<211> LENGTH: 9
<212> TYPE: PRT
<213> ORGANISM: Homo sapiens
<220> FEATURE:
<223> OTHER INFORMATION: Residues 259-267 of the hepsin protein

<400> SEQUENCE: 57

Ala Leu Val His Leu Ser Ser Pro Leu
                5
```

```
<210> SEQ ID NO 58
<211> LENGTH: 9
<212> TYPE: PRT
<213> ORGANISM: Homo sapiens
<220> FEATURE:
<223> OTHER INFORMATION: Residues 277-285 of the hepsin protein

<400> SEQUENCE: 58

Cys Leu Pro Ala Ala Gly Gln Ala Leu
                5

<210> SEQ ID NO 59
<211> LENGTH: 9
<212> TYPE: PRT
<213> ORGANISM: Homo sapiens
<220> FEATURE:
<223> OTHER INFORMATION: Residues 17-25 of the hepsin protein

<400> SEQUENCE: 59

Lys Val Ala Ala Leu Thr Ala Gly Thr
                5

<210> SEQ ID NO 60
<211> LENGTH: 9
<212> TYPE: PRT
<213> ORGANISM: Homo sapiens
<220> FEATURE:
<223> OTHER INFORMATION: Residues 285-293 of the hepsin protein

<400> SEQUENCE: 60

Leu Val Asp Gly Lys Ile Cys Thr Val
                5

<210> SEQ ID NO 61
<211> LENGTH: 9
<212> TYPE: PRT
<213> ORGANISM: Homo sapiens
<220> FEATURE:
<223> OTHER INFORMATION: Residues 308-316 of the hepsin protein

<400> SEQUENCE: 61

Val Leu Gln Glu Ala Arg Val Pro Ile
                5

<210> SEQ ID NO 62
<211> LENGTH: 9
<212> TYPE: PRT
<213> ORGANISM: Homo sapiens
<220> FEATURE:
<223> OTHER INFORMATION: Residues 27-35 of the hepsin protein

<400> SEQUENCE: 62

Leu Leu Leu Thr Ala Ile Gly Ala Ala
                5

<210> SEQ ID NO 63
<211> LENGTH: 9
<212> TYPE: PRT
<213> ORGANISM: Homo sapiens
<220> FEATURE:
<223> OTHER INFORMATION: Residues 229-237 of the hepsin protein

<400> SEQUENCE: 63

Gly Leu Gln Leu Gly Val Gln Ala Val
                5
```

```
<210> SEQ ID NO 64
<211> LENGTH: 9
<212> TYPE: PRT
<213> ORGANISM: Homo sapiens
<220> FEATURE:
<223> OTHER INFORMATION: Residues 313-321 of the hepsin protein

<400> SEQUENCE: 64

Arg Val Pro Ile Ile Ser Asn Asp Val
                5

<210> SEQ ID NO 65
<211> LENGTH: 9
<212> TYPE: PRT
<213> ORGANISM: Homo sapiens
<220> FEATURE:
<223> OTHER INFORMATION: Residues 88-96 of the hepsin protein

<400> SEQUENCE: 65

Leu Ser Cys Glu Glu Met Gly Phe Leu
                5

<210> SEQ ID NO 66
<211> LENGTH: 9
<212> TYPE: PRT
<213> ORGANISM: Homo sapiens
<220> FEATURE:
<223> OTHER INFORMATION: Residues 192-200 of the hepsin protein

<400> SEQUENCE: 66

Leu Leu Ser Gly Asp Trp Val Leu Thr
                5

<210> SEQ ID NO 67
<211> LENGTH: 9
<212> TYPE: PRT
<213> ORGANISM: Homo sapiens
<220> FEATURE:
<223> OTHER INFORMATION: Residues 284-292 of the hepsin protein

<400> SEQUENCE: 67

Ala Leu Val Asp Gly Lys Ile Cys Thr
                5

<210> SEQ ID NO 68
<211> LENGTH: 9
<212> TYPE: PRT
<213> ORGANISM: Homo sapiens
<220> FEATURE:
<223> OTHER INFORMATION: Residues 89-97 of the hepsin protein

<400> SEQUENCE: 68

Ser Cys Glu Glu Met Gly Phe Leu Arg
                5

<210> SEQ ID NO 69
<211> LENGTH: 9
<212> TYPE: PRT
<213> ORGANISM: Homo sapiens
<220> FEATURE:
<223> OTHER INFORMATION: Residues 58-66 of the hepsin protein

<400> SEQUENCE: 69

Ser Ala Asp Ala Arg Leu Met Val Phe
                5
```

```
<210> SEQ ID NO 70
<211> LENGTH: 9
<212> TYPE: PRT
<213> ORGANISM: Homo sapiens
<220> FEATURE:
<223> OTHER INFORMATION: Residues 393-401 of the hepsin protein

<400> SEQUENCE: 70

Val Ser Asp Phe Arg Glu Trp Ile Phe
                5

<210> SEQ ID NO 71
<211> LENGTH: 9
<212> TYPE: PRT
<213> ORGANISM: Homo sapiens
<220> FEATURE:
<223> OTHER INFORMATION: Residues 407-415 of the hepsin protein

<400> SEQUENCE: 71

His Ser Glu Ala Ser Gly Met Val Thr
                5

<210> SEQ ID NO 72
<211> LENGTH: 9
<212> TYPE: PRT
<213> ORGANISM: Homo sapiens
<220> FEATURE:
<223> OTHER INFORMATION: Residues 137-145 of the hepsin protein

<400> SEQUENCE: 72

Val Cys Asp Cys Pro Arg Gly Arg Phe
                5

<210> SEQ ID NO 73
<211> LENGTH: 9
<212> TYPE: PRT
<213> ORGANISM: Homo sapiens
<220> FEATURE:
<223> OTHER INFORMATION: Residues 269-277 of the hepsin protein

<400> SEQUENCE: 73

Leu Thr Glu Tyr Ile Gln Pro Val Cys
                5

<210> SEQ ID NO 74
<211> LENGTH: 9
<212> TYPE: PRT
<213> ORGANISM: Homo sapiens
<220> FEATURE:
<223> OTHER INFORMATION: Residues 47-55 of the hepsin protein

<400> SEQUENCE: 74

Asp Gln Glu Pro Leu Tyr Pro Val Gln
                5

<210> SEQ ID NO 75
<211> LENGTH: 9
<212> TYPE: PRT
<213> ORGANISM: Homo sapiens
<220> FEATURE:
<223> OTHER INFORMATION: Residues 119-127 of the hepsin protein

<400> SEQUENCE: 75

Cys Val Asp Glu Gly Arg Leu Pro His
                5
```

```
<210> SEQ ID NO 76
<211> LENGTH: 9
<212> TYPE: PRT
<213> ORGANISM: Homo sapiens
<220> FEATURE:
<223> OTHER INFORMATION: Residues 68-76 of the hepsin protein

<400> SEQUENCE: 76

Lys Thr Glu Gly Thr Trp Arg Leu Leu
                5

<210> SEQ ID NO 77
<211> LENGTH: 9
<212> TYPE: PRT
<213> ORGANISM: Homo sapiens
<220> FEATURE:
<223> OTHER INFORMATION: Residues 101-109 of the hepsin protein

<400> SEQUENCE: 77

His Ser Glu Leu Asp Val Arg Thr Ala
                5

<210> SEQ ID NO 78
<211> LENGTH: 9
<212> TYPE: PRT
<213> ORGANISM: Homo sapiens
<220> FEATURE:
<223> OTHER INFORMATION: Residues 250-258 of the hepsin protein

<400> SEQUENCE: 78

Asn Ser Glu Glu Asn Ser Asn Asp Ile
                5

<210> SEQ ID NO 79
<211> LENGTH: 9
<212> TYPE: PRT
<213> ORGANISM: Homo sapiens
<220> FEATURE:
<223> OTHER INFORMATION: Residues 293-301 of the hepsin protein

<400> SEQUENCE: 79

Val Thr Gly Trp Gly Asn Thr Gln Tyr
                5

<210> SEQ ID NO 80
<211> LENGTH: 9
<212> TYPE: PRT
<213> ORGANISM: Homo sapiens
<220> FEATURE:
<223> OTHER INFORMATION: Residues 231-239 of the hepsin protein

<400> SEQUENCE: 80

Gln Leu Gly Val Gln Ala Val Val Tyr
                5

<210> SEQ ID NO 81
<211> LENGTH: 9
<212> TYPE: PRT
<213> ORGANISM: Homo sapiens
<220> FEATURE:
<223> OTHER INFORMATION: Residues 103-111 of the hepsin protein

<400> SEQUENCE: 81

Glu Leu Asp Val Arg Thr Ala Gly Ala
                5
```

```
<210> SEQ ID NO 82
<211> LENGTH: 9
<212> TYPE: PRT
<213> ORGANISM: Homo sapiens
<220> FEATURE:
<223> OTHER INFORMATION: Residues 378-386 of the hepsin protein

<400> SEQUENCE: 82

Gly Thr Gly Cys Ala Leu Ala Gln Lys
                5

<210> SEQ ID NO 83
<211> LENGTH: 9
<212> TYPE: PRT
<213> ORGANISM: Homo sapiens
<220> FEATURE:
<223> OTHER INFORMATION: Residues 358-366 of the hepsin protein

<400> SEQUENCE: 83

Val Cys Glu Asp Ser Ile Ser Arg Thr
                5

<210> SEQ ID NO 84
<211> LENGTH: 9
<212> TYPE: PRT
<213> ORGANISM: Homo sapiens
<220> FEATURE:
<223> OTHER INFORMATION: Residues 264-272 of the hepsin protein

<400> SEQUENCE: 84

Ser Ser Pro Leu Pro Leu Thr Glu Tyr
                5

<210> SEQ ID NO 85
<211> LENGTH: 9
<212> TYPE: PRT
<213> ORGANISM: Homo sapiens
<220> FEATURE:
<223> OTHER INFORMATION: Residues 87-95 of the hepsin protein

<400> SEQUENCE: 85

Gly Leu Ser Cys Glu Glu Met Gly Phe
                5

<210> SEQ ID NO 86
<211> LENGTH: 9
<212> TYPE: PRT
<213> ORGANISM: Homo sapiens
<220> FEATURE:
<223> OTHER INFORMATION: Residues 272-280 of the hepsin protein

<400> SEQUENCE: 86

Tyr Ile Gln Pro Val Cys Leu Pro Ala
                5

<210> SEQ ID NO 87
<211> LENGTH: 9
<212> TYPE: PRT
<213> ORGANISM: Homo sapiens
<220> FEATURE:
<223> OTHER INFORMATION: Residues 345-353 of the hepsin protein

<400> SEQUENCE: 87

Gly Ile Asp Ala Cys Gln Gly Asp Ser
                5
```

```
<210> SEQ ID NO 88
<211> LENGTH: 9
<212> TYPE: PRT
<213> ORGANISM: Homo sapiens
<220> FEATURE:
<223> OTHER INFORMATION: Residues 301-309 of the hepsin protein

<400> SEQUENCE: 88

Tyr Tyr Gly Gln Gln Ala Gly Val Leu
                5

<210> SEQ ID NO 89
<211> LENGTH: 9
<212> TYPE: PRT
<213> ORGANISM: Homo sapiens
<220> FEATURE:
<223> OTHER INFORMATION: Residues 238-246 of the hepsin protein

<400> SEQUENCE: 89

Val Tyr His Gly Gly Tyr Leu Pro Phe
                5

<210> SEQ ID NO 90
<211> LENGTH: 9
<212> TYPE: PRT
<213> ORGANISM: Homo sapiens
<220> FEATURE:
<223> OTHER INFORMATION: Residues 204-212 of the hepsin protein

<400> SEQUENCE: 90

Cys Phe Pro Glu Arg Asn Arg Val Leu
                5

<210> SEQ ID NO 91
<211> LENGTH: 9
<212> TYPE: PRT
<213> ORGANISM: Homo sapiens
<220> FEATURE:
<223> OTHER INFORMATION: Residues 117-125 of the hepsin protein

<400> SEQUENCE: 91

Phe Phe Cys Val Asp Glu Gly Arg Leu
                5

<210> SEQ ID NO 92
<211> LENGTH: 9
<212> TYPE: PRT
<213> ORGANISM: Homo sapiens
<220> FEATURE:
<223> OTHER INFORMATION: Residues 124-132 of the hepsin protein

<400> SEQUENCE: 92

Arg Leu Pro His Thr Gln Arg Leu Leu
                5

<210> SEQ ID NO 93
<211> LENGTH: 9
<212> TYPE: PRT
<213> ORGANISM: Homo sapiens
<220> FEATURE:
<223> OTHER INFORMATION: Residues 80-88 of the hepsin protein

<400> SEQUENCE: 93

Arg Ser Asn Ala Arg Val Ala Gly Leu
                5
```

```
<210> SEQ ID NO 94
<211> LENGTH: 9
<212> TYPE: PRT
<213> ORGANISM: Homo sapiens
<220> FEATURE:
<223> OTHER INFORMATION: Residues 68-76 of the hepsin protein

<400> SEQUENCE: 94

Lys Thr Glu Gly Thr Trp Arg Leu Leu
                5

<210> SEQ ID NO 95
<211> LENGTH: 9
<212> TYPE: PRT
<213> ORGANISM: Homo sapiens
<220> FEATURE:
<223> OTHER INFORMATION: Residues 340-348 of the hepsin protein

<400> SEQUENCE: 95

Gly Tyr Pro Glu Gly Gly Ile Asp Ala
                5

<210> SEQ ID NO 96
<211> LENGTH: 9
<212> TYPE: PRT
<213> ORGANISM: Homo sapiens
<220> FEATURE:
<223> OTHER INFORMATION: Residues 242-250 of the hepsin protein

<400> SEQUENCE: 96

Gly Tyr Leu Pro Phe Arg Asp Pro Asn
                5

<210> SEQ ID NO 97
<211> LENGTH: 9
<212> TYPE: PRT
<213> ORGANISM: Homo sapiens
<220> FEATURE:
<223> OTHER INFORMATION: Residues 51-59 of the hepsin protein

<400> SEQUENCE: 97

Leu Tyr Pro Val Gln Val Ser Ser Ala
                5

<210> SEQ ID NO 98
<211> LENGTH: 9
<212> TYPE: PRT
<213> ORGANISM: Homo sapiens
<220> FEATURE:
<223> OTHER INFORMATION: Residues 259-267 of the hepsin protein

<400> SEQUENCE: 98

Ala Leu Val His Leu Ser Ser Pro Leu
                5

<210> SEQ ID NO 99
<211> LENGTH: 9
<212> TYPE: PRT
<213> ORGANISM: Homo sapiens
<220> FEATURE:
<223> OTHER INFORMATION: Residues 277-285 of the hepsin protein

<400> SEQUENCE: 99

Cys Leu Pro Ala Ala Gly Gln Ala Leu
                5
```

```
<210> SEQ ID NO 100
<211> LENGTH: 9
<212> TYPE: PRT
<213> ORGANISM: Homo sapiens
<220> FEATURE:
<223> OTHER INFORMATION: Residues 191-199 of the hepsin protein

<400> SEQUENCE: 100

Ser Leu Leu Ser Gly Asp Trp Val Leu
                5

<210> SEQ ID NO 101
<211> LENGTH: 9
<212> TYPE: PRT
<213> ORGANISM: Homo sapiens
<220> FEATURE:
<223> OTHER INFORMATION: Residues 210-218 of the hepsin protein

<400> SEQUENCE: 101

Arg Val Leu Ser Arg Trp Arg Val Phe
                5

<210> SEQ ID NO 102
<211> LENGTH: 9
<212> TYPE: PRT
<213> ORGANISM: Homo sapiens
<220> FEATURE:
<223> OTHER INFORMATION: Residues 222-230 of the hepsin protein

<400> SEQUENCE: 102

Val Ala Gln Ala Ser Pro His Gly Leu
                5

<210> SEQ ID NO 103
<211> LENGTH: 9
<212> TYPE: PRT
<213> ORGANISM: Homo sapiens
<220> FEATURE:
<223> OTHER INFORMATION: Residues 236-244 of the hepsin protein

<400> SEQUENCE: 103

Ala Val Val Tyr His Gly Gly Tyr Leu
                5

<210> SEQ ID NO 104
<211> LENGTH: 9
<212> TYPE: PRT
<213> ORGANISM: Homo sapiens
<220> FEATURE:
<223> OTHER INFORMATION: Residues 19-27 of the hepsin protein

<400> SEQUENCE: 104

Ala Ala Leu Thr Ala Gly Thr Leu Leu
                5

<210> SEQ ID NO 105
<211> LENGTH: 9
<212> TYPE: PRT
<213> ORGANISM: Homo sapiens
<220> FEATURE:
<223> OTHER INFORMATION: Residues 36-44 of the hepsin protein

<400> SEQUENCE: 105

Ser Trp Ala Ile Val Ala Val Leu Leu
                5
```

```
<210> SEQ ID NO 106
<211> LENGTH: 9
<212> TYPE: PRT
<213> ORGANISM: Homo sapiens
<220> FEATURE:
<223> OTHER INFORMATION: Residues 35-43 of the hepsin protein

<400> SEQUENCE: 106

Ala Ser Trp Ala Ile Val Ala Val Leu
                5

<210> SEQ ID NO 107
<211> LENGTH: 9
<212> TYPE: PRT
<213> ORGANISM: Homo sapiens
<220> FEATURE:
<223> OTHER INFORMATION: Residues 300-308 of the hepsin protein

<400> SEQUENCE: 107

Gln Tyr Tyr Gly Gln Gln Ala Gly Val
                5

<210> SEQ ID NO 108
<211> LENGTH: 9
<212> TYPE: PRT
<213> ORGANISM: Homo sapiens
<220> FEATURE:
<223> OTHER INFORMATION: Residues 363-371 of the hepsin protein

<400> SEQUENCE: 108

Ile Ser Arg Thr Pro Arg Trp Arg Leu
                5

<210> SEQ ID NO 109
<211> LENGTH: 9
<212> TYPE: PRT
<213> ORGANISM: Homo sapiens
<220> FEATURE:
<223> OTHER INFORMATION: Residues 366-374 of the hepsin protein

<400> SEQUENCE: 109

Thr Pro Arg Trp Arg Leu Cys Gly Ile
                5

<210> SEQ ID NO 110
<211> LENGTH: 9
<212> TYPE: PRT
<213> ORGANISM: Homo sapiens
<220> FEATURE:
<223> OTHER INFORMATION: Residues 236-244 of the hepsin protein

<400> SEQUENCE: 110

Ala Val Val Tyr His Gly Gly Tyr Leu
                5

<210> SEQ ID NO 111
<211> LENGTH: 9
<212> TYPE: PRT
<213> ORGANISM: Homo sapiens
<220> FEATURE:
<223> OTHER INFORMATION: Residues 13-21 of the hepsin protein

<400> SEQUENCE: 111

Cys Ser Arg Pro Lys Val Ala Ala Leu
                5
```

```
<210> SEQ ID NO 112
<211> LENGTH: 9
<212> TYPE: PRT
<213> ORGANISM: Homo sapiens
<220> FEATURE:
<223> OTHER INFORMATION: Residues 179-187 of the hepsin protein

<400> SEQUENCE: 112

Ser Leu Arg Tyr Asp Gly Ala His Leu
                5

<210> SEQ ID NO 113
<211> LENGTH: 9
<212> TYPE: PRT
<213> ORGANISM: Homo sapiens
<220> FEATURE:
<223> OTHER INFORMATION: Residues 43-51 of the hepsin protein

<400> SEQUENCE: 113

Leu Leu Arg Ser Asp Gln Glu Pro Leu
                5

<210> SEQ ID NO 114
<211> LENGTH: 9
<212> TYPE: PRT
<213> ORGANISM: Homo sapiens
<220> FEATURE:
<223> OTHER INFORMATION: Residues 19-27 of the hepsin protein

<400> SEQUENCE: 114

Ala Ala Leu Thr Ala Gly Thr Leu Leu
                5

<210> SEQ ID NO 115
<211> LENGTH: 9
<212> TYPE: PRT
<213> ORGANISM: Homo sapiens
<220> FEATURE:
<223> OTHER INFORMATION: Residues 55-63 of the hepsin protein

<400> SEQUENCE: 115

Gln Val Ser Ser Ala Asp Ala Arg Leu
                5

<210> SEQ ID NO 116
<211> LENGTH: 9
<212> TYPE: PRT
<213> ORGANISM: Homo sapiens
<220> FEATURE:
<223> OTHER INFORMATION: Residues 163-171 of the hepsin protein

<400> SEQUENCE: 116

Ile Val Gly Gly Arg Asp Thr Ser Leu
                5

<210> SEQ ID NO 117
<211> LENGTH: 9
<212> TYPE: PRT
<213> ORGANISM: Homo sapiens
<220> FEATURE:
<223> OTHER INFORMATION: Residues 140-148 of the hepsin protein

<400> SEQUENCE: 117

Cys Pro Arg Gly Arg Phe Leu Ala Ala
                5
```

```
<210> SEQ ID NO 118
<211> LENGTH: 9
<212> TYPE: PRT
<213> ORGANISM: Homo sapiens
<220> FEATURE:
<223> OTHER INFORMATION: Residues 20-28 of the hepsin protein

<400> SEQUENCE: 118

Ala Leu Thr Ala Gly Thr Leu Leu Leu
                5

<210> SEQ ID NO 119
<211> LENGTH: 9
<212> TYPE: PRT
<213> ORGANISM: Homo sapiens
<220> FEATURE:
<223> OTHER INFORMATION: Residues 409-417 of the hepsin protein

<400> SEQUENCE: 119

Glu Ala Ser Gly Met Val Thr Gln Leu
                5

<210> SEQ ID NO 120
<211> LENGTH: 9
<212> TYPE: PRT
<213> ORGANISM: Homo sapiens
<220> FEATURE:
<223> OTHER INFORMATION: Residues 259-267 of the hepsin protein

<400> SEQUENCE: 120

Ala Leu Val His Leu Ser Ser Pro Leu
                5

<210> SEQ ID NO 121
<211> LENGTH: 9
<212> TYPE: PRT
<213> ORGANISM: Homo sapiens
<220> FEATURE:
<223> OTHER INFORMATION: Residues 35-43 of the hepsin protein

<400> SEQUENCE: 121

Ala Ser Trp Ala Ile Val Ala Val Leu
                5

<210> SEQ ID NO 122
<211> LENGTH: 9
<212> TYPE: PRT
<213> ORGANISM: Homo sapiens
<220> FEATURE:
<223> OTHER INFORMATION: Residues 184-192 of the hepsin protein

<400> SEQUENCE: 122

Gly Ala His Leu Cys Gly Gly Ser Leu
                5

<210> SEQ ID NO 123
<211> LENGTH: 9
<212> TYPE: PRT
<213> ORGANISM: Homo sapiens
<220> FEATURE:
<223> OTHER INFORMATION: Residues 18-26 of the hepsin protein

<400> SEQUENCE: 123

Val Ala Ala Leu Thr Ala Gly Thr Leu
                5
```

```
<210> SEQ ID NO 124
<211> LENGTH: 9
<212> TYPE: PRT
<213> ORGANISM: Homo sapiens
<220> FEATURE:
<223> OTHER INFORMATION: Residues 222-230 of the hepsin protein

<400> SEQUENCE: 124

Val Ala Gln Ala Ser Pro His Gly Leu
                 5

<210> SEQ ID NO 125
<211> LENGTH: 9
<212> TYPE: PRT
<213> ORGANISM: Homo sapiens
<220> FEATURE:
<223> OTHER INFORMATION: Residues 224-232 of the hepsin protein

<400> SEQUENCE: 125

Gln Ala Ser Pro His Gly Leu Gln Leu
                 5

<210> SEQ ID NO 126
<211> LENGTH: 9
<212> TYPE: PRT
<213> ORGANISM: Homo sapiens
<220> FEATURE:
<223> OTHER INFORMATION: Residues 265-273 of the hepsin protein

<400> SEQUENCE: 126

Ser Pro Leu Pro Leu Thr Glu Tyr Ile
                 5

<210> SEQ ID NO 127
<211> LENGTH: 9
<212> TYPE: PRT
<213> ORGANISM: Homo sapiens
<220> FEATURE:
<223> OTHER INFORMATION: Residues 355-363 of the hepsin protein

<400> SEQUENCE: 127

Gly Pro Phe Val Cys Glu Asp Ser Ile
                 5

<210> SEQ ID NO 128
<211> LENGTH: 9
<212> TYPE: PRT
<213> ORGANISM: Homo sapiens
<220> FEATURE:
<223> OTHER INFORMATION: Residues 13-21 of the hepsin protein

<400> SEQUENCE: 128

Cys Ser Arg Pro Lys Val Ala Ala Leu
                 5

<210> SEQ ID NO 129
<211> LENGTH: 9
<212> TYPE: PRT
<213> ORGANISM: Homo sapiens
<220> FEATURE:
<223> OTHER INFORMATION: Residues 366-374 of the hepsin protein

<400> SEQUENCE: 129

Thr Pro Arg Trp Arg Leu Cys Gly Ile
                 5
```

```
<210> SEQ ID NO 130
<211> LENGTH: 9
<212> TYPE: PRT
<213> ORGANISM: Homo sapiens
<220> FEATURE:
<223> OTHER INFORMATION: Residues 140-148 of the hepsin protein

<400> SEQUENCE: 130

Cys Pro Arg Gly Arg Phe Leu Ala Ala
                5

<210> SEQ ID NO 131
<211> LENGTH: 9
<212> TYPE: PRT
<213> ORGANISM: Homo sapiens
<220> FEATURE:
<223> OTHER INFORMATION: Residues 152-160 of the hepsin protein

<400> SEQUENCE: 131

Asp Cys Gly Arg Arg Lys Leu Pro Val
                5

<210> SEQ ID NO 132
<211> LENGTH: 9
<212> TYPE: PRT
<213> ORGANISM: Homo sapiens
<220> FEATURE:
<223> OTHER INFORMATION: Residues 363-371 of the hepsin protein

<400> SEQUENCE: 132

Ile Ser Arg Thr Pro Arg Trp Arg Leu
                5

<210> SEQ ID NO 133
<211> LENGTH: 9
<212> TYPE: PRT
<213> ORGANISM: Homo sapiens
<220> FEATURE:
<223> OTHER INFORMATION: Residues 133-141 of the hepsin protein

<400> SEQUENCE: 133

Ile Val Gly Gly Arg Asp Thr Ser Leu
                5

<210> SEQ ID NO 134
<211> LENGTH: 9
<212> TYPE: PRT
<213> ORGANISM: Homo sapiens
<220> FEATURE:
<223> OTHER INFORMATION: Residues 331-339 of the hepsin protein

<400> SEQUENCE: 134

Gln Ile Lys Pro Lys Met Phe Cys Ala
                5

<210> SEQ ID NO 135
<211> LENGTH: 9
<212> TYPE: PRT
<213> ORGANISM: Homo sapiens
<220> FEATURE:
<223> OTHER INFORMATION: Residues 80-88 of the hepsin protein

<400> SEQUENCE: 135

Arg Ser Asn Ala Arg Val Ala Gly Leu
                5
```

```
<210> SEQ ID NO 136
<211> LENGTH: 9
<212> TYPE: PRT
<213> ORGANISM: Homo sapiens
<220> FEATURE:
<223> OTHER INFORMATION: Residues 179-187 of the hepsin protein

<400> SEQUENCE: 136

Ser Leu Arg Tyr Asp Gly Ala His Leu
                5

<210> SEQ ID NO 137
<211> LENGTH: 9
<212> TYPE: PRT
<213> ORGANISM: Homo sapiens
<220> FEATURE:
<223> OTHER INFORMATION: Residues 43-51 of the hepsin protein

<400> SEQUENCE: 137

Leu Leu Arg Ser Asp Gln Glu Pro Leu
                5

<210> SEQ ID NO 138
<211> LENGTH: 9
<212> TYPE: PRT
<213> ORGANISM: Homo sapiens
<220> FEATURE:
<223> OTHER INFORMATION: Residues 409-417 of the hepsin protein

<400> SEQUENCE: 138

Glu Ala Ser Gly Met Val Thr Gln Leu
                5

<210> SEQ ID NO 139
<211> LENGTH: 9
<212> TYPE: PRT
<213> ORGANISM: Homo sapiens
<220> FEATURE:
<223> OTHER INFORMATION: Residues 311-319 of the hepsin protein

<400> SEQUENCE: 139

Glu Ala Arg Val Pro Ile Ile Ser Asn
                5

<210> SEQ ID NO 140
<211> LENGTH: 9
<212> TYPE: PRT
<213> ORGANISM: Homo sapiens
<220> FEATURE:
<223> OTHER INFORMATION: Residues 222-230 of the hepsin protein

<400> SEQUENCE: 140

Val Ala Gln Ala Ser Pro His Gly Leu
                5

<210> SEQ ID NO 141
<211> LENGTH: 9
<212> TYPE: PRT
<213> ORGANISM: Homo sapiens
<220> FEATURE:
<223> OTHER INFORMATION: Residues 19-27 of the hepsin protein

<400> SEQUENCE: 141

Ala Ala Leu Thr Ala Gly Thr Leu Leu
                5
```

```
<210> SEQ ID NO 142
<211> LENGTH: 9
<212> TYPE: PRT
<213> ORGANISM: Homo sapiens
<220> FEATURE:
<223> OTHER INFORMATION: Residues 18-26 of the hepsin protein

<400> SEQUENCE: 142

Val Ala Ala Leu Thr Ala Gly Thr Leu
                5

<210> SEQ ID NO 143
<211> LENGTH: 9
<212> TYPE: PRT
<213> ORGANISM: Homo sapiens
<220> FEATURE:
<223> OTHER INFORMATION: Residues 184-192 of the hepsin protein

<400> SEQUENCE: 143

Gly Ala His Leu Cys Gly Gly Ser Leu
                5

<210> SEQ ID NO 144
<211> LENGTH: 9
<212> TYPE: PRT
<213> ORGANISM: Homo sapiens
<220> FEATURE:
<223> OTHER INFORMATION: Residues 224-232 of the hepsin protein

<400> SEQUENCE: 144

Gln Ala Ser Pro His Gly Leu Gln Leu
                5

<210> SEQ ID NO 145
<211> LENGTH: 9
<212> TYPE: PRT
<213> ORGANISM: Homo sapiens
<220> FEATURE:
<223> OTHER INFORMATION: Residues 82-90 of the hepsin protein

<400> SEQUENCE: 145

Asn Ala Arg Val Ala Gly Leu Ser Cys
                5

<210> SEQ ID NO 146
<211> LENGTH: 9
<212> TYPE: PRT
<213> ORGANISM: Homo sapiens
<220> FEATURE:
<223> OTHER INFORMATION: Residues 204-212 of the hepsin protein

<400> SEQUENCE: 146

Cys Phe Pro Glu Arg Asn Arg Val Leu
                5

<210> SEQ ID NO 147
<211> LENGTH: 9
<212> TYPE: PRT
<213> ORGANISM: Homo sapiens
<220> FEATURE:
<223> OTHER INFORMATION: Residues 212-220 of the hepsin protein

<400> SEQUENCE: 147

Leu Ser Arg Trp Arg Val Phe Ala Gly
                5
```

```
<210> SEQ ID NO 148
<211> LENGTH: 9
<212> TYPE: PRT
<213> ORGANISM: Homo sapiens
<220> FEATURE:
<223> OTHER INFORMATION: Residues 172-180 of the hepsin protein

<400> SEQUENCE: 148

Gly Arg Trp Pro Trp Gln Val Ser Leu
                5

<210> SEQ ID NO 149
<211> LENGTH: 9
<212> TYPE: PRT
<213> ORGANISM: Homo sapiens
<220> FEATURE:
<223> OTHER INFORMATION: Residues 44-52 of the hepsin protein

<400> SEQUENCE: 149

Leu Arg Ser Asp Gln Glu Pro Leu Tyr
                5

<210> SEQ ID NO 150
<211> LENGTH: 9
<212> TYPE: PRT
<213> ORGANISM: Homo sapiens
<220> FEATURE:
<223> OTHER INFORMATION: Residues 155-163 of the hepsin protein

<400> SEQUENCE: 150

Arg Arg Lys Leu Pro Val Asp Arg Ile
                5

<210> SEQ ID NO 151
<211> LENGTH: 9
<212> TYPE: PRT
<213> ORGANISM: Homo sapiens
<220> FEATURE:
<223> OTHER INFORMATION: Residues 213-221 of the hepsin protein

<400> SEQUENCE: 151

Ser Arg Trp Arg Val Phe Ala Gly Ala
                5

<210> SEQ ID NO 152
<211> LENGTH: 9
<212> TYPE: PRT
<213> ORGANISM: Homo sapiens
<220> FEATURE:
<223> OTHER INFORMATION: Residues 166-174 of the hepsin protein

<400> SEQUENCE: 152

Gly Arg Asp Thr Ser Leu Gly Arg Trp
                5

<210> SEQ ID NO 153
<211> LENGTH: 9
<212> TYPE: PRT
<213> ORGANISM: Homo sapiens
<220> FEATURE:
<223> OTHER INFORMATION: Residues 369-377 of the hepsin protein

<400> SEQUENCE: 153

Trp Arg Leu Cys Gly Ile Val Ser Trp
                5
```

```
<210> SEQ ID NO 154
<211> LENGTH: 9
<212> TYPE: PRT
<213> ORGANISM: Homo sapiens
<220> FEATURE:
<223> OTHER INFORMATION: Residues 180-188 of the hepsin protein

<400> SEQUENCE: 154

Leu Arg Tyr Asp Gly Ala His Leu Cys
                5

<210> SEQ ID NO 155
<211> LENGTH: 9
<212> TYPE: PRT
<213> ORGANISM: Homo sapiens
<220> FEATURE:
<223> OTHER INFORMATION: Residues 96-104 of the hepsin protein

<400> SEQUENCE: 155

Leu Arg Ala Leu Thr His Ser Glu Leu
                5

<210> SEQ ID NO 156
<211> LENGTH: 9
<212> TYPE: PRT
<213> ORGANISM: Homo sapiens
<220> FEATURE:
<223> OTHER INFORMATION: Residues 396-404 of the hepsin protein

<400> SEQUENCE: 156

Phe Arg Glu Trp Ile Phe Gln Ala Ile
                5

<210> SEQ ID NO 157
<211> LENGTH: 9
<212> TYPE: PRT
<213> ORGANISM: Homo sapiens
<220> FEATURE:
<223> OTHER INFORMATION: Residues 123-131 of the hepsin protein

<400> SEQUENCE: 157

Gly Arg Leu Pro His Thr Gln Arg Leu
                5

<210> SEQ ID NO 158
<211> LENGTH: 9
<212> TYPE: PRT
<213> ORGANISM: Homo sapiens
<220> FEATURE:
<223> OTHER INFORMATION: Residues 207-215 of the hepsin protein

<400> SEQUENCE: 158

Glu Arg Asn Arg Val Leu Ser Arg Trp
                5

<210> SEQ ID NO 159
<211> LENGTH: 9
<212> TYPE: PRT
<213> ORGANISM: Homo sapiens
<220> FEATURE:
<223> OTHER INFORMATION: Residues 209-217 of the hepsin protein

<400> SEQUENCE: 159

Asn Arg Val Leu Ser Arg Trp Arg Val
                5
```

```
<210> SEQ ID NO 160
<211> LENGTH: 9
<212> TYPE: PRT
<213> ORGANISM: Homo sapiens
<220> FEATURE:
<223> OTHER INFORMATION: Residues 14-22 of the hepsin protein

<400> SEQUENCE: 160

Ser Arg Pro Lys Val Ala Ala Leu Thr
                5

<210> SEQ ID NO 161
<211> LENGTH: 9
<212> TYPE: PRT
<213> ORGANISM: Homo sapiens
<220> FEATURE:
<223> OTHER INFORMATION: Residues 106-114 of the hepsin protein

<400> SEQUENCE: 161

Val Arg Thr Ala Gly Ala Asn Gly Thr
                5

<210> SEQ ID NO 162
<211> LENGTH: 9
<212> TYPE: PRT
<213> ORGANISM: Homo sapiens
<220> FEATURE:
<223> OTHER INFORMATION: Residues 129-137 of the hepsin protein

<400> SEQUENCE: 162

Gln Arg Leu Leu Glu Val Ile Ser Val
                5

<210> SEQ ID NO 163
<211> LENGTH: 9
<212> TYPE: PRT
<213> ORGANISM: Homo sapiens
<220> FEATURE:
<223> OTHER INFORMATION: Residues 349-357 of the hepsin protein

<400> SEQUENCE: 163

Cys Gln Gly Asp Ser Gly Gly Pro Phe
                5

<210> SEQ ID NO 164
<211> LENGTH: 9
<212> TYPE: PRT
<213> ORGANISM: Homo sapiens
<220> FEATURE:
<223> OTHER INFORMATION: Residues 61-69 of the hepsin protein

<400> SEQUENCE: 164

Ala Arg Leu Met Val Phe Asp Lys Thr
                5

<210> SEQ ID NO 165
<211> LENGTH: 9
<212> TYPE: PRT
<213> ORGANISM: Homo sapiens
<220> FEATURE:
<223> OTHER INFORMATION: Residues 215-223 of the hepsin protein

<400> SEQUENCE: 165

Trp Arg Val Phe Ala Gly Ala Val Ala
                5
```

```
<210> SEQ ID NO 166
<211> LENGTH: 9
<212> TYPE: PRT
<213> ORGANISM: Homo sapiens
<220> FEATURE:
<223> OTHER INFORMATION: Residues 143-151 of the hepsin protein

<400> SEQUENCE: 166

Gly Arg Phe Leu Ala Ala Ile Cys Gln
                5

<210> SEQ ID NO 167
<211> LENGTH: 9
<212> TYPE: PRT
<213> ORGANISM: Homo sapiens
<220> FEATURE:
<223> OTHER INFORMATION: Residues 246-254 of the hepsin protein

<400> SEQUENCE: 167

Phe Arg Asp Pro Asn Ser Glu Glu Asn
                5

<210> SEQ ID NO 168
<211> LENGTH: 9
<212> TYPE: PRT
<213> ORGANISM: Homo sapiens
<220> FEATURE:
<223> OTHER INFORMATION: Residues 132-140 of the hepsin protein

<400> SEQUENCE: 168

Leu Glu Val Ile Ser Val Cys Asp Cys
                5

<210> SEQ ID NO 169
<211> LENGTH: 9
<212> TYPE: PRT
<213> ORGANISM: Homo sapiens
<220> FEATURE:
<223> OTHER INFORMATION: Residues 91-99 of the hepsin protein

<400> SEQUENCE: 169

Glu Glu Met Gly Phe Leu Arg Ala Leu
                5

<210> SEQ ID NO 170
<211> LENGTH: 9
<212> TYPE: PRT
<213> ORGANISM: Homo sapiens
<220> FEATURE:
<223> OTHER INFORMATION: Residues 264-272 of the hepsin protein

<400> SEQUENCE: 170

Ser Ser Pro Leu Pro Leu Thr Glu Tyr
                5

<210> SEQ ID NO 171
<211> LENGTH: 9
<212> TYPE: PRT
<213> ORGANISM: Homo sapiens
<220> FEATURE:
<223> OTHER INFORMATION: Residues 310-318 of the hepsin protein

<400> SEQUENCE: 171

Gln Glu Ala Arg Val Pro Ile Ile Ser
                5
```

```
<210> SEQ ID NO 172
<211> LENGTH: 9
<212> TYPE: PRT
<213> ORGANISM: Homo sapiens
<220> FEATURE:
<223> OTHER INFORMATION: Residues 319-327 of the hepsin protein

<400> SEQUENCE: 172

Asn Asp Val Cys Asn Gly Ala Asp Phe
                5

<210> SEQ ID NO 173
<211> LENGTH: 9
<212> TYPE: PRT
<213> ORGANISM: Homo sapiens
<220> FEATURE:
<223> OTHER INFORMATION: Residues 4-12 of the hepsin protein

<400> SEQUENCE: 173

Lys Glu Gly Gly Arg Thr Val Pro Cys
                5

<210> SEQ ID NO 174
<211> LENGTH: 9
<212> TYPE: PRT
<213> ORGANISM: Homo sapiens
<220> FEATURE:
<223> OTHER INFORMATION: Residues 251-259 of the hepsin protein

<400> SEQUENCE: 174

Ser Glu Glu Asn Ser Asn Asp Ile Ala
                5

<210> SEQ ID NO 175
<211> LENGTH: 9
<212> TYPE: PRT
<213> ORGANISM: Homo sapiens
<220> FEATURE:
<223> OTHER INFORMATION: Residues 256-264 of the hepsin protein

<400> SEQUENCE: 175

Asn Asp Ile Ala Leu Val His Leu Ser
                5

<210> SEQ ID NO 176
<211> LENGTH: 9
<212> TYPE: PRT
<213> ORGANISM: Homo sapiens
<220> FEATURE:
<223> OTHER INFORMATION: Residues 294-302 of the hepsin protein

<400> SEQUENCE: 176

Thr Gly Trp Gly Asn Thr Gln Tyr Tyr
                5

<210> SEQ ID NO 177
<211> LENGTH: 9
<212> TYPE: PRT
<213> ORGANISM: Homo sapiens
<220> FEATURE:
<223> OTHER INFORMATION: Residues 361-369 of the hepsin protein

<400> SEQUENCE: 177

Asp Ser Ile Ser Arg Thr Pro Arg Trp
                5
```

```
<210> SEQ ID NO 178
<211> LENGTH: 9
<212> TYPE: PRT
<213> ORGANISM: Homo sapiens
<220> FEATURE:
<223> OTHER INFORMATION: Residues 235-243 of the hepsin protein

<400> SEQUENCE: 178

Gln Ala Val Val Tyr His Gly Gly Tyr
                 5

<210> SEQ ID NO 179
<211> LENGTH: 9
<212> TYPE: PRT
<213> ORGANISM: Homo sapiens
<220> FEATURE:
<223> OTHER INFORMATION: Residues 109-117 of the hepsin protein

<400> SEQUENCE: 179

Ala Gly Ala Asn Gly Thr Ser Gly Phe
                 5

<210> SEQ ID NO 180
<211> LENGTH: 9
<212> TYPE: PRT
<213> ORGANISM: Homo sapiens
<220> FEATURE:
<223> OTHER INFORMATION: Residues 270-278 of the hepsin protein

<400> SEQUENCE: 180

Thr Glu Tyr Ile Gln Pro Val Cys Leu
                 5

<210> SEQ ID NO 181
<211> LENGTH: 9
<212> TYPE: PRT
<213> ORGANISM: Homo sapiens
<220> FEATURE:
<223> OTHER INFORMATION: Residues 174-182 of the hepsin protein

<400> SEQUENCE: 181

Trp Pro Trp Gln Val Ser Leu Arg Tyr

<210> SEQ ID NO 182
<211> LENGTH: 9
<212> TYPE: PRT
<213> ORGANISM: Homo sapiens
<220> FEATURE:
<223> OTHER INFORMATION: Residues 293-301 of the hepsin protein

<400> SEQUENCE: 182

Val Thr Gly Trp Gly Asn Thr Gln Tyr
                 5

<210> SEQ ID NO 183
<211> LENGTH: 9
<212> TYPE: PRT
<213> ORGANISM: Homo sapiens
<220> FEATURE:
<223> OTHER INFORMATION: Residues 69-77 of the hepsin protein

<400> SEQUENCE: 183

Thr Glu Gly Thr Trp Arg Leu Leu Cys
                 5
```

-continued

```
<210> SEQ ID NO 184
<211> LENGTH: 9
<212> TYPE: PRT
<213> ORGANISM: Homo sapiens
<220> FEATURE:
<223> OTHER INFORMATION: Residues 90-98 of the hepsin protein

<400> SEQUENCE: 184

Cys Glu Glu Met Gly Phe Leu Arg Ala
                 5

<210> SEQ ID NO 185
<211> LENGTH: 9
<212> TYPE: PRT
<213> ORGANISM: Homo sapiens
<220> FEATURE:
<223> OTHER INFORMATION: Residues 252-260 of the hepsin protein

<400> SEQUENCE: 185

Glu Glu Asn Ser Asn Asp Ile Ala Leu
                 5

<210> SEQ ID NO 186
<211> LENGTH: 9
<212> TYPE: PRT
<213> ORGANISM: Homo sapiens
<220> FEATURE:
<223> OTHER INFORMATION: Residues 48-56 of the hepsin protein

<400> SEQUENCE: 186

Gln Glu Pro Leu Tyr Pro Val Gln Val
                 5

<210> SEQ ID NO 187
<211> LENGTH: 9
<212> TYPE: PRT
<213> ORGANISM: Homo sapiens
<220> FEATURE:
<223> OTHER INFORMATION: Residues 102-110 of the hepsin protein

<400> SEQUENCE: 187

Ser Glu Leu Asp Val Arg Thr Ala Gly
                 5

<210> SEQ ID NO 188
<211> LENGTH: 1783
<212> TYPE: DNA
<213> ORGANISM: Homo sapiens
<220> FEATURE:
<223> OTHER INFORMATION: full length cDNA of hepsin

<400> SEQUENCE: 188
tcgagcccgc tttccaggga ccctacctga gggcccacag gtgaggcagc         50
ctggcctagc aggccccacg ccaccgcctc tgcctccagg ccgcccgctg        100
ctgcggggcc accatgctcc tgcccaggcc tggagactga cccgaccccg        150
gcactacctc gaggctccgc ccccacctgc tggaccccag ggtcccaccc        200
tggcccagga ggtcagccag ggaatcatta acaagaggca gtgacatggc        250
gcagaaggag ggtggccgga ctgtgccatg ctgctccaga cccaaggtgg        300
cagctctcac tgcggggacc ctgctacttc tgacagccat cggggcggca        350
tcctgggcca ttgtggctgt tctcctcagg agtgaccagg agccgctgta        400
cccagtgcag gtcagctctg cggacgctcg gctcatggtc tttgacaaga        450
cggaagggac gtggcggctg ctgtgctcct cgcgctccaa cgccagggta        500
```

-continued

```
gccggactca gctgcgagga gatgggcttc ctcagggcac tgacccactc    550
cgagctggac gtgcgaacgg cgggcgccaa tggcacgtcg ggcttcttct    600
gtgtggacga ggggaggctg ccccacaccc agaggctgct ggaggtcatc    650
tccgtgtgtg attgccccag aggccgtttc ttggccgcca tctgccaaga    700
ctgtggccgc aggaagctgc ccgtggaccg catcgtggga ggccgggaca    750
ccagcttggg ccgtggccg tggcaagtca gccttcgcta tgatggagca     800
cacctctgtg ggggatccct gctctccggg gactgggtgc tgacagccgc    850
ccactgcttc ccggagcgga accgggtcct gtcccgatgg cgagtgtttg    900
ccggtgccgt ggcccaggcc tctccccacg tctgcagct gggggtgcag     950 gctgtggtct accacggggg ctatcttccc tttcggacc ccaacagcga     1000 ggagaacagc aacgatattg ccctggtcca cctctccagt cccctgcccc    1050
tcacagaata catccagcct gtgtgcctcc cagctgccgg ccaggccctg    1100
gtggatggca agatctgtac cgtgacgggc tggggcaaca cgcagtacta    1150
tggccaacag gccggggtac tccaggaggc tcgagtcccc ataatcagca    1200
atgatgtctg caatggcgct gacttctatg gaaaccagat caagcccaag    1250
atgttctgtg ctggctaccc cgagggtggc attgatgcct gcagggcga    1300 cagcggtggt ccctttgtgt gtgaggacag catctctcgg acgccacgtt    1350
ggcggctgtg tggcattgtg agttggggca ctggctgtgc cctggcccag    1400
aagccaggcg tctacaccaa agtcagtgac ttccgggagt ggatcttcca    1450
ggccataaag actcactccg aagccagcgg catggtgacc cagctctgac    1500
cggtggcttc tcgctgcgca gcctccaggg cccgaggtga tcccggtggt    1550
gggatccacg ctgggccgag gatgggacgt ttttcttctt gggcccggtc    1600
cacaggtcca aggacaccct ccctccaggg tcctctcttc cacagtggcg    1650
ggcccactca gccccgagac cacccaacct caccctcctg accccatgt     1700 aaatattgtt ctgctgtctg ggactcctgt ctaggtgccc ctgatgatgg    1750
gatgctcttt aaataataaa gatggttttg att                      1783
```

<210> SEQ ID NO 189
<211> LENGTH: 10
<212> TYPE: PRT
<213> ORGANISM: Homo sapiens
<220> FEATURE:
<223> OTHER INFORMATION: Residues 42-51 of the hepsin protein

<400> SEQUENCE: 189

Val Leu Leu Arg Ser Asp Ile Cys Thr Val
                5                   10

<210> SEQ ID NO 190
<211> LENGTH: 10
<212> TYPE: PRT
<213> ORGANISM: Homo sapiens
<220> FEATURE:
<223> OTHER INFORMATION: Residues 284-293 of the hepsin protein

<400> SEQUENCE: 190

Ala Leu Val Asp Gly Lys Ile Cys Thr Val
                5                   10

```
<210> SEQ ID NO 191
<211> LENGTH: 10
<212> TYPE: PRT
<213> ORGANISM: Homo sapiens
<220> FEATURE:
<223> OTHER INFORMATION: Residues 308-317 of the hepsin protein

<400> SEQUENCE: 191

Val Leu Gln Glu Ala Arg Val Pro Ile Ile
                 5                   10
```

METHODS FOR THE EARLY DIAGNOSIS OF OVARIAN CANCER

CROSS-REFERENCE TO RELATED APPLICATIONS

This is a continuation-in-part application which claims the benefit of priority under 35 USC §120 of U.S. Ser. No. 10/102,283, filed Mar. 20, 2002, now U.S. Pat. No. 6,875,609, which is a continuation-in-part application of U.S. Ser. No. 09/919,048, filed Jul. 30, 2001, now U.S. Pat. No. 6,787,354, which is a continuation-in-part application of U.S. Ser. No. 09/861,966, filed May 21, 2001, now U.S. Pat. No. 6,518,028, which is a divisional application of U.S. application Ser. No. 09/510,738 filed Feb. 22, 2000, now U.S. Pat. No. 6,268,165, which claims benefit of priority under 35 USC §120 of U.S. Ser. No. 09/039,211, filed Mar. 14, 1998, which claims benefit of provisional patent application U.S. Ser. No. 60/041,404, filed Mar. 19, 1997, now abandoned.

BACKGROUND OF THE INVENTION

1. Field of the Invention

Generally, the present invention relates to the fields of molecular biology and medicine. More specifically, the present invention is in the field of cancer research, especially ovarian cancer diagnosis.

2. Background of the Invention

In order for malignant cells to grow, spread or metastasize, they must have the capacity to invade local host tissue, dissociate or shed from the primary tumor, enter and survive in the bloodstream, implant by invasion into the surface of the target organ and establish an environment conducive for new colony growth (including the induction of angiogenic and growth factors). During this progression, natural tissue barriers such as basement membranes and connective tissue have to be degraded. These barriers include collagen, laminin, fibronectin, proteoglycans and extracellular matrix glycoproteins. Degradation of these natural barriers, both those surrounding the primary tumor and at the sites of metastatic invasion, is believed to be brought about by the action of a matrix of extracellular proteases.

Proteases have been classified into four families: serine proteases, metallo-proteases, aspartic proteases and cysteine proteases. Many proteases have been shown to be involved in human disease processes and these enzymes are targets for the development of inhibitors as new therapeutic agents. Certain individual proteases are induced and overexpressed in a diverse group of cancers, and as such, are potential candidates for markers of early diagnosis and targets for possible therapeutic intervention. A group of examples are shown in Table 1.

TABLE 1

Known proteases expressed in various cancers

| | Gastric | Brain | Breast | Ovarian |
|---|---|---|---|---|
| Serine Proteases: | uPA PAI-1 | uPA PAI-1 tPA | NES-1 uPA | NES-1 uPA PAI-2 |
| Cysteine Proteases: | Cathepsin B Cathepsin L | Cathepsin L | Cathepsin B Cathepsin L | Cathepsin B Cathepsin L |
| Metallo-proteases: | Matrilysin* Collagenase* Stromelysin-1* | Matrilysin Stromelysin Gelatinase B | Stromelysin-3 MMP-8 MMP-9 Gelatinase A | MMP-2 | uPA, Urokinase-type plasminogen activator; tPA, Tissue-type plasminogen activator; PAI-I, Plasminogen activator 0 inhibitors; PAI-2, Plasminogen activator inhibitors; NES-1, Normal epithelial cell-specific-1; MMP, Matrix P metallo protease.
*Overexpressed in gastrointestinal ulcers.

There is a good body of evidence supporting the downregulation or inhibition of individual proteases and the reduction in invasive capacity or malignancy. In work by Clark et al., inhibition of in vitro growth of human small cell lung cancer was demonstrated using a general serine protease inhibitor. More recently, Torres-Rosedo et al., [Proc. Natl. Acad. Sci. USA. 90, 7181-7185 (1993)] demonstrated an inhibition of hepatoma tumor cell growth using specific antisense inhibitors for the serine protease hepsin gene. Metastatic potential of melanoma cells has also been shown to be reduced in a mouse model using a synthetic inhibitor (batimastat) of metallo-proteases. Powell et al. [Cancer Research, 53, 417-422 (1993)] presented evidence to confirm that the expression of extracellular proteases in a non-metastatic prostate cancer cell line enhances their malignant progression. Specifically, enhanced metastasis was demonstrated after introducing and expressing the PUMP-1 metallo-protease gene. There is also a body of data to support the notion that expression of cell surface proteases on relatively non-metastatic cell types increases the invasive potential of such cells.

To date, ovarian cancer remains the number one killer of women with gynecologic malignant hyperplasia. Approximately 75% of women diagnosed with such cancers are already at an advanced stage (III and IV) of the disease at their initial diagnosis. During the past 20 years, neither diagnosis nor five-year survival rates have greatly improved for these patients. This is substantially due to the high percentage of high-stage initial detection of the disease. Therefore, the challenge remains to develop new markers that improve early diagnosis and thereby reduce the percentage of high-stage initial diagnoses. The ability to disengage from one tissue and re-engage the surface of another tissue is what provides for the morbidity and mortality associated with this disease. Therefore, extracellular proteases may be good candidates for markers of malignant ovarian hyperplasia.

Thus, the prior art is deficient in a tumor marker useful as an indicator of early disease, particularly for ovarian cancers. The present invention fulfills this long-standing need and desire in the art.

SUMMARY OF THE INVENTION

This invention allows for the detection of cancer, especially ovarian cancer, by screening for hepsin mRNA in tissue, which is indicative of the hepsin protease, which is shown herein to be specifically associated with the surface of 80 percent of ovarian and other tumors. Proteases are considered to be an integral part of tumor growth and metastasis, and therefore, markers indicative of their presence or absence are useful for the diagnosis of cancer. Furthermore, the present invention is useful for treatment (i.e., by inhibiting hepsin or expression of hepsin), for targeted therapy, for vaccination, etc.

In one embodiment of the present invention, there is provided a method for detecting malignant hyperplasia in a biological sample by detecting hepsin mRNA in the sample. The presence of the hepsin mRNA in the sample is indicative of the presence of malignant hyperplasia, and the absence of the hepsin mRNA in the sample is indicative of the absence of malignant hyperplasia.

In another embodiment of the present invention, there are provided methods of inhibiting expression of hepsin in a cell by introducing into a cell a vector encoding an antisense hepsin mRNA or an antibody that binds the hepsin protein.

In yet another embodiment of the present invention, there is provided a method of targeted therapy to an individual, comprising the step of administering a compound to an individual, wherein the compound has a targeting moiety and a therapeutic moiety, wherein the targeting moiety is specific for hepsin.

In still yet another embodiment of the present invention, there are provided methods of vaccinating an individual against hepsin or produce immune-activated cells directed toward hepsin by inoculating an individual with an expression vector encoding a hepsin protein or a fragment thereof.

The present invention also provides methods of immunotherapy targeted toward hepsin in an individual, involving the steps of generating dendritic cells in vitro from peripheral blood drawn from an individual, loading these dendritic cells with hepsin protein or a fragment thereof, then transferring these dendritic cells back to the individual in single or multiple doses. Hepsin-loaded or hepsin-expressing dendritic cells can also be used to stimulate hepsin-specific T cell responses in vitro, followed by adoptive immunotherapy in which the individual is given autologous hepsin-specific T cells.

In another embodiment of the present invention, there are provided compositions comprising immunogenic fragments of hepsin protein or an oligonucleotide having a sequence complementary to SEQ ID No.188. Also embodied is a method of treating a neoplastic state in an individual in need of such treatment with an effective dose of the above-described oligonucleotide.

In another embodiment of the present invention, there is provided a method of screening for compounds that inhibit hepsin activity, comprising the steps of contacting a sample with a compound, wherein the sample comprises hepsin protein; and assaying for hepsin protease activity. A decrease in the hepsin protease activity in the presence of the compound relative to hepsin protease activity in the absence of the compound is indicative of a compound that inhibits hepsin activity.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 15 shows the TADG-12 catalytic domain including an insert near the His 5'-end.

DETAILED DESCRIPTION OF THE INVENTION

Figure 1:
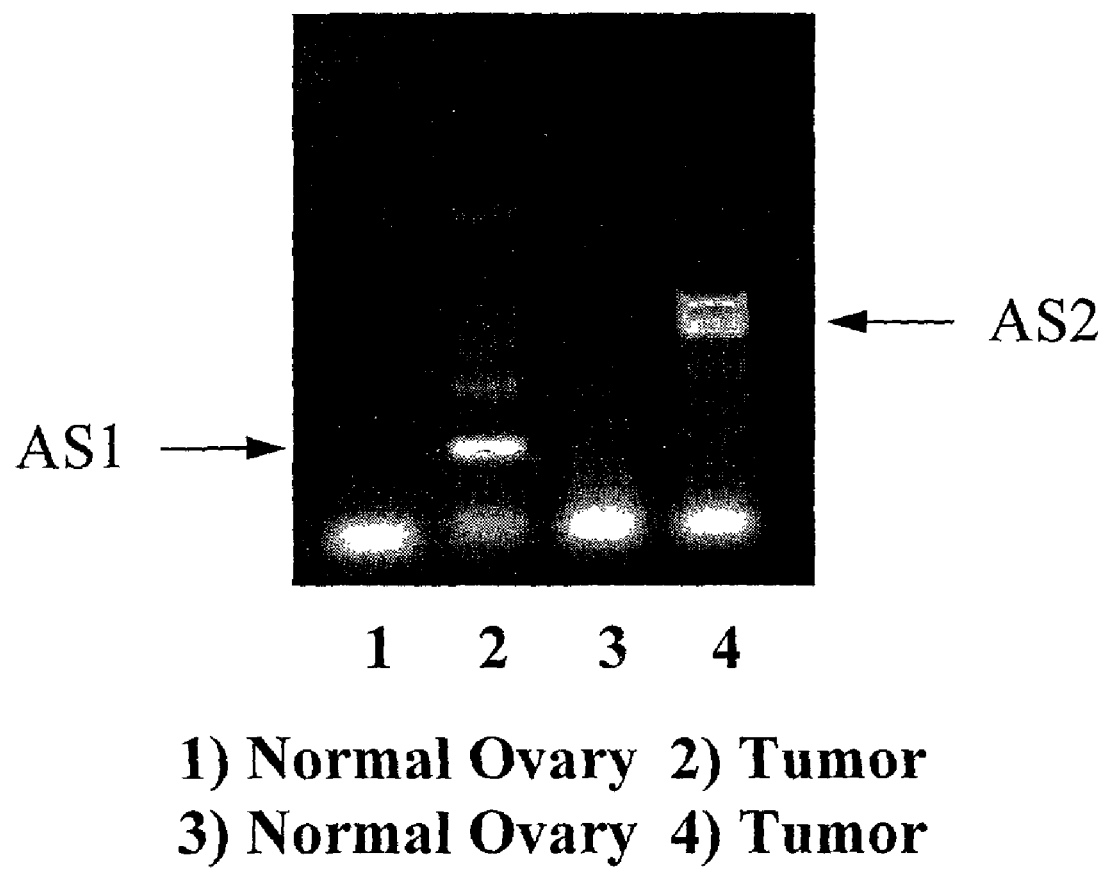
FIG. 1 shows agarose gel comparison of PCR products derived from normal and carcinoma cDNA.

This invention identifies hepsin protease as a marker for ovarian tumor cells. In various combinations with other proteases, hepsin expression is characteristic of individual tumor types. Such information can provide the basis for diagnostic tests (assays or immunohistochemistry) and prognostic evaluation (depending on the display pattern). Long-term treatment of tumor growth, invasion and metastasis has not succeeded with existing chemotherapeutic agents. Most tumors become resistant to drugs after multiple cycles of chemotherapy. The present invention identifies hepsin as a new therapeutic intervention target utilizing either antibodies directed at the protease, antisense vehicles for downregulation or protease inhibitors for the design of new drugs.

A primary object of the present invention is a method for detecting the presence of malignant hyperplasia in a tissue sample. The cancer is detected by analyzing a biological sample for the presence of markers to proteases that are specific indicators of certain types of cancer cells. This object may be accomplished by isolating mRNA from a sample or by detection of proteins by polyclonal or preferably monoclonal antibodies. When using mRNA detection, the method may be carried out by converting the isolated mRNA to cDNA according to standard methods; treating the converted cDNA with amplification reaction reagents (such as cDNA PCR reaction reagents) in a container along with an appropriate mixture of nucleic acid primers selected from the list in Table 2; reacting the contents of the container to produce amplification products; and analyzing the amplification products to detect the presence of malignant hyperplasia markers in the sample. The analyzing step may be accomplished using Northern Blot analysis to detect the presence of malignant hyperplasia markers in the amplification product. Northern Blot analysis is known in the art. The analysis step may be further accomplished by quantitatively detecting the presence of malignant hyperplasia marker in the amplification products, and comparing the quantity of marker detected against a panel of expected values for known presence or absence in normal and malignant tissue derived using similar primers.

The present invention also provides various nucleic acid sequences that are useful in the methods disclosed herein. These nucleic acid sequences are listed in Table 2. It is anticipated that these nucleic acid sequences be used in mixtures to accomplish the utility of this invention. The skilled artisan may be able to develop other nucleic acid sequences and mixtures thereof to accomplish the benefit of this invention, but it is advantageous to have the sequences listed in Table 2 available without undue experimentation.

The present invention provides a method for detecting malignant hyperplasia in a biological sample, comprising the steps of isolating mRNA from the sample; and detecting hepsin mRNA in the sample. The presence of the hepsin mRNA in the sample is indicative of the presence of malignant hyperplasia, wherein the absence of the hepsin mRNA in the sample is indicative of the absence of malignant hyperplasia. This method may further comprise the step of comparing the hepsin mRNA to reference information, wherein the comparison provides a diagnosis and/or determines a treatment of the malignant hyperplasia. A typical means of detection of hepsin mRNA is by PCR amplification, which, preferably, uses primers shown in SEQ ID No. 8 and SEQ ID No. 9. Representative biological samples are blood, urine, saliva, tears, interstitial fluid, ascites fluid, tumor tissue biopsy and circulating tumor cells.

The present invention is further directed toward a method of inhibiting expression of hepsin in a cell, comprising the step of introducing into a cell a vector comprises a hepsin gene operably linked in opposite orientation to elements necessary for expression, wherein expression of the vector produces hepsin antisense mRNA in the cell. The hepsin antisense mRNA hybridizes to endogenous hepsin mRNA, thereby inhibiting expression of hepsin in the cell.

The present invention is still further directed toward a method of inhibiting a hepsin protein in a cell, comprising the step of introducing an antibody into a cell, wherein the antibody is specific for a hepsin protein or a fragment thereof. Binding of the antibody to hepsin inhibits the hepsin protein. Preferably, the hepsin fragment is a 9-residue fragment up to a 20-residue fragment, and more preferably, the fragment is SEQ ID Nos. 28, 29, 30, 31, 88, 89, 108, 109, 128, 129, 148, 149, 150, 151, 152, 153, 154, 189, 190 or 191.

The present invention is also directed toward a method of targeted therapy to an individual, comprising the step of administering a compound to an individual, wherein the compound has a targeting moiety and a therapeutic moiety, and wherein the targeting moiety is specific for hepsin. Preferably, the targeting moiety is an antibody specific for hepsin or a ligand or ligand binding domain that binds hepsin. Likewise, the therapeutic moiety is preferably a radioisotope, a toxin, a chemotherapeutic agent, an immune stimulant or cytotoxic agent. Generally, the individual suffers from a disease such as ovarian cancer, lung cancer, prostate cancer, colon cancer or another cancer in which hepsin is overexpressed.

The present invention is additionally directed toward a method of vaccinating an individual against hepsin, comprising the steps of inoculating an individual with an expression vector encoding a hepsin protein or a fragment thereof. Expression of the hepsin protein, or fragment thereof, elicits an immune response in the individual, thereby vaccinating the individual against hepsin. Generally, this method is applicable when the individual has cancer or is at risk of getting a cancer such as ovarian cancer, lung cancer, prostate cancer and colon cancer. Sequences of preferred hepsin proteins or fragment thereof are shown in SEQ ID Nos. 28, 29, 30, 31, 88, 89, 108, 109, 128, 129, 148, 149, 150, 151, 152, 153, 154, 189, 190 and 191.

The present invention is yet directed toward a method of producing immune-activated cells directed toward hepsin, comprising the steps of exposing immune cells to hepsin protein or fragment thereof. Typically, exposure to hepsin protein or fragment thereof activates the immune cells, thereby producing immune-activated cells directed toward hepsin. Generally, the immune-activated cells are B-cells, T-cells and/or dendritic cells. Preferably, the hepsin fragment is a 9-residue fragment up to a 20-residue fragment, and more preferably, the fragment is SEQ ID Nos. 28, 29, 30, 31, 88, 89, 108, 109, 128, 129, 148, 149, 150, 151, 152, 153, 154, 189, 190 or 191. Oftentimes, the dendritic cells are isolated from an individual prior to exposure and then reintroduced into the individual subsequent to the exposure. Typically, the individual has cancer or is at risk of getting a cancer such as ovarian cancer, lung cancer, prostate cancer and colon cancer.

The present invention also provides methods of immunotherapy targeted toward hepsin in an individual. The methods involve generating dendritic cells in vitro from peripheral blood drawn from the individual, loading/introducing these dendritic cells with hepsin protein or a fragment thereof by lipofection or other means, then transferring these dendritic cells back to the individual in single or multiple doses. Hepsin may also be expressed in these dendritic cells following transduction with a recombinant DNA vector. Alternatively, hepsin-loaded or hepsin-expressing dendritic cells can be used to stimulate hepsin-specific T cell responses in vitro, followed by adoptive immunotherapy in which the individual is given autologous hepsin-specific T cells. Typically, the individual has cancer or is at risk of getting a cancer such as ovarian cancer, lung cancer, prostate cancer and colon cancer. In general, a full length or a fragment of hepsin protein is expressed in the isolated dendritic cells. Preferably, the fragment is a 9-residue fragment up to a 20-residue fragment, and more preferably, the fragment is SEQ ID Nos. 28, 29, 30, 31, 88, 89, 108, 109, 128, 129, 148, 149, 150, 151, 152, 153, 154, 189, 190 or 191.

The present invention is further directed toward an immunogenic composition, comprising an appropriate adjuvant and an immunogenic full length hepsin protein or a fragment thereof. Preferably, the fragment is a 9-residue fragment up to a 20-residue fragment, and more preferably, the fragment is SEQ ID Nos. 28, 29, 30, 31, 88, 89, 108, 109, 128, 129, 148, 149, 150, 151, 152, 153, 154, 189, 190 or 191.

The present invention is further directed toward an oligonucleotide having a sequence complementary to SEQ ID No.188 or a fragment thereof. The present invention further provides a composition comprising the above-described oligonucleotide and a physiologically acceptable carrier, and a method of treating a neoplastic state in an individual in need of such treatment, comprising the step of administering to the individual an effective dose of the above-described oligonucleotide. Typically, the neoplastic state may be ovarian cancer, breast cancer, lung cancer, colon cancer, prostate cancer or another cancer in which hepsin is overexpressed.

The present invention is still further directed toward a method of screening for compounds that inhibit hepsin activity, comprising the steps of contacting a sample with a compound, wherein the sample comprises hepsin protein; and assaying for hepsin protease activity. A decrease in the hepsin protease activity in the presence of the compound relative to hepsin protease activity in the absence of the compound is indicative of a compound that inhibits hepsin activity.

It will be apparent to one skilled in the art that various substitutions and modifications may be made to the invention disclosed herein without departing from the scope and spirit of the invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "PCR" refers to the polymerase chain reaction that is the subject of U.S. Pat. Nos. 4,683,195 and 4,683,202 to Mullis, as well as other improvements now known in the art.

The present invention comprises a vector comprising a DNA sequence which encodes a hepsin protein or a fragment thereof, wherein said vector is capable of replication in a host, and comprises, in operable linkage: a) an origin of replication; b) a promoter; and c) a DNA sequence coding for said hepsin protein. Preferably, the vector of the present invention contains a portion of the DNA sequence shown in SEQ ID No. 188. Vectors may be used to amplify and/or express nucleic acid encoding a hepsin protein, a fragment of hepsin protein, or an antisense hepsin mRNA. Furthermore, the vectors may express nucleic acid encoding a fusion protein comprising an immunologically active component and a hepsin protein or a fragment thereof. These vectors would be useful in methods of vaccination against hepsin in an individual.

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites and sequences which control the termination of transcription and translation. Methods that are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

As used herein, the term "host" is meant to include not only prokaryotes but also eukaryotes such as yeast, plant and animal cells. A recombinant DNA molecule or gene which encodes a human hepsin protein of the present invention can be used to transform a host using any of the techniques commonly known to those of ordinary skill in the art. Especially preferred is the use of a vector containing coding sequences for the gene that encodes a human hepsin protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15-25 or more nucleotides, depending upon the complexity of the target sequence, although it may contain fewer nucleotides.

The primers herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID No. 188 or the complement thereof. Such a probe is useful for detecting expression of hepsin in a cell by a method including the steps of (a) contacting mRNA obtained from the cell with a labeled hepsin hybridization probe; and (b) detecting hybridization of the probe with the mRNA.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID No. 188 and which encodes an alternative splice variant of hepsin.

The DNA may have at least about 70% sequence identity to the coding sequence of the nucleotides listed in SEQ ID No. 188, preferably at least 75% (e.g., at least 80%); and most preferably at least 90%. The identity between two sequences is a direct function of the number of matching or identical positions. When a position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group (GCG), University of Wisconsin Biotechnology Center, 1710 University Avenue, Madison, Wis. 53705).

Further included in this invention are hepsin proteins which are encoded, at least in part, by portions of SEQ ID No. 188, e.g., products of alternative mRNA splicing or alternative protein processing events, or in which a section of hepsin sequence has been deleted. The fragment, or the intact hepsin polypeptide, may be covalently linked to another polypeptide, e.g., one which acts as a label, a ligand or a means to increase antigenicity.

A substantially pure hepsin protein may be obtained, for example, by extraction from a natural source; by expression of a recombinant nucleic acid encoding a hepsin polypeptide; or by chemically synthesizing the protein. Purity can be measured by any appropriate method, e.g., column chromatography, such as immunoaffinity chromatography using an antibody specific for hepsin, polyacrylamide gel electrophoresis, or HPLC analysis. A protein is substantially free of naturally associated components when it is separated from at least some of those contaminants that accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the hepsin protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the hepsin protein can be generated by methods known to those skilled in the art, e.g., by enzymatic digestion of naturally occurring or recombinant hepsin protein, by recombinant DNA techniques using an expression vector that encodes a defined fragment of hepsin, or by chemical synthesis. The ability of a candidate fragment to exhibit a characteristic of hepsin (e.g., binding to an antibody specific for hepsin) can be assessed by methods known in the art. Purified hepsin or antigenic fragments of hepsin can be used to generate new antibodies or to test existing antibodies (e.g., as positive controls in a diagnostic assay) by employing standard protocols known to those skilled in the art. Included in this invention is polyclonal antisera generated by using hepsin or a fragment of hepsin as the immunogen in, e.g., rabbits.

Standard protocols for monoclonal and polyclonal antibody production known to those skilled in this art are employed. The monoclonal antibodies generated by this procedure can be screened for the ability to identify recombinant hepsin cDNA clones, and to distinguish them from other cDNA clones.

The invention encompasses not only an intact anti-hepsin monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g., a radioactive label, non-radioactive isotopic label, fluorescent label, chemiluminescent label, paramagnetic label, enzyme label, or calorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, 35S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472-480; Shreve et al., (1986) *Magn. Reson. Med.* 3, 336-340; Wolf, G. L., (1984) *Physiol. Chem. Phys. Med. NMR* 16, 93-95; Wesbey et al., (1984) *Physiol. Chem. Phys. Med. NMR* 16, 145-155; Runge et al., (1984) *Invest. Radiol.* 19, 408-415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known and used by those of ordinary skill in the art. Typical techniques are described by Kennedy et al., (1976) *Clin. Chim. Acta* 70, 1-31; and Schurs et al., (1977) *Clin. Chim. Acta* 81, 1-40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting hepsin protein in a biological sample, which includes the steps of contacting the sample with the labeled antibody, e.g., radioactively tagged antibody specific for hepsin, and determining whether the antibody binds to a component of the sample. Antibodies to the hepsin protein can be used in an immunoassay to detect increased levels of hepsin protein expression in tissues suspected of neoplastic transformation. These same uses can be achieved with Northern blot assays and analyses.

As described herein, the invention provides a number of diagnostic advantages and uses. For example, the hepsin protein is useful in diagnosing cancer in different tissues since this protein is highly overexpressed in tumor cells. Antibodies (or antigen-binding fragments thereof) which bind to an epitope specific for hepsin are useful in a method of detecting hepsin protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for hepsin, and detecting the hepsin protein using standard immunoassay techniques such as an ELISA. Antibody binding to the biological sample indicates that the sample contains a component which specifically binds to an epitope within hepsin.

Likewise, a standard Northern blot assay can be used to ascertain the relative amounts of hepsin mRNA in a cell or tissue obtained from a patient suspected of having cancer, in accordance with conventional Northern hybridization techniques known to those of ordinary skill in the art. This Northern assay uses a hybridization probe, e.g., radiolabelled hepsin cDNA, either containing the full-length, single stranded DNA having a sequence complementary to SEQ ID No. 188, or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

The following examples are given for the purpose of illustrating various embodiments of the invention and are not meant to limit the present invention in any fashion:

Example 1

Amplification Of Serine Proteases Using Redundant and Specific Primers

Only cDNA preparations deemed free of genomic DNA were used for gene expression analysis. Redundant primers were prepared for serine proteases, metallo-proteases and cysteine protease. The primers were synthesized to consensus sequences of amino acid surrounding the catalytic triad for serine proteases, viz. histidine . . . aspartate . . . and serine. The sequences of both sense (histidine & aspartate) and antisense (aspartate and serine) redundant primers are shown in Table 2.

Several protease entities were identified and subcloned from PCR amplification of cDNA derived from serous cystadenocarcinomas. Therefore, the proteases described herein are reflective of surface activities for this type of carcinoma, the most common form of ovarian cancer. Applicant also shows PCR amplification bands of similar base pair size unique to the mucinous tumor type and the clear cell type. About 20-25% of ovarian cancers are classified as either mucinous, clear cell, or endometrioid.

To determine the identity of the PCR products, all the appropriate bands were ligated into Promega T-vector plasmid and the ligation product was used to transform JM109 cells (Promega) grown on selective media. After selection and culturing of individual colonies, plasmid DNA was isolated by means of the WIZARD MINIPREP™ DNA purification system (Promega). Inserts were sequenced using a Prism Ready Reaction Dydeoxy Terminators cycle sequencing kit (Applied Biosystems). Residual dye terminators were removed from the completed sequencing reaction using a CENTRISEP SPIN™ column (Princeton Separation), and samples were loaded into an Applied Biosystems Model 373A DNA sequencing system. The results of subcloning and sequencing for the serine protease primers are summarized in Table 3.

TABLE 2

| PCR Primers | 5'→3' | SEQ ID No. |
|---|---|---|
| Redundant Primers: | | |
| Serine Protease (histidine) = S1 | tgggtigtiacigcigcica(ct)tg | 1 |
| Serine Protease (aspartic acid) = AS1 | a(ag)ia(ag)igciatitcitticc | 2 |
| Serine Protease (serine) = AS11 | a(ag)iggiccicci(cg)(ta)(ag)tcicc | 3 |
| Cysteine Protease-sense | ca(ag)ggica(ag)tg(ct)ggi(ta)(cg)itg(ct)tgg | 4 |
| Cysteine Protease-antisense | taiccicc(ag)tt(ag)caicc(ct)tc | 5 |
| Metallo Protease-sense | cci(ac)gitg(tc)ggi(ga)(ta)icciga | 6 |
| Metallo Protease-antisense | tt(ag)tgicciai(ct)tc(ag)tg | 7 |
| Specific Primers: | | |
| Serine Protease (hepsin) = sense | tgtcccgatggcgagtgttt | 8 |
| Serine Protease (hepsin) = antisense | cctgttggccatagtactgc | 9 |
| Serine Protease (SCCE) = sense | agatgaatgagtacaccgtg | 10 |
| Serine Protease (SCCE) = antisense | ccagtaagtccttgtaaacc | 11 |
| Serine Protease (Comp B) = sense | aagggacacgagagctgtat | 12 |
| Serine Protease (Comp B) = antisense | aagtggtagttggaggaagc | 13 |
| Serine Protease (Protease M) = sense | ctgtgatccaccctgactat | 20 |
| Serine Protease (Protease M) = antisense | caggtggatgtatgcacact | 21 |
| Serine Protease (TADG12) = sense (Ser10-s) | gcgcactgtgtttatgagat | 22 |
| Serine Protease (TADG12) = antisense (Ser10-as) | ctctttggcttgtacttgct | 23 |
| Serine Protease (TADG13) = sense | tgagggacatcattatgcac | 24 |
| Serine Protease (TADG13) = antisense | caagttttccccataattgg | 25 |
| Serine Protease (TADG14) = sense | acagtacgcctgggagacca | 26 |
| Serine Protease (TADG14) = antisense | ctgagacggtgcaattctgg | 27 |
| Cysteine Protease (Cath-L) = sense | attggagagagaaaggctac | 14 |
| Cysteine Protease (Cath-L) = antisense | cttgggattgtacttacagg | 15 |
| Metallo Protease (PUMP1) = sense | cttccaaagtggtcacctac | 16 |
| Metallo Protease (PUMP1) = antisense | ctagactgctaccatccgtc | 17 |

TABLE 3

Serine protease candidates

| Subclone | Primer Set | Gene Candidate |
|---|---|---|
| 1 | His-Ser | Hepsin |
| 2 | His-Ser | SCCE |
| 3 | His-Ser | Compliment B |
| 4 | His-Asp | Cofactor 1 |
| 5 | His-Asp | TADG-12* |
| 6 | His-Ser | TADG-13* |
| 7 | His-Ser | TADG-14* |
| 8 | His-Ser | Protease M |
| 9 | His-Ser | TADG-15* |

*indicates novel proteases

Sequencing of the PCR products derived from tumor cDNA confirms the potential candidacy of these genes. The three novel genes all have conserved residues within the catalytic triad sequence consistent with their membership in the serine protease family.

Applicant compared the PCR products amplified from normal and carcinoma cDNAs using sense-histidine and antisense-aspartate as well as sense-histidine and antisense-serine. The anticipated PCR products of approximately 200 bp and 500 bp for those pairs of primers were observed (aspartate is approximately 50-70 amino acids downstream from histidine, and serine is about 100-150 amino acids toward the carboxy end from histidine).

FIG. 1 shows a comparison of PCR products derived from normal and carcinoma cDNA as shown by staining in an agarose gel. Two distinct bands in Lane 2 were present in the primer pair sense-His/antisense ASP (AS1) and multiple bands of about 500 bp are noted in the carcinoma lane for the sense-His/antisense-Ser (AS2) primer pairs in Lane 4.

Example 2

Northern Blots Analysis

Significant information can be obtained by examining the expression of these candidate genes by Northern blot. Analysis of normal adult multi-tissue blots offers the opportunity to identify normal tissues which may express the protease. Ultimately, if strategies for inhibition of proteases for therapeutic intervention are to be developed, it is essential to appreciate the expression of these genes in normal tissues.

Significant information is expected from Northern blot analysis of fetal tissue. Genes overexpressed in carcinomas are often highly expressed in organogenesis. As indicated, the hepsin gene cloned from hepatoma cells and overexpressed in ovarian carcinoma is overtly expressed in fetal liver. Hepsin gene expression was also detected in fetal kidney, and therefore, could be a candidate for expression in renal carcinomas.

Northern panels for examining expression of genes in a multi-tissue normal adult as well as fetal tissue are commercially available (CLONTECH). Such evaluation tools are not only important to confirm the overexpression of individual transcripts in tumor versus normal tissues, but also provides the opportunity to confirm transcript size, and to determine if alternate splicing or other transcript alteration may occur in ovarian carcinoma.

Northern blot analysis was performed as follows: 10 μg of mRNA was loaded onto a 1% formaldehyde-agarose gel, electrophoresed and blotted onto a HyBond-N+™ nylon membrane (Amersham). $^{32}$P-labeled cDNA probes were made using Prime-a-Gene Labeling System™ (Promega). The PCR products amplified by specific primers were used as probes. Blots were prehybridized for 30 min and then hybridized for 60 min at 68° C. with $^{32}$P-labeled cDNA probe in ExpressHyb™ Hybridization Solution (CLONTECH). Control hybridization to determine relative gel loading was accomplished using the β-tubulin probe.

Normal human tissues including spleen, thymus, prostate, testis, ovary, small intestine, colon, peripheral blood leukocyte, heart, brain, placenta, lung, liver, skeletal muscle, kidney, pancreas and normal human fetal tissues (Human Multiple Tissue Northern Blot; CLONTECH) were all examined using the same hybridization procedure.

Figure 2:
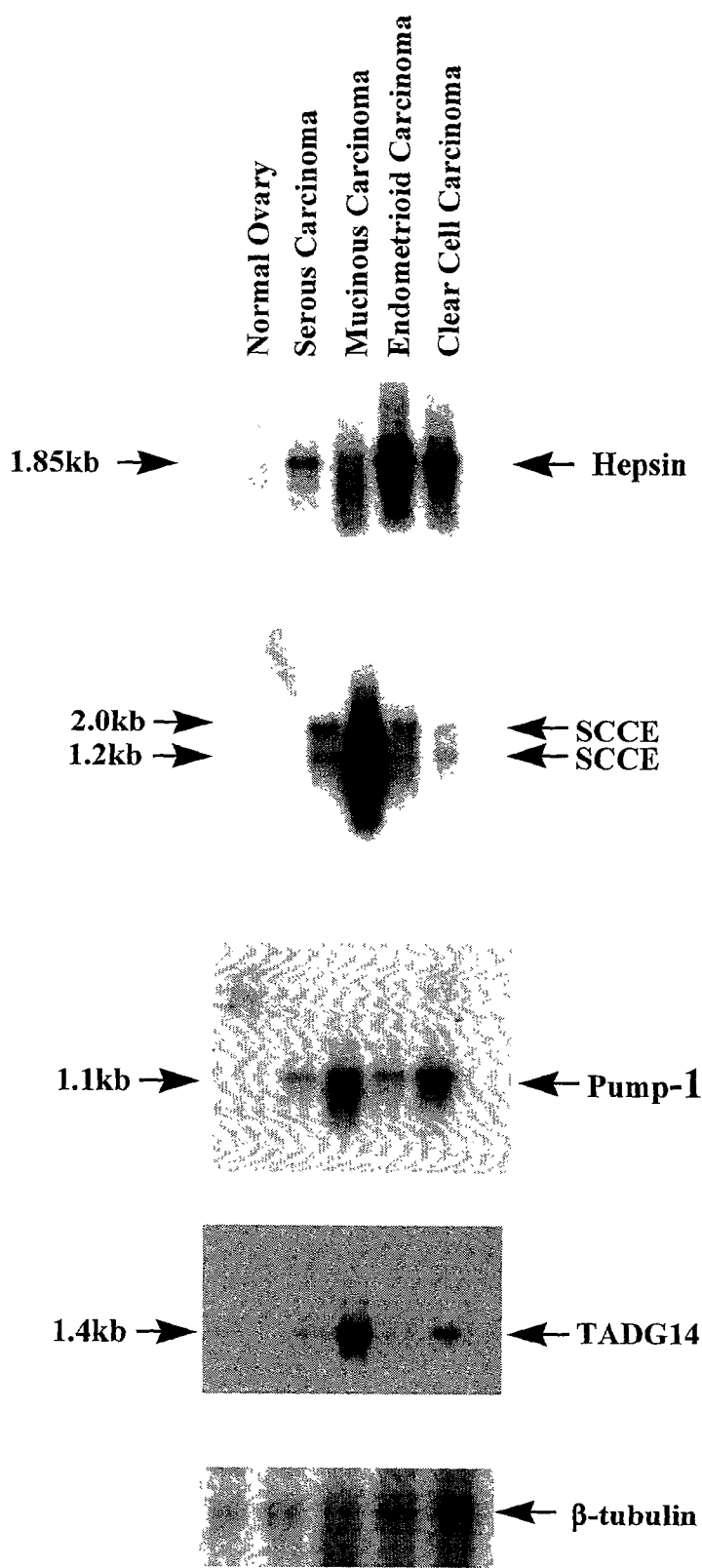
FIG. 2 shows Northern blot analysis of ovarian tumors using hepsin, SCCE, PUMP-1, TADG-14 and β-tubulin probes.

Experiments comparing PCR amplification in normal ovary and ovarian carcinoma suggested overexpression and/or alteration in mRNA transcript in tumor tissues. Northern blot analysis of TADG-14 confirms a transcript size of 1.4 kb and data indicate overexpression in ovarian carcinoma (FIG. 2). Isolation and purification using both PCR and a specific 250 bp PCR product to screen positive plaques yielded a 1.2 kb clone of TADG-14. Other proteases were amplified by the same method using the appropriate primers from Table 2.

Example 3

PCR Products Corresponding to Serine, Cysteine and Metallo-Proteases

Figure 3:
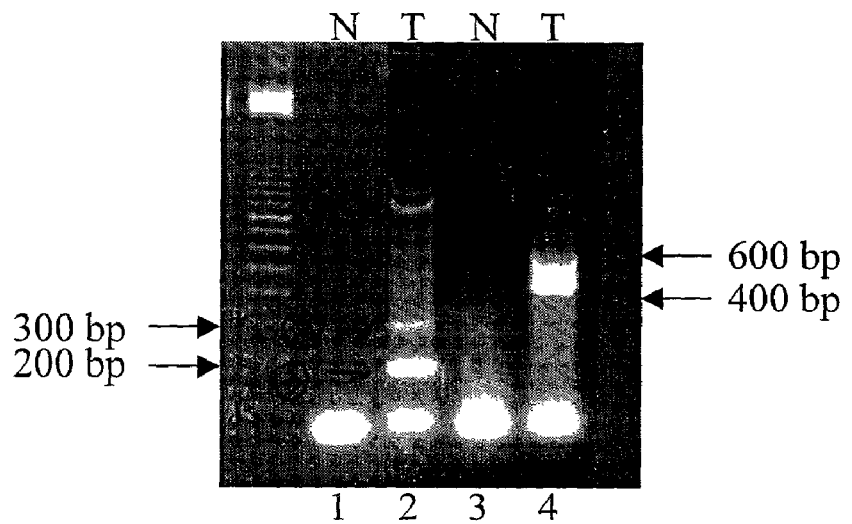
FIG. 3 shows amplification with serine protease redundant primers: histidine sense (S1) with aspartic acid antisense (AS1), using normal cDNA (Lane 1) and tumor cDNA (Lane 2); and histidine sense (S1) with serine antisense (AS2), using normal cDNA (Lane 3) and tumor cDNA (Lane 4).
Figure 4:
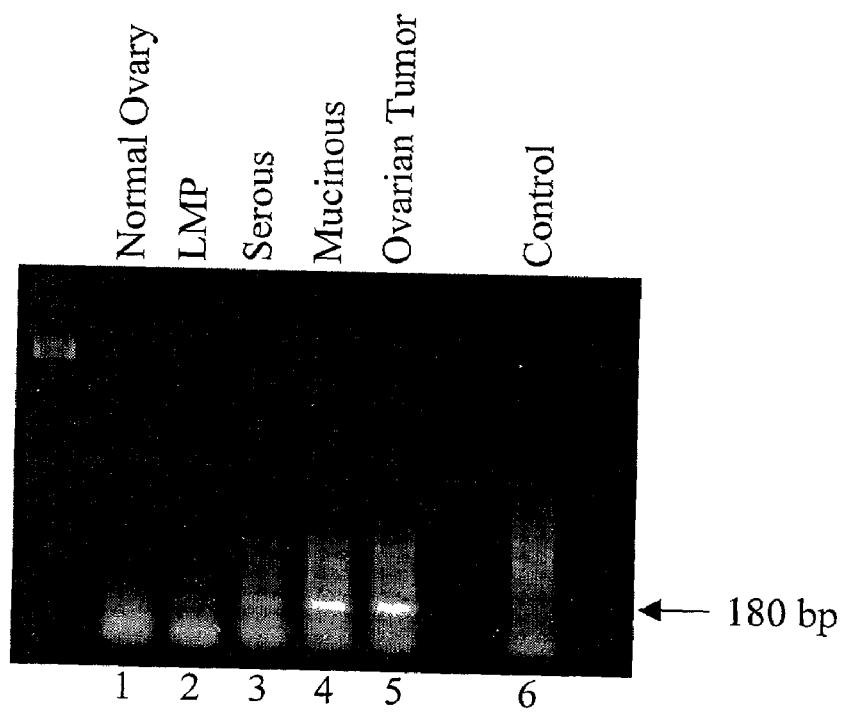
FIG. 4 shows amplification with cysteine protease redundant primers. Normal (Lane 1), low malignant potential (Lane 2), serious carcinoma (Lane 3), mucinous carcinoma (Lane 4), and clear cell carcinoma (Lane 5).
Figure 5:
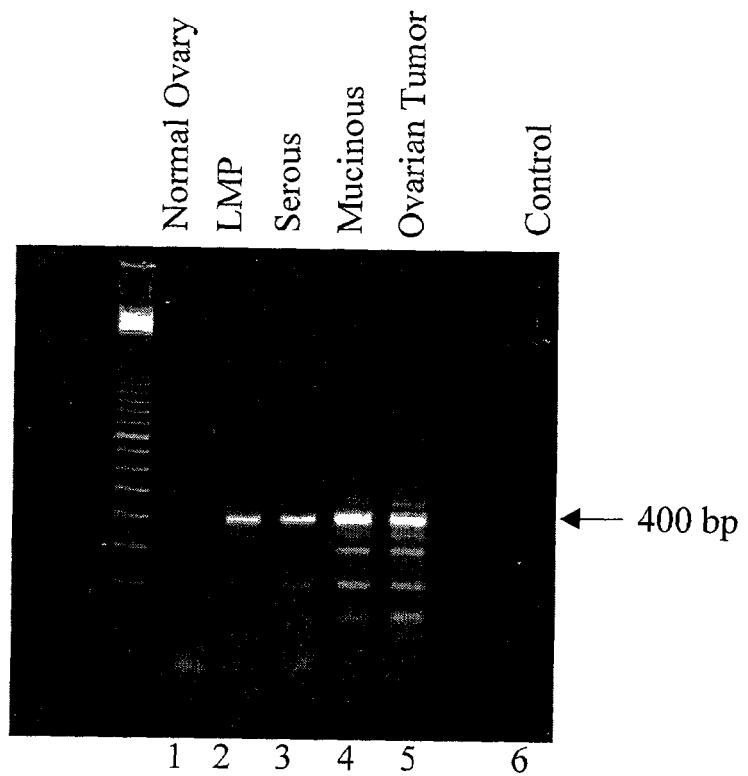
FIG. 5 shows amplification with metallo-protease redundant primers. Normal (Lane 1), low malignant potential (Lane 2), serious carcinoma (Lane 3), mucinous carcinoma (Lane 4), and clear cell carcinoma (Lane 5).

Based on their unique expression in either low malignant potential tumors or carcinomas, PCR-amplified cDNA products were cloned and sequenced and the appropriate gene identified based upon nucleotide and amino acid sequences stored in the GCG and EST databases. FIGS. 3, 4 & 5 show the PCR product displays comparing normal and carcinomatous tissues using redundant primers for serine proteases (FIG. 3), for cysteine proteases (FIG. 4) and for metallo-proteases (FIG. 5). Note the differential expression in the carcinoma tissues versus the normal tissues. The proteases were identified using redundant cDNA primers (see Table 2) directed towards conserved sequences that are associated with intrinsic enzyme activity (for serine proteases, cysteine proteases and metallo-proteases) by comparing mRNA expression in normal, low malignant potential and overt ovarian carcinoma tissues according to Sakanari et al. *[Biochemistry* 86, 4863-4867 (1989)].

Example 4

Serine Proteases

For the serine protease group, using the histidine domain primer sense, S1, in combination with antisense primer AS2, the following proteases were identified:

(a) Hepsin, a trypsin-like serine protease cloned from hepatoma cells shown to be a cell surface protease essential for the growth of hepatoma cells in culture and highly expressed in hepatoma tumor cells (FIG. 3, Lane 4);

(b) Complement factor B protease (human factor IX), a protease involved in the coagulation cascade and associated with the production and accumulation of fibrin split products associated with tumor cells (FIG. 3, Lane 4). Compliment factor B belongs in the family of coagulation factors X (Christmas factor). As part of the intrinsic pathway, compliment factor B catalyzes the proteolytic activation of coagulation factor X in the presence of $Ca^{2+}$ phospholipid and factor VIIIa e5; and (c) A stratum corneum chymotryptic enzyme (SCCE) serine protease involved in desquarnation of skin cells from the human stratum corneum (FIG. 3, Lane 4). SCCE is expressed in keratinocytes of the epidermis and functions to degrade the cohesive structures in the cornified layer to allow continuous skin surface shedding.

Example 5

Cysteine Proteases

In the cysteine protease group, using redundant sense and anti-sense primers for cysteine proteases, one unique PCR product was identified by overexpression in ovarian carcinoma when compared to normal ovarian tissue (FIG. 4, Lanes 3-5). Cloning and sequencing this PCR product identified a sequence of Cathepsin L, which is a lysomal cysteine protease whose expression and secretion is induced by malignant transformation, growth factors and tumor promoters. Many human tumors (including ovarian) express high levels of Cathepsin L. Cathepsin L cysteine protease belongs in the stromolysin family and has potent elastase and collagenase activities. Published data indicates increased levels in the serum of patients with mucinous cystadenocarcinoma of the ovary. It has not heretofore been shown to be expressed in other ovarian tumors.

Example 6

Metallo-Proteases

Using redundant sense and anti-sense primers for the metallo-protease group, one unique PCR product was detected in the tumor tissue which was absent in normal ovarian tissue (FIG. 5, Lanes 2-5). Subcloning and sequencing this product indicates it has complete homology in the appropriate region with the so-called PUMP-1 (MMP-7) gene. This zinc-binding metallo-protease is expressed as a proenzyme with a signal sequence and is active in gelatin and collagenase digestion. PUMP-1 has also been shown to be induced and overexpressed in 9 of 10 colorectal carcinomas compared to normal colon tissue, suggesting a role for this substrate in the progression of this disease.

Example 7

Expression of Hepsin

The mRNA overexpression of hepsin was detected and determined using quantitative PCR. Quantitative PCR was performed generally according to the method of Noonan et al. *[Proc. Natl. Acad. Sci. USA,* 87:7160-7164 (1990)]. The following oligonucleotide primers were used: hepsin forward 5'-TGTCCCGATGGCGAGTGTTT-3' (SEQ ID No. 8), and hepsin reverse 5'-CCTGTTGGCCATAGTACTGC-3' (SEQ ID No. 9); β-tubulin forward 5'-TGCATTGACAAC-GAGGC-3' (SEQ ID No. 18), and β-tubulin reverse 5'-CT-GTCTTGA CATTGTTG-3' (SEQ ID No. 19).

β-tubulin was utilized as an internal control. The predicted sizes of the amplified genes were 282 bp for hepsin and 454 bp for β-tubulin. The primer sequences used in this study were designed according to the cDNA sequences described by Leytus et al. *[Biochemistry,* 27, 1067-1074 (1988)] for hepsin, and Hall et al. *[Mol. Cell. Biol.,* 3, 854-862 (1983)] for β-tubulin.

The PCR reaction mixture consisted of cDNA derived from 50 ng of mRNA converted by conventional techniques, 5 pmol of sense and antisense primers for both the hepsin gene and the β-tubulin gene, 200 μmol of dNTPs, 5 μCi of $\alpha$-$^{32}$PdCTP and 0.25 units of Taq DNA polymerase with reaction buffer (Promega) in a final volume of 25 μl. The target sequences were amplified in parallel with the β-tubulin gene. Thirty cycles of PCR were carried out in a Thermal Cycler (Perkin-Elmer Cetus). Each cycle of PCR included 30 sec of denaturation at 95° C., 30 sec of annealing at 63° C. and 30 sec of extension at 72° C. The PCR products were separated on 2% agarose gels and the radioactivity of each PCR product was determined by using a PhosphorImager™ (Molecular Dynamics). Student's t test was used for comparison of mean values.

Hepsin is a trypsin-like serine protease cloned from hepatoma cells. Hepsin is an extracellular protease (the enzyme includes a secretion signal sequence) which is anchored in the plasma membrane by its amino terminal domain, thereby exposing its catalytic domain to the extracellular matrix. Hepsin has also been shown to be expressed in breast cancer cell lines and peripheral nerve cells. Hepsin has never before been associated with ovarian carcinoma. Specific primers for the hepsin gene were synthesized and the expression of hepsin examined using Northern blots of fetal tissue and ovarian tissue (both normal and ovarian carcinoma).

Figures 10A, 10B, 10C:
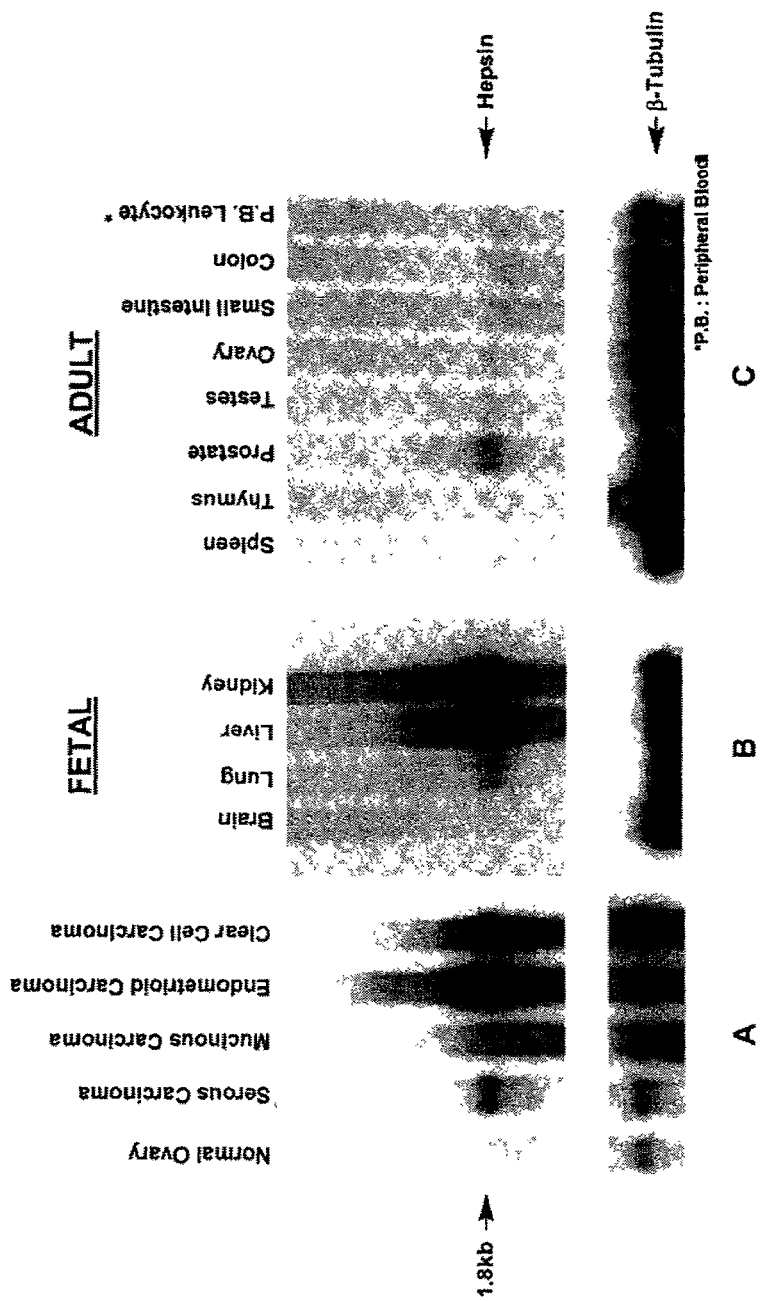
FIG. 10A shows Northern blot analysis of hepsin expression in normal ovary and ovarian carcinomas. Lane 1, normal ovary (case 10); lane 2, serous carcinoma (case 35); lane 3, mucinous carcinoma (case 48); lane 4, endometrioid carcinoma (case 51); and lane 5, clear cell carcinoma (case 54). In cases 35, 51 and 54, more than a 10-fold increase in the hepsin 1.8 kb transcript abundance was observed.
FIG. 10B shows Northern blot analysis of hepsin in normal human fetal.
FIG. 10C shows Northern blot analysis of hepsin in adult tissues. Significant overexpression of the hepsin transcript is noted in both fetal liver and fetal kidney. Notably, hepsin overexpression is not observed in normal adult tissue. Slight expression above the background level is observed in the adult prostate.

FIG. 10A shows that hepsin was expressed in ovarian carcinomas of different histologic types, but not in normal ovary. FIG. 10B shows that hepsin was expressed in fetal liver and fetal kidney as anticipated, but at very low levels or not at all in fetal brain and lung. FIG. 10C shows that hepsin overexpression is not observed in normal adult tissue. Slight expression above the background level is observed in the adult prostate. The mRNA identified in both Northern blots was the appropriate size for the hepsin transcript. The expression of hepsin was examined in 10 normal ovaries and 44 ovarian tumors using specific primers to β-tubulin and hepsin in a quantitative PCR assay, and found it to be linear over 35 cycles. Expression is presented as the ratio of $^{32}$P-hepsin band to the internal control, the $^{32}$P-β-tubulin band.

Figure 11A:
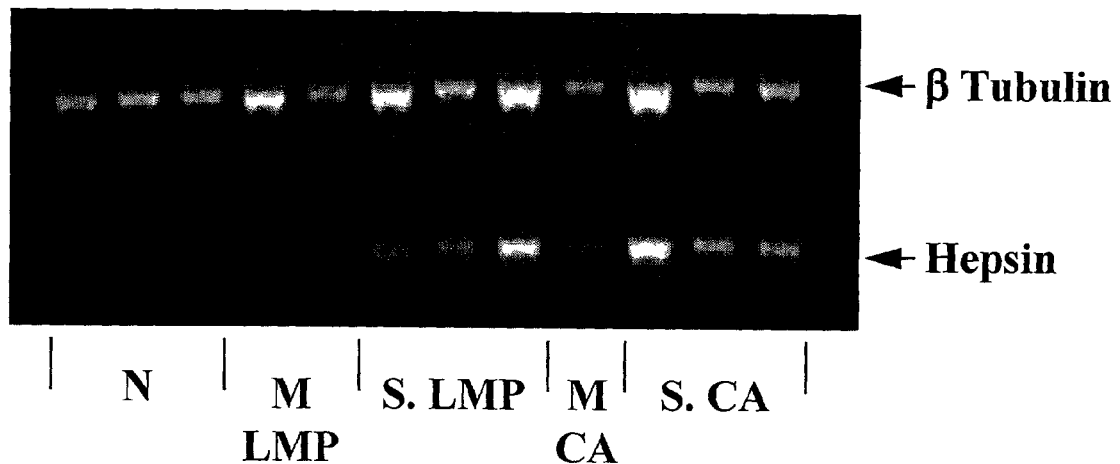
FIG. 11A shows hepsin expression in normal (N), mucinous (M) and serous (S) low malignant potential (LMP) tumors and carcinomas (CA). β-tubulin was used as an internal control.
Figure 11B:
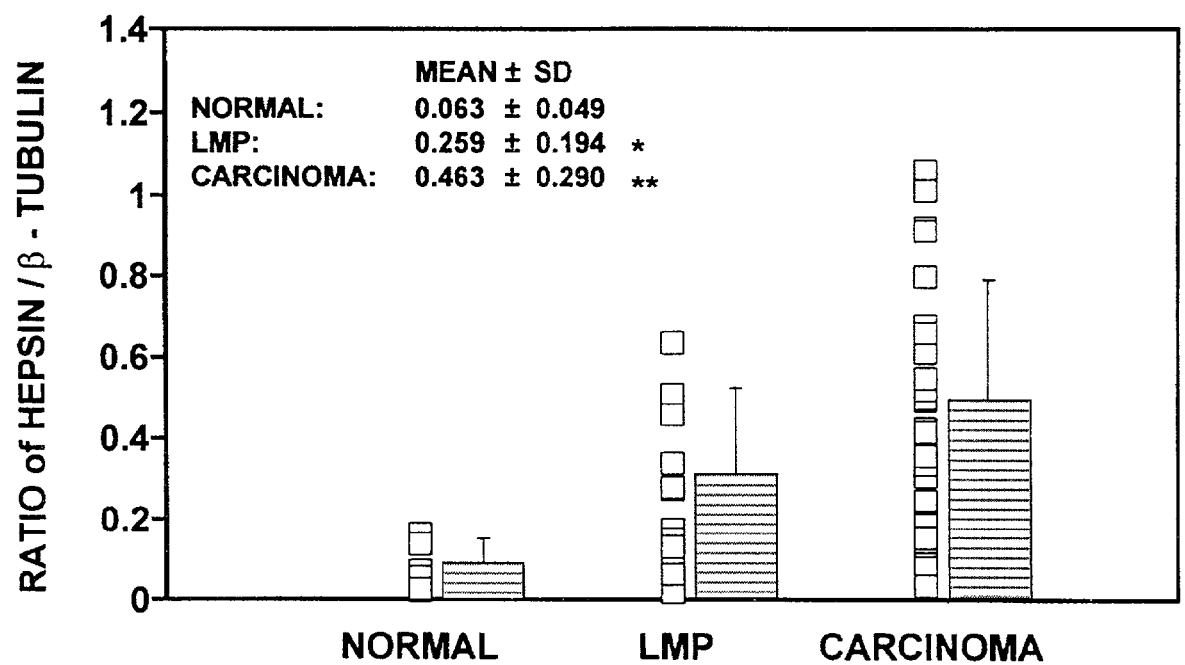
FIG. 11B shows the ratio of hepsin:β-tubulin expression in normal ovary, LMP tumor, and ovarian carcinoma. Hepsin mRNA expression levels were significantly elevated in LMP tumors, ($p<0.005$) and carcinomas ($p<0.0001$) compared to levels in normal ovary. All 10 cases of normal ovaries showed a relatively low level of hepsin mRNA expression.

Hepsin expression was investigated in normal (N), mucinous (M) and serous (S) low malignant potential (LMP) tumors and carcinomas (CA). FIG. 11A shows quantitative PCR of hepsin and internal control β-tubulin. FIG. 11B shows the ratio of hepsin:β-tubulin expression in normal ovary, LMP tumor, and ovarian carcinoma. It was observed that Hepsin mRNA expression levels were significantly elevated in LMP tumors, (p<0.005) and carcinomas (p<0.0001) compared to levels in normal ovary. All 10 cases of normal ovaries showed a relatively low level of hepsin mRNA expression.

Hepsin mRNA is highly overexpressed in most histopathologic types of ovarian carcinomas including some low malignant potential tumors (see FIGS. 11A & 11B). Most noticeably, hepsin is highly expressed in serous, endometrioid and clear cell tumors tested. It is highly expressed in some mucinous tumors, but it is not overexpressed in the majority of such tumors.

A tumor tissue bank of fresh frozen tissue of ovarian carcinomas as shown in Table 4 was used for evaluation. Approximately 100 normal ovaries removed for medical reasons other than malignancy were obtained from surgery and were available as controls.

From the tumor bank, approximately 100 carcinomas were evaluated encompassing most histological sub-types of ovarian carcinoma, including borderline or low-malignant potential tumors and overt carcinomas. The approach included using mRNA prepared from fresh frozen tissue (both normal and malignant) to compare expression of genes in normal, low malignant potential tumors and overt carcinomas. The cDNA prepared from polyA+ mRNA was deemed to be genomic DNA-free by checking all preparations with primers that encompassed a known intron-exon splice site using both β-tubulin and p53 primers.

TABLE 4

| Ovarian cancer tissue bank | | | | |
|---|---|---|---|---|
| | Total | Stage I/11 | Stage III/IV | No Stage |
| Serous | | | | |
| Malignant | 166 | 15 | 140 | 8 |
| LMP | 16 | 9 | 7 | 0 |
| Benign | 12 | 0 | 0 | 12 |
| Mucinous | | | | |
| Malignant | 26 | 6 | 14 | 6 |
| LMP | 28 | 25 | 3 | 0 |
| Benign | 3 | 0 | 0 | 3 |
| Endometrioid | | | | |
| Malignant | 38 | 17 | 21 | 0 |
| LMP | 2 | 2 | 0 | 0 |
| Benign | 0 | 0 | 0 | 0 |
| Other* | | | | |
| Malignant | 61 | 23 | 29 | 9 |
| LMP | 0 | 0 | 0 | 0 |
| Benign | 5 | 0 | 0 | 5 |

*Other category includes the following tumor types: Brenner's tumor, thecoma, teratoma, fibrothecoma, fibroma, granulosa cell, clear cell, germ cell, mixed mullerian, stromal, undifferentiated, and dysgerminoma.

Figure 6:
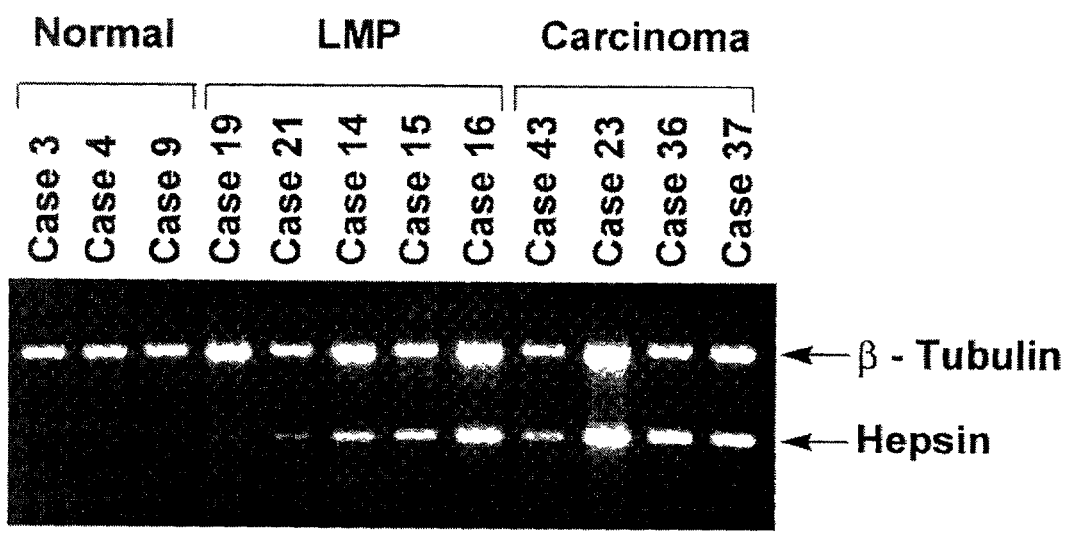
FIG. 6 shows amplification with specific primers directed towards the serine protease, hepsin. Expression in normal (Lanes 1-3), low malignant potential tumors (Lanes 4-8), and ovarian carcinomas (Lanes 9-12).
Figure 7:
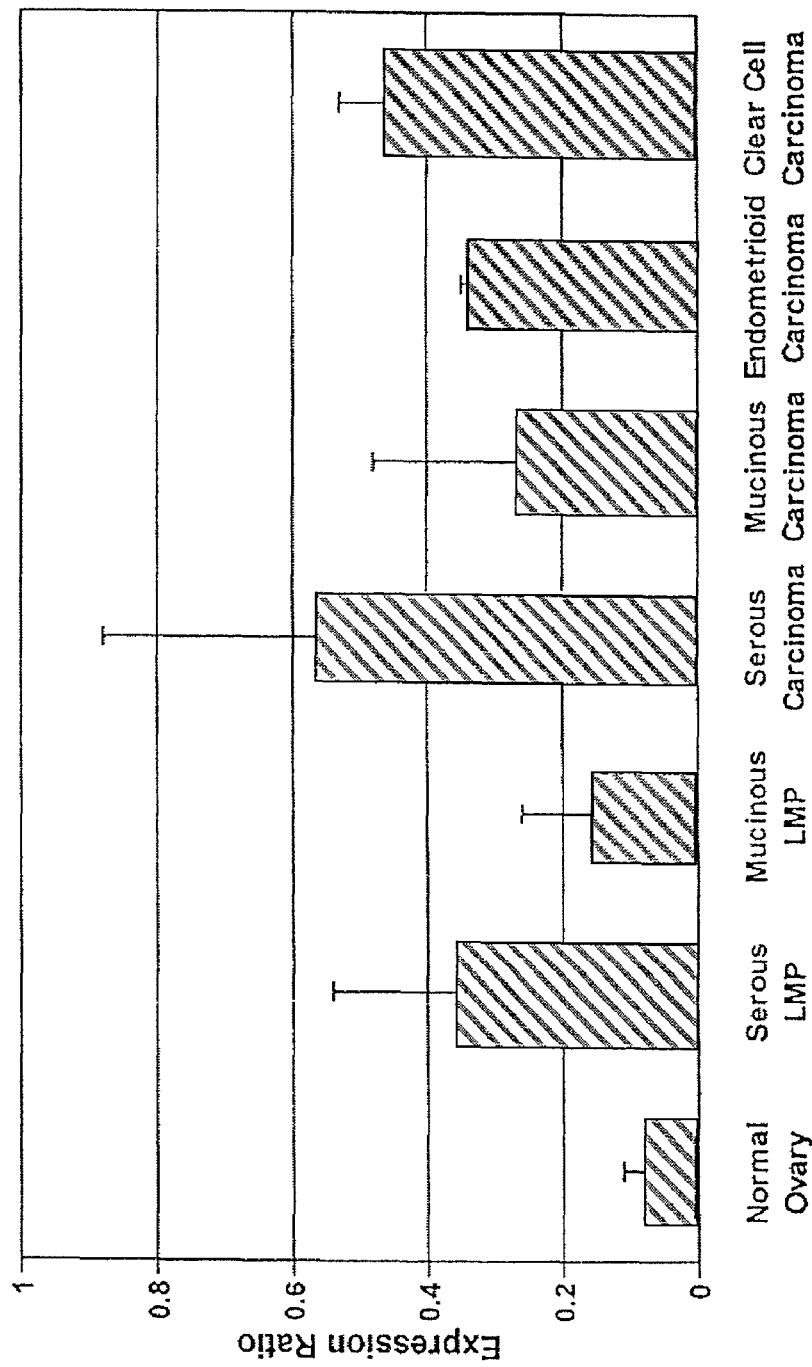
FIG. 7 shows hepsin expression levels in normal, low malignant potential tumors, and ovarian carcinomas. S=serious, M=mucinous, LMP=low malignant potential.

The expression of the serine protease hepsin gene in 8 normal, 11 low malignant potential tumors, and 14 carcinoma (both mucinous and serous type) by quantitative PCR using hepsin-specific primers (see Table 2) was determined (primers directed toward the β-tubulin message were used as an internal standard) (Table 5). These data confirm the overexpression of the hepsin surface protease gene in ovarian carcinoma, including both low malignant potential tumors and overt carcinoma. Expression of hepsin is increased over normal levels in low malignant potential tumors, and high stage tumors (Stage III) of this group have higher expression of hepsin when compared to low stage tumors (Stage 1) (Table 6). In overt carcinoma, serous tumors exhibit the highest levels of hepsin expression, while mucinous tumors express levels of hepsin comparable with the high stage low malignant potential group (FIGS. 6 & 7).

TABLE 5

| Case | Histological type[a] | Stage/Grade | LN[b] | mRNA expression of hepsin[c] |
|---|---|---|---|---|
| 1 | normal ovary | | | n |
| 2 | normal ovary | | | n |
| 3 | normal ovary | | | n |
| 4 | normal ovary | | | n |
| 5 | normal ovary | | | n |
| 6 | normal ovary | | | n |
| 7 | normal ovary | | | n |
| 8 | normal ovary | | | n |
| 9 | normal ovary | | | n |
| 10 | normal ovary | | | n |
| 11 | S adenoma (LMP) | 1/1 | N | 4+ |
| 12 | S adenoma (LMP) | 1/1 | NE | 4+ |
| 13 | S adenoma (LMP) | 1/1 | NE | n |
| 14 | S adenoma (LMP) | 1/1 | N | 2+ |
| 15 | S adenoma (LMP) | 3/1 | P | 4+ |
| 16 | S adenoma (LMP) | 3/1 | P | 4+ |
| 17 | S adenoma (LMP) | 3/1 | P | 4+ |
| 18 | M adenoma (LMP) | 1/1 | NE | 4+ |
| 19 | M adenoma (LMP) | 1/1 | N | n |
| 20 | M adenoma (LMP) | 1/1 | N | n |
| 21 | M adenoma (LMP) | 1/1 | N | n |
| 22 | M adenoma (LMP) | 1/1 | NE | n |
| 23 | S carcinoma | 1/2 | N | 4+ |
| 24 | S carcinoma | 1/3 | N | 4+ |

TABLE 5-continued

| Case | Histological type[a] | Stage/Grade | LN[b] | mRNA expression of hepsin[c] |
|---|---|---|---|---|
| 25 | S carcinoma | 3/1 | NE | 2+ |
| 26 | S carcinoma | 3/2 | NE | 4+ |
| 27 | S carcinoma | 3/2 | P | 4+ |
| 28 | S carcinoma | 3/2 | NE | 2+ |
| 29 | S carcinoma | 3/3 | NE | 2+ |
| 30 | S carcinoma | 3/3 | NE | 4+ |
| 31 | S carcinoma | 3/3 | NE | 4+ |
| 32 | S carcinoma | 3/3 | NE | 4+ |
| 33 | S carcinoma | 3/3 | N | 4+ |
| 34 | S carcinoma | 3/3 | NE | n |
| 35 | S carcinoma | 3/3 | NE | 4+ |
| 36 | S carcinoma | 3/3 | NE | 4+ |
| 37 | S carcinoma | 3/3 | NE | 4+ |
| 38 | S carcinoma | 3/3 | N | 4+ |
| 39 | S carcinoma | 3/2 | NE | 2+ |
| 40 | S carcinoma | 3/3 | NE | 4+ |
| 41 | S carcinoma | 3/2 | NE | 4+ |
| 42 | M carcinoma | 1/2 | N | n |
| 43 | M carcinoma | 2/2 | NE | 4+ |
| 44 | M carcinoma | 2/2 | N | 4+ |
| 45 | M carcinoma | 3/1 | NE | n |
| 46 | M carcinoma | 3/2 | NE | 4+ |
| 47 | M carcinoma | 3/2 | NE | n |
| 48 | M carcinoma | 3/3 | NE | n |
| 49 | E carcinoma | 2/3 | N | 4+ |
| 50 | E carcinoma | 3/2 | NE | 4+ |
| 51 | E carcinoma | 3/3 | NE | 4+ |
| 52 | C carcinoma | 1/3 | N | 4+ |
| 53 | C carcinoma | 1/1 | N | 4+ |
| 54 | C carcinoma | 3/2 | P | 4+ |

[a]S, serous; M, mucinous; E, endometrioid; C, clear cell;
[b]LN, lymph node metastasis; P, positive; NE, not examined;
[c]n, normal range = mean ±2SD; 2+, mean ±2SD to ±4SD; 4+, mean ±4SD or greater.

TABLE 6

Overexpression of hepsin in normal ovaries amd ovarian tumors

| Type | N | Hepsin Overexpression | Ratio of Hepsin to β-tubulin |
|---|---|---|---|
| Normal | 10 | 0 (0%) | 0.06 ± 0.05 |
| LMP | 12 | 7 (58.3%) | 0.26 ± 0.19 |
| Serous | 7 | 6 (85.7%) | 0.34 ± 0.20 |
| Mucinous | 5 | 1 (20.0%) | 0.14 ± 0.12 |
| Carcinomous | 32 | 27 (84.4%) | 0.46 ± 0.29 |
| Serous | 19 | 18 (94.7%) | 0.56 ± 0.32 |
| Mucinous | 7 | 3 (42.9%) | 0.26 ± 0.22 |
| Endometrioid | 3 | 3 (100%) | 0.34 ± 0.01 |
| Clear Cell | 3 | 3 (100%) | 0.45 ± 0.08 |

Example 8

Expression of SCCE and PUMP-1

Figure 8:
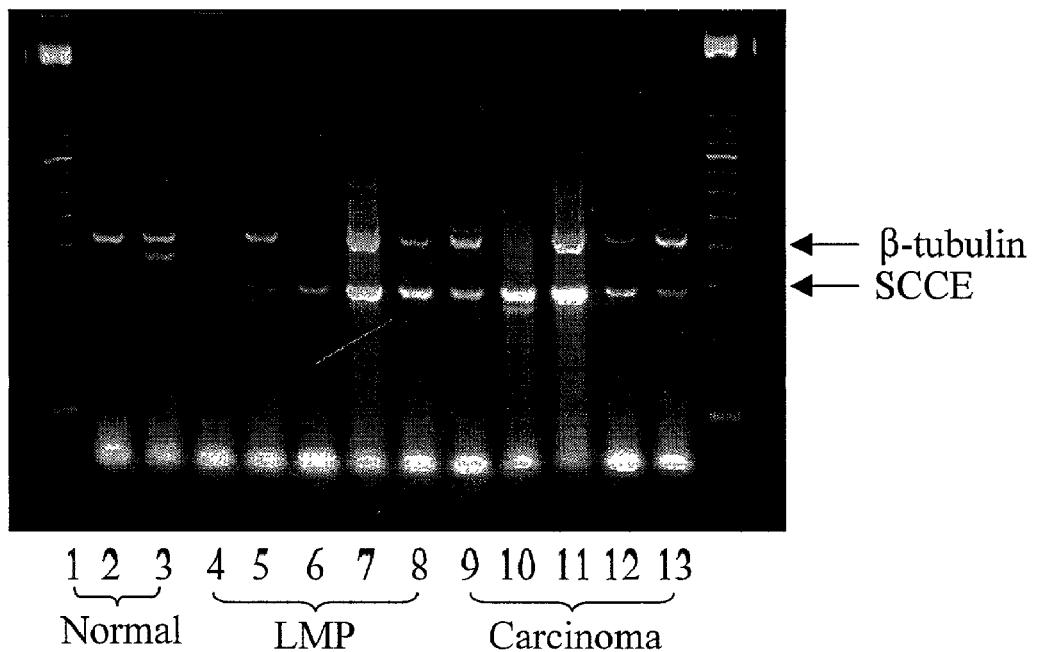
FIG. 8 shows serine protease stratum corneum chymotrypsin enzyme (SCCE) expression in normal, low malignant potential tumors, and ovarian carcinomas.
Figure 9:
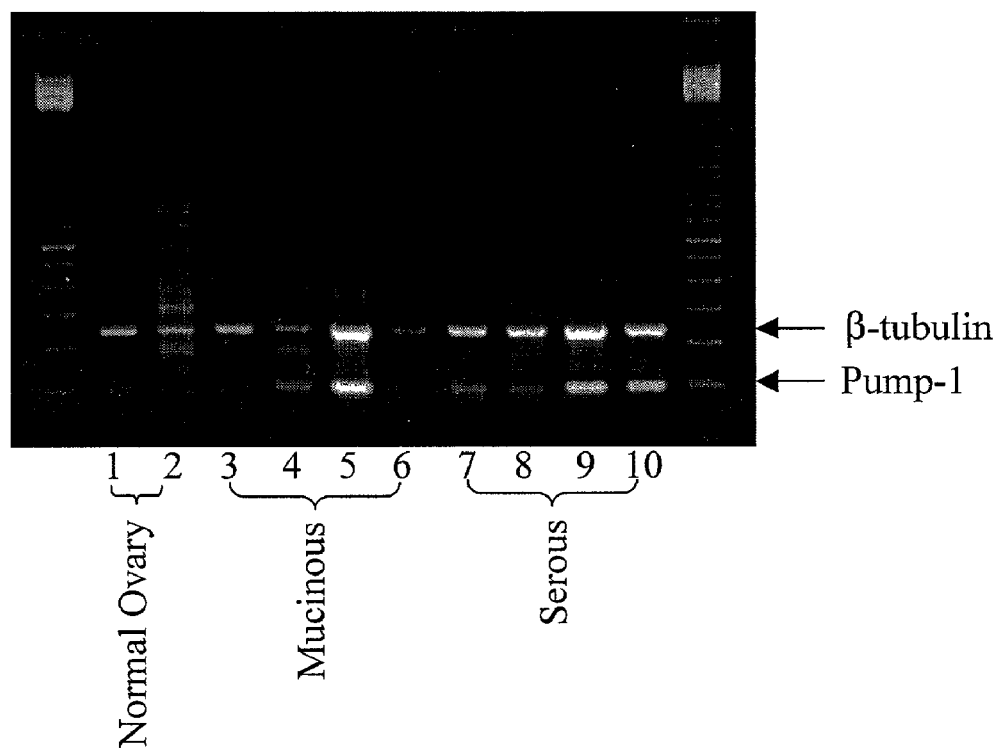
FIG. 9 shows metallo-protease PUMP-1 (MMP-7) gene expression in normal (lanes 1-2) and ovarian carcinomas tissue (Lanes 3-10).

Studies using both SCCE-specific primers (FIG. 8) and PUMP-specific primers (FIG. 9) indicate overexpression of these proteases in ovarian carcinomas.

Example 9

Summary of Proteases Detected Herein

Most of the proteases described herein were identified from the sense-His/antisense-Ser primer pair, yielding a 500 bp PCR product (FIG. 1, Lane 4). Some of the enzymes are familiar, a short summary of each follows.

Stratum Corneum Chymotrypsin Enzyme (SCCE)

The PCR product identified was the catalytic domain of the sense-His/antisense-Ser of the stratum corneum chymotrypsin enzyme. This extracellular protease was cloned, sequenced and shown to be expressed on the surface of keratinocytes in the epidermis. Stratum corneum chymotrypsin enzyme is a chymotrypsin-like serine protease whose function is suggested to be in the catalytic degradation of intercellular cohesive structures in the stratum corneum layer of the skin. This degradation allows continuous shedding (desquamation) of cells from the skin surface. The subcellular localization of stratum corneum chymotrypsin enzyme is in the upper granular layer in the stratum corneum of normal non-palmoplantar skin and in the cohesive parts of hypertrophic plantar stratum corneum. Stratum corneum chymotrypsin enzyme is exclusively associated with the stratum corneum and has not so far been shown to be expressed in any carcinomatous tissues.

Figure 12A:
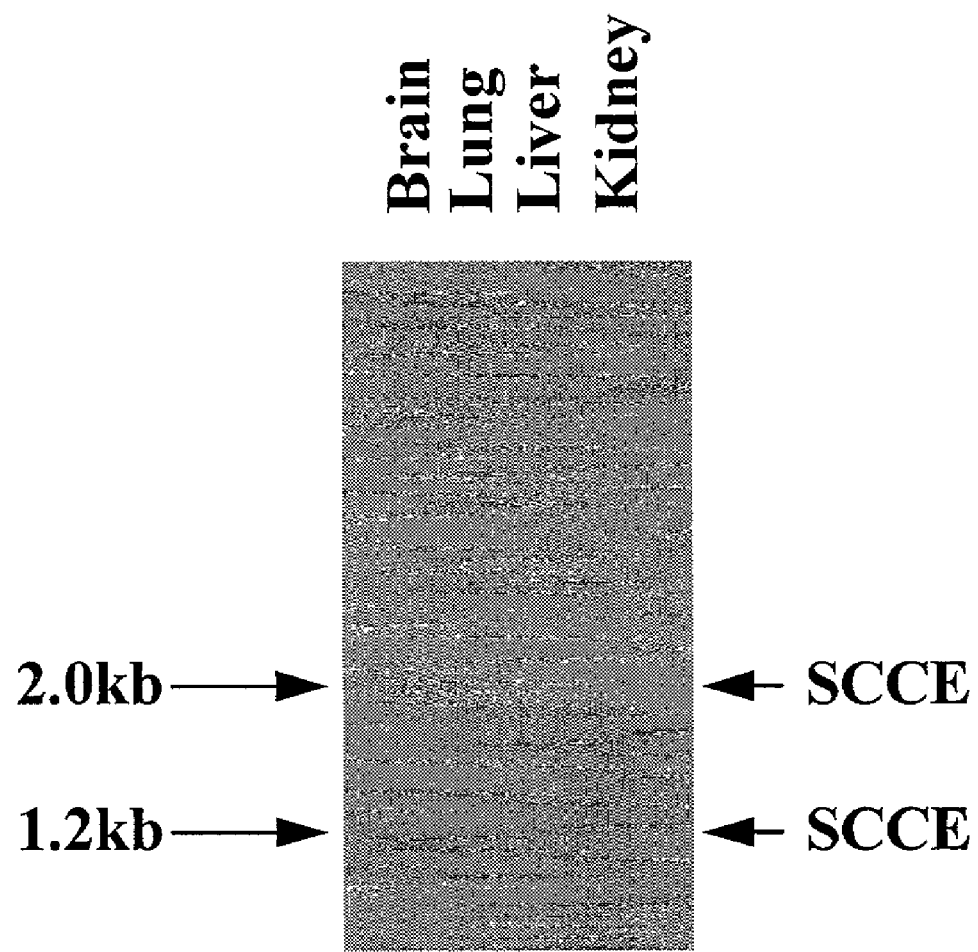
FIG. 12A shows northern blot analysis of mRNA expression of the SCCE gene in fetal tissue.
Figure 12B:
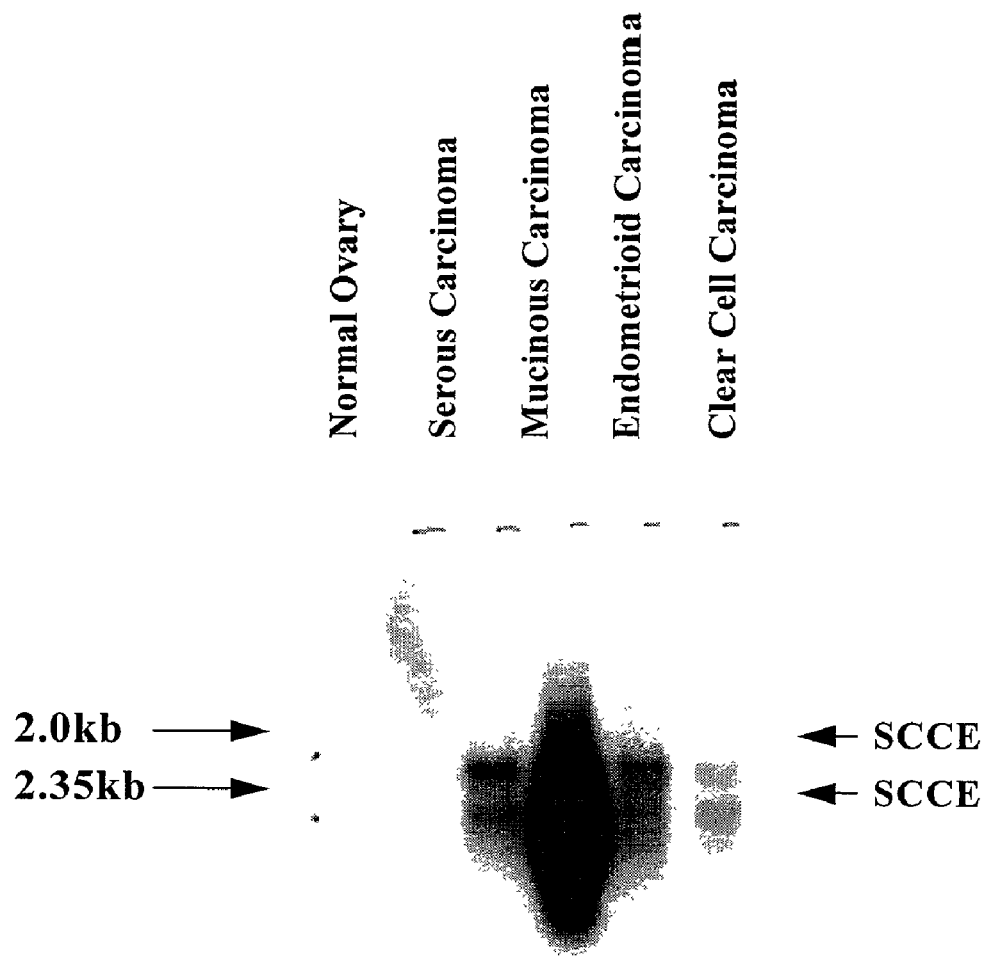
FIG. 12B shows northern blot analysis of mRNA expression of the SCCE gene in ovarian tissue.

Northern blots were probed with the PCR product to determine expression of stratum corneum chymotrypsin enzyme in fetal tissue and ovarian carcinoma (FIGS. 12A & 12B). Noticeably, detection of stratum corneum chymotrypsin enzyme messenger RNA on the fetal Northern was almost non-existent (a problem with the probe or the blot was excluded by performing the proper controls). A faint band appeared in fetal kidney. On the other hand, stratum corneum chymotrypsin enzyme mRNA is abundant in the ovarian carcinoma mRNA (FIG. 12B). Two transcripts of the correct size are observed for stratum corneum chymotrypsin enzyme. The same panel of cDNA used for hepsin analysis was used for stratum corneum chymotrypsin enzyme expression.

No stratum corneum chymotrypsin enzyme expression was detected in the normal ovary lane of the Northern blot. A comparison of all candidate genes, including a loading marker (β-tubulin), was shown to confirm that this observation was not a result of a loading bias. Quantitative PCR using stratum corneum chymotrypsin enzyme primers, along with β-tubulin internal control primers, confirmed the overexpression of stratum corneum chymotrypsin enzyme mRNA in carcinoma of the ovary with no expression in normal ovarian tissue (FIG. 13).

Figure 13A:
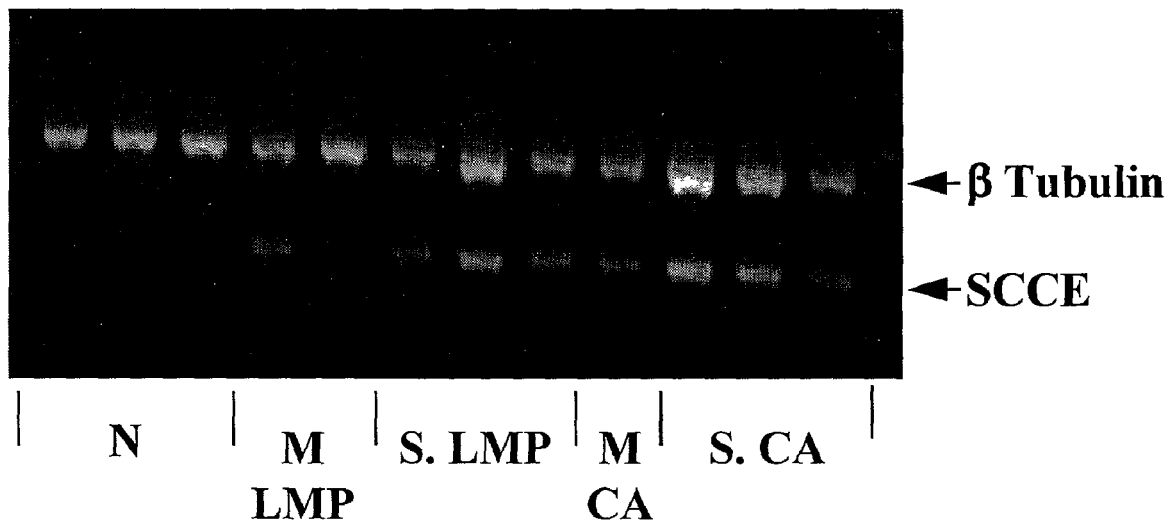
FIG. 13A shows a comparison of quantitative PCR of SCCE cDNA from normal ovary and ovarian carcinomas.
Figure 13B:
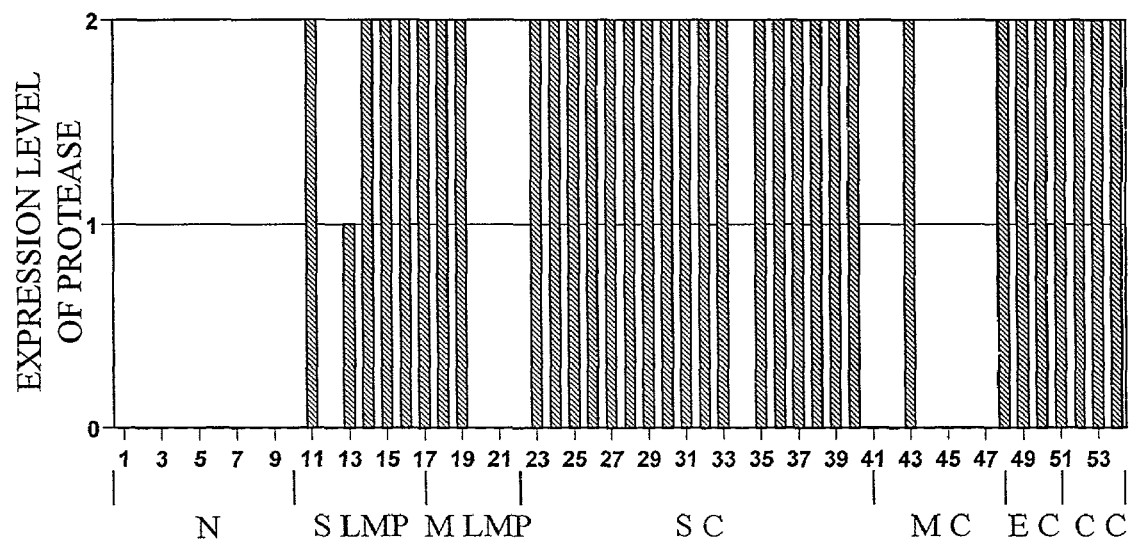
FIG. 13B shows a bar graph comparing the ratio of SCCE to β-tubulin in 10 normal and 44 ovarian carcinoma tissues.

FIG. 13A shows a comparison using quantitative PCR of stratum corneum chymotrypsin enzyme cDNA from normal ovary and ovarian carcinomas. FIG. 13B shows the ratio of stratum corneum chymotrypsin enzyme to the β-tubulin internal standard in 10 normal and 44 ovarian carcinoma tissues. Again, it is observed that stratum corneum chymotrypsin enzyme is highly overexpressed in ovarian carcinoma cells. It is also noted that some mucinous tumors overexpress stratum corneum chymotrypsin enzyme, but the majority do not.

Protease M

Figure 14:
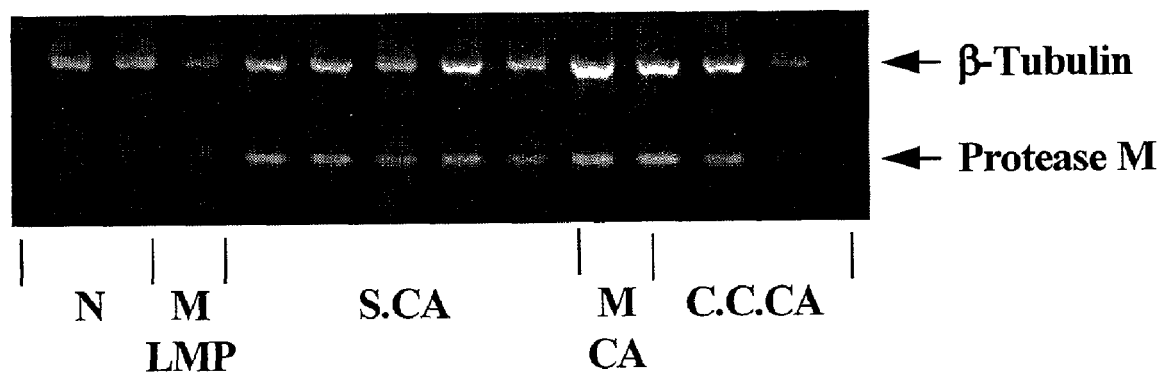
FIG. 14 shows a comparison by quantitative PCR of normal and ovarian carcinoma expression of mRNA for protease M.

Protease M was identified from subclones of the His-ser primer pair. This protease was first cloned by Anisowicz, et al., [Molecular Medicine, 2, 624-636 (1996)] and shown to be overexpressed in carcinomas. A preliminary evaluation indicates that this enzyme is overexpressed in ovarian carcinoma (FIG. 14).

Cofactor I and Complement Factor B

Several serine proteases associated with the coagulation pathway were also subcloned. Examination of normal and ovarian carcinomas by quantitative PCR for expression of these enzymes, it was noticeable that this mRNA was not clearly overexpressed in ovarian carcinomas when compared to normal ovarian tissue. It should be noted that the same panel of tumors was used for the evaluation of each candidate protease.

TADG-12

TADG-12 was identified from the primer pairs, sense-His/antisense-Asp (see FIG. 1, Lanes 1 & 2). Upon subcloning both PCR products in lane 2, the 200 bp product had a unique protease-like sequence not included in GenBank. This 200 bp product contains many of the conserved amino acids common for the His-Asp domain of the family of serine proteins. The second and larger PCR product (300 bp) was shown to have a high degree of homology with TADG-12 (His-Asp sequence), but also contained approximately 100 bp of unique sequence. Synthesis of specific primers and the sequencing of the subsequent PCR products from three different tumors demonstrated that the larger PCR product (present in about 50% of ovarian carcinomas) includes an insert of about 100 bp near the 5' end (and near the histidine) of the sequence. This insert may be a retained genomic intron because of the appropriate position of splice sites and the fact that the insert does not contain an open reading frame (see FIG. 15). This suggests the possibility of a splice site mutation which gives rise to retention of the intron, or a translocation of a sequence into the TADG-12 gene in as many as half of all ovarian carcinomas.

TADG-13 and TADG-14

Figure 16A:
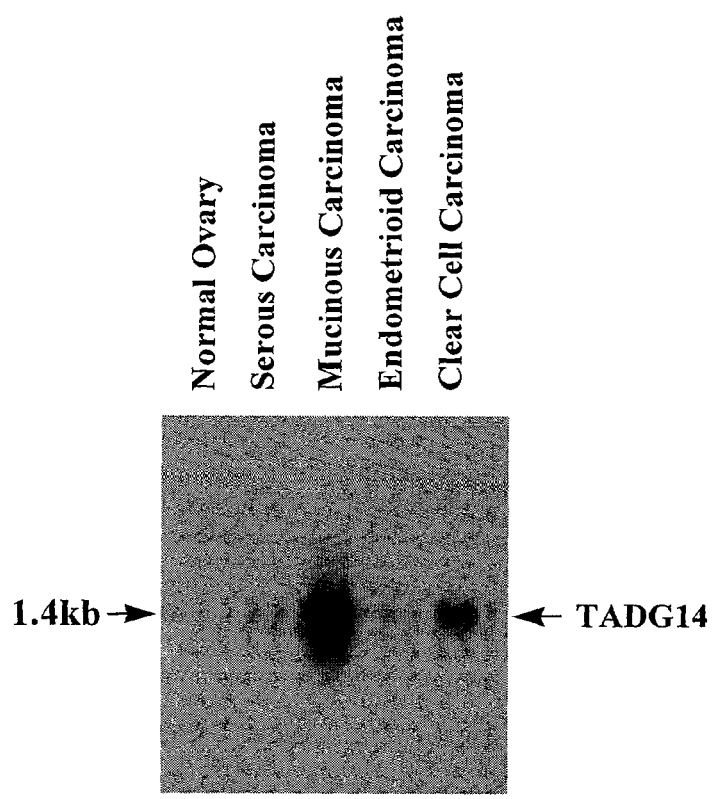
FIG. 16A shows northern blot analysis comparing TADG-14 expression in normal and ovarian carcinoma tissues.
Figure 16B:
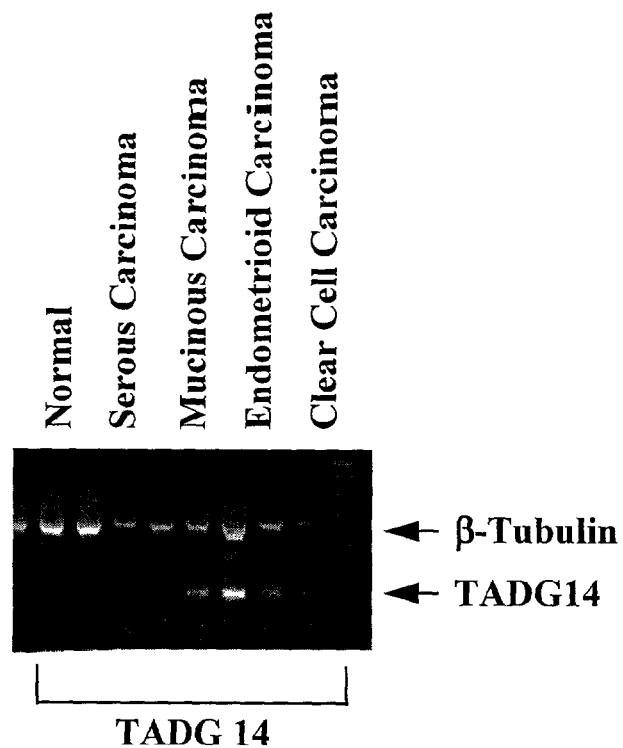
FIG. 16B shows preliminary quantitative PCR amplification of normal and carcinoma cDNAs using specific primers for TADG-14.

Specific primers were synthesized for TADG-13 and TADG-14 to evaluate expression of genes in normal and ovarian carcinoma tissue. Northern blot analysis of ovarian tissues indicates the transcript for the TADG-14 gene is approximately 1.4 kb and is expressed in ovarian carcinoma tissues (FIG. 16A) with no noticeable transcript presence in normal tissue. In quantitative PCR studies using specific primers, increased expression of TADG-14 in ovarian carcinoma tissues was noted compared to a normal ovary (FIG. 16B). The presence of a specific PCR product for TADG-14 in both an HeLa library and an ovarian carcinoma library was also confirmed. Several candidate sequences corresponding to TADG-14 have been screened and isolated from the HeLa library.

Clearly from sequence homology, these genes fit into the family of serine proteases. TADG-13 and -14 are, however, heretofore undocumented genes which the specific primers of the invention allow to be evaluated in normal and tumor cells, and with which the presence or absence of expression of these genes is useful in the diagnosis or treatment selection for specific tumor types.

PUMP-1

In a similar strategy using redundant primers to metal binding domains and conserved histidine domains, a differentially expressed PCR product identical to matrix metalloprotease 7 (MMP-7) was identified, herein called PUMP-1. Using specific primers for PUMP-1, PCR produced a 250 bp product for Northern blot analysis.

Figure 17A:
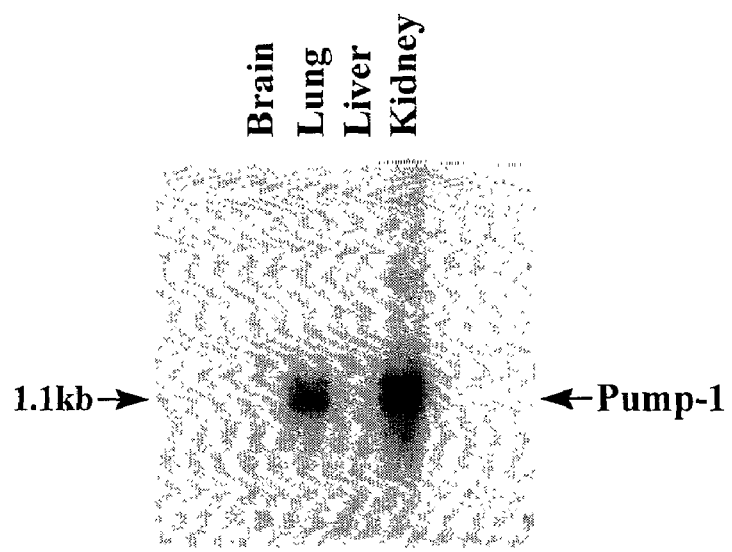
FIG. 17A shows northern blot analysis of the PUMP-1 gene in human fetal tissue.
Figure 17B:
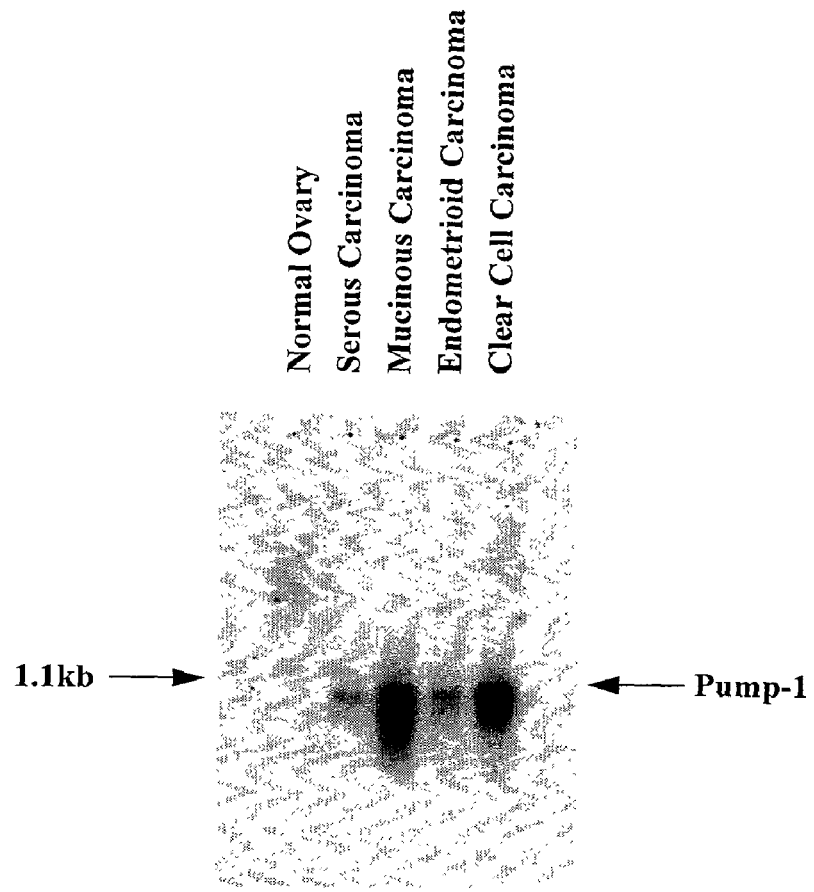
FIG. 17B shows northern blot analysis of the PUMP-1 gene in normal ovary and ovarian carcinomas.
Figure 18A:
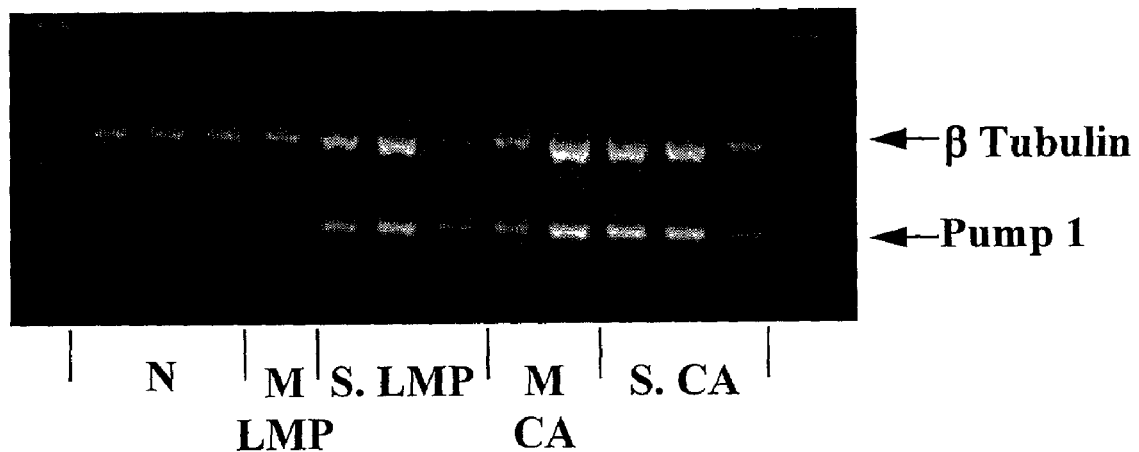
FIG. 18A shows a comparison of PUMP-1 expression in normal and carcinoma tissues using quantitative PCR with an internal β-tubulin control.
Figure 18B:
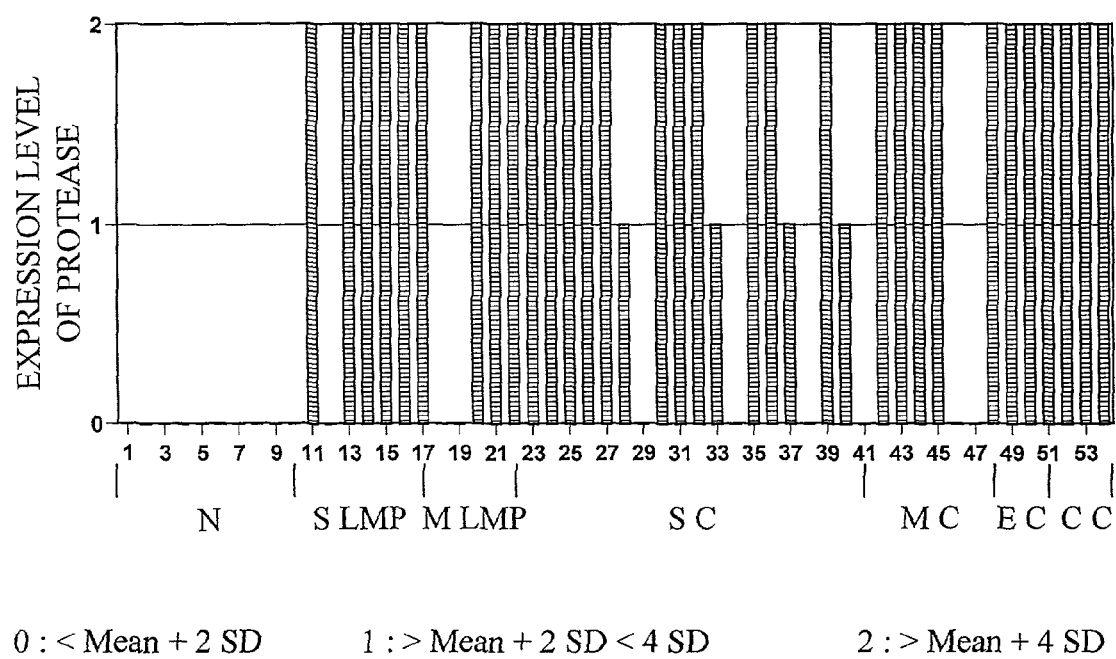
FIG. 18B shows the ratio of mRNA expression of PUMP-1 compared to the internal control β-tubulin in 10 normal and 44 ovarian carcinomas.

PUMP-1 is differentially expressed in fetal lung and kidney tissues. FIG. 17A shows the expression of PUMP-1 in human fetal tissue, while no transcript could be detected in either fetal brain or fetal liver. FIG. 17B compares PUMP-1 expression in normal ovary and carcinoma subtypes using Northern blot analysis. Notably, PUMP-1 is expressed in ovarian carcinoma tissues, and again, the presence of a transcript in normal tissue was not detected. Quantitative PCR comparing normal versus ovarian carcinoma expression of the PUMP-1 mRNA indicates that this gene is highly expressed in serous carcinomas, including most low malignant serous tumors, and is, again, expressed to a lesser extent in mucinous tumors (see FIGS. 18A & 18B). PUMP-1, however, is so far the protease most frequently found overexpressed in mucinous tumors (See Table 7).

Cathepsin-L

Figure 19:
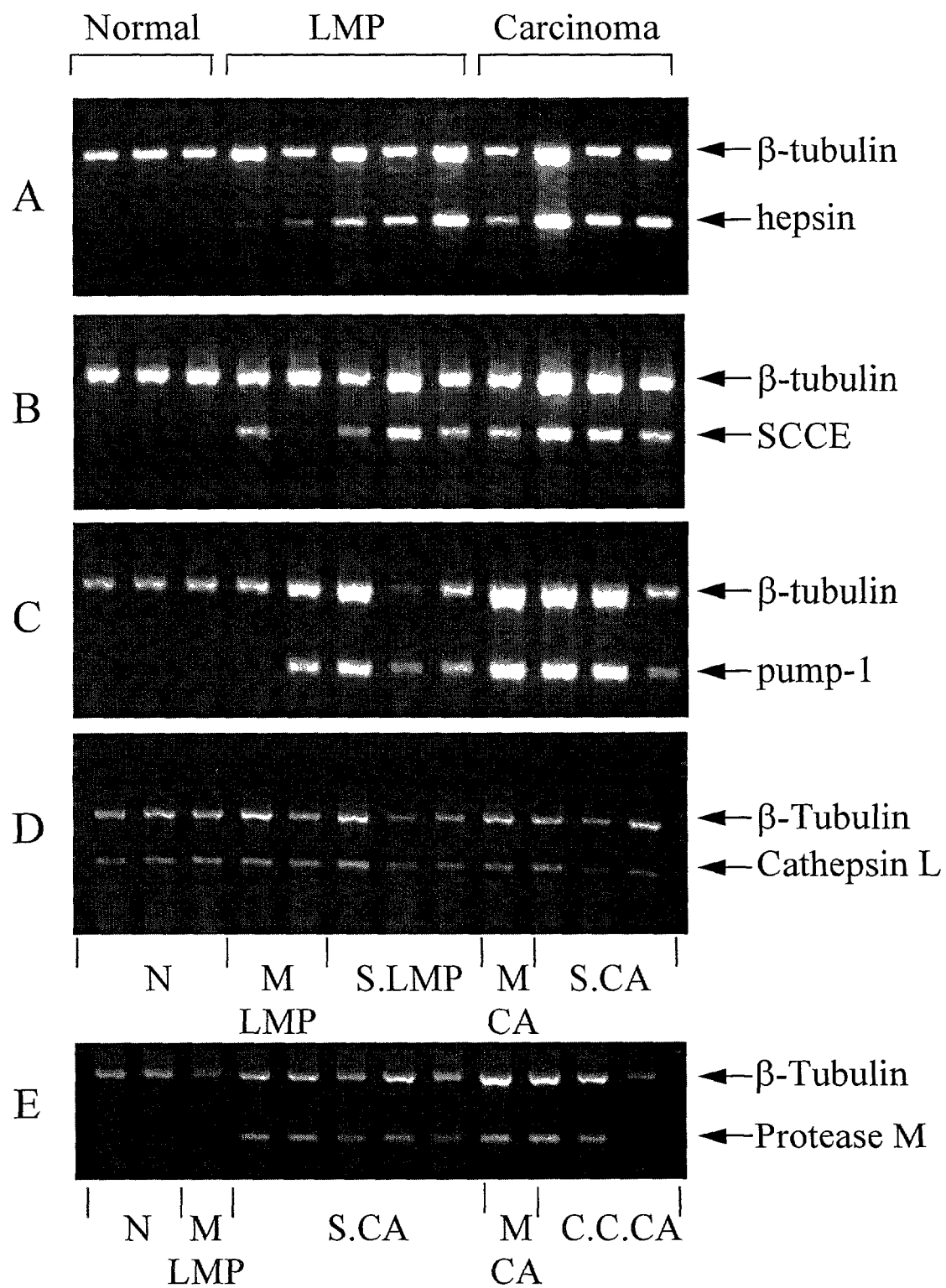
FIG. 19 shows a comparison of PCR amplified products for the hepsin, SCCE, protease M, PUMP-1 and Cathepsin L genes.

Using redundant cysteine protease primers to conserved domains surrounding individual cysteine and histidine residues, the cathepsin-L protease was identified in several serous carcinomas. An initial examination of the expression of cathepsin L in normal and ovarian tumor tissue indicates that transcripts for the cathepsin-L protease are present in both normal and tumor tissues (FIG. 19). However, its presence or absence in combination with other proteases of the present invention permits identification of specific tumor types and treatment choices.

Discussion

Redundant primers to conserved domains of serine, metallo-, and cysteine proteases have yielded a set of genes whose mRNAs are overexpressed in ovarian carcinoma. The genes which are clearly overexpressed include the serine proteases hepsin, stratum corneum chymotrypsin enzyme, protease M TADG12, TADG14 and the metallo-protease PUMP-1 (see FIG. 19 and Table 7). Northern blot analysis of normal and ovarian carcinoma tissues, summarized in FIG. 14, indicated overexpression of hepsin, stratum corneum chymotrypsin enzyme, PUMP-1 and TADG-14. A β-tubulin probe to control for loading levels was included.

TABLE 7

Overexpression of Proteases in Ovarian Tumors

| Type | N | Hepsin | SCCE | Pump-1 | Protease M |
|---|---|---|---|---|---|
| Normal | 10 | 0% (0/10) | 0% (0/10) | 0% (0/10) | 0% (0/10) |
| LMP | 12 | 58.3% (7/12) | 66.7% (8/12) | 75.0% (9/12) | 75% (9/12) |
| serous | 7 | 85.7% (6/7) | 85.7% (6/7) | 85.7% (6/7) | 100% (7/7) |
| mucinous | 5 | 20.0% (1/5) | 40.0% (2/5) | 60% (3/5) | 40.0% (2/5) |
| Carcinoma | 32 | 84.4% (27/32) | 78.1% (25/32) | 81.3% (26/32) | 90.6% (29/32) |
| serous | 19 | 94.7% (18/19) | 89.5% (17/19) | 78.9% (15/19) | 94.7% (18/19) |
| mucinous | 7 | 42.9% (3/7) | 28.6% (2/7) | 71.4% (5/7) | 85.7% (6/7) |
| endometr. | 3 | 100% (3/3) | 100% (3/3) | 100% (3/3) | 100% (3/3) |
| clear cell | 3 | 100% (3/3) | 100% (3/3) | 100% (3/3) | 67.7% (2/3) |

For the most part, these proteins previously have not been associated with the extracellular matrix of ovarian carcinoma cells. No panel of proteases which might contribute to the growth, shedding, invasion and colony development of metastatic carcinoma has been previously described, including the three new candidate serine proteases which are herein disclosed. The establishment of an extracellular protease panel associated with either malignant growth or malignant potential offers the opportunity for the identification of diagnostic or prognostic markers and for therapeutic intervention through inhibition or down regulation of these proteases.

The availability of the instant gene-specific primers coding for the appropriate region of tumor specific proteases allows for the amplification of a specific cDNA probe using Northern and Southern analysis, and their use as markers to detect the presence of the cancer in tissue. The probes also allow more extensive evaluation of the expression of the gene in normal ovary versus low malignant potential tumor, as well as both high- and low-stage carcinomas. The evaluation of a panel of fresh frozen tissue from all the carcinoma subtypes (Table 4) allowed the determination of whether a protease is expressed predominantly in early stage disease or within specific carcinoma subtypes. It was also determined whether each gene's expression is confined to a particular stage in tumor progression and/or is associated with metastatic lesions. Detection of specific combinations of proteases is an identifying characteristic of the specific tumor types and yields valuable information for diagnoses and treatment selection. Particular tumor types may be more accurately diagnosed by the characteristic expression pattern of each specific tumor.

Example 10

Hepsin Peptide Ranking

For vaccine or immune stimulation, individual 9-mers to 11-mers of the hepsin protein were examined to rank the binding of individual peptides to the top 8 haplotypes in the general population (Parker et al., (1994)). The computer program used for this analyses can be found on the web site of National Institutes of Health. Table 8 shows the peptide ranking based upon the predicted half-life of each peptide's binding to a particular HLA allele. A larger half-life indicates a stronger association with that peptide and the particular HLA molecule. The hepsin peptides that strongly bind to an HLA allele are putative immunogens, and are used to innoculate an individual against hepsin.

TABLE 8

Hepsin peptide ranking

| HLA Type & Ranking | Start | Peptide | Predicted Dissociation$_{1/2}$ | SEQ ID No. |
|---|---|---|---|---|
| HLA A0201 | | | | |
| 1 | 170 | SLGRWPWQV | 521.640 | 28 |
| 2 | 191 | SLLSGDWVL | 243.051 | 29 |
| 3 | 229 | GLQLGVQAV | 159.970 | 30 |
| 4 | 392 | KVSDFREWI | 134.154 | 31 |
| 5 | 308 | VLQEARVPI | 72.717 | 32 |
| 6 | 130 | RLLEVISVC | 71.069 | 33 |
| 7 | 98 | ALTHSELDV | 69.552 | 34 |
| 8 | 211 | VLSRWRVFA | 46.451 | 35 |
| 9 | 26 | LLLLTAIGA | 31.249 | 36 |
| 10 | 284 | ALVDGKICT | 30.553 | 37 |
| 11 | 145 | FLAAICQDC | 22.853 | 38 |
| 12 | 192 | LLSGDWVLT | 21.536 | 39 |
| 13 | 20 | ALTAGTLLL | 21.362 | 40 |
| 14 | 259 | ALVHLSSPL | 21.362 | 41 |
| 15 | 277 | CLPAAGQAL | 21.362 | 42 |
| 16 | 230 | LQLGVQAVV | 18.186 | 43 |
| 17 | 268 | PLTEYIQPV | 14.429 | 44 |
| 18 | 31 | AIGAASWAI | 10.759 | 45 |
| 19 | 285 | LVDGKICTV | 9.518 | 46 |
| 20 | 27 | LLLTAIGAA | 9.343 | 47 |
| HLA A0205 | | | | |
| 1 | 191 | SLLSGDWVL | 25.200 | 48 |
| 2 | 163 | IVGGRDTSL | 23.800 | 49 |
| 3 | 392 | KVSDFREWI | 18.000 | 50 |
| 4 | 64 | MVFDKTEGT | 15.300 | 51 |
| 5 | 236 | AVVYHGGYL | 14.000 | 52 |
| 6 | 55 | QVSSADARL | 14.000 | 53 |
| 7 | 130 | RLLEVISVC | 9.000 | 54 |
| 8 | 230 | LQLGVQAVV | 8.160 | 55 |
| 9 | 20 | ALTAGTLLL | 7.000 | 56 |
| 10 | 259 | ALVHLSSPL | 7.000 | 57 |
| 11 | 277 | CLPAAGQAL | 7.000 | 58 |
| 12 | 17 | KVAALTAGT | 6.000 | 59 |
| 13 | 285 | LVDGKICTV | 5.440 | 60 |
| 14 | 308 | VLQEARVPI | 5.100 | 61 |
| 15 | 27 | LLLTAIGAA | 5.100 | 62 |
| 16 | 229 | GLQLGVQAV | 4.000 | 63 |
| 17 | 313 | RVPIISNDV | 4.000 | 64 |
| 18 | 88 | LSCEEMGFL | 3.570 | 65 |

TABLE 8-continued

Hepsin peptide ranking

| HLA Type & Ranking | Start | Peptide | Predicted Dissociation$_{1/2}$ | SEQ ID No. |
|---|---|---|---|---|
| 19 | 192 | LLSGDWVLT | 3.400 | 66 |
| 20 | 284 | ALVDGKICT | 3.000 | 67 |
| HLA A1 | | | | |
| 1 | 89 | SCEEMGFLR | 45.000 | 68 |
| 2 | 58 | SADARLMVF | 25.000 | 69 |
| 3 | 393 | VSDFREWIF | 7.500 | 70 |
| 4 | 407 | HSEASGMVT | 6.750 | 71 |
| 5 | 137 | VCDCPRGRF | 5.000 | 72 |
| 6 | 269 | LTEYIQPVC | 4.500 | 73 |
| 7 | 47 | DQEPLYPVQ | 2.700 | 74 |
| 8 | 119 | CVDEGRLPH | 2.500 | 75 |
| 9 | 68 | KTEGTWRLL | 2.250 | 76 |
| 10 | 101 | HSELDVRTA | 1.350 | 77 |
| 11 | 250 | NSEENSNDI | 1.350 | 78 |
| 12 | 293 | VTGWGNTQY | 1.250 | 79 |
| 13 | 231 | QLGVQAVVY | 1.000 | 80 |
| 14 | 103 | ELDVRTAGA | 1.000 | 81 |
| 15 | 378 | GTGCALAQK | 1.000 | 82 |
| 16 | 358 | VCEDSISRT | 0.900 | 83 |
| 17 | 264 | SSPLPLTEY | 0.750 | 84 |
| 18 | 87 | GLSCEEMGF | 0.500 | 85 |
| 19 | 272 | YIQPVCLPA | 0.500 | 86 |
| 20 | 345 | GIDACQGDS | 0.500 | 87 |
| HLA A24 | | | | |
| 1 | 301 | YYCQQAGVL | 200.000 | 88 |
| 2 | 238 | VYHGGYLPF | 100.000 | 89 |
| 3 | 204 | CFPERNRVL | 36.000 | 90 |
| 4 | 117 | FFCVDEGRL | 20.000 | 91 |
| 5 | 124 | RLPHTQRLL | 12.000 | 92 |
| 6 | 80 | RSNARVAGL | 12.000 | 93 |
| 7 | 68 | KTEGTWRLL | 12.000 | 94 |
| 8 | 340 | GYPEGGIDA | 9.000 | 95 |
| 9 | 242 | GYLPFRDPN | 9.000 | 96 |
| 10 | 51 | LYPVQVSSA | 7.500 | 97 |
| 11 | 259 | ALVHLSSPL | 7.200 | 98 |
| 12 | 277 | CLPAAGQAL | 7.200 | 99 |
| 13 | 191 | SLLSGDWVL | 6.000 | 100 |
| 14 | 210 | RVLSRWRVF | 6.000 | 101 |
| 15 | 222 | VAQASPHGL | 6.000 | 102 |
| 16 | 236 | AVVYHGGYL | 6.000 | 103 |
| 17 | 19 | AALTAGTLL | 6.000 | 104 |
| 18 | 36 | SWAJVAVLL | 5.600 | 105 |
| 19 | 35 | ASWAIVAVL | 5.600 | 106 |
| 20 | 300 | QYYGQQAGV | 5.600 | 107 |
| HLA B7 | | | | |
| 1 | 363 | ISRTPRWRL | 90.000 | 108 |
| 2 | 366 | TPRWRLCGI | 80.000 | 109 |
| 3 | 236 | AVVYHGGYL | 60.000 | 110 |
| 4 | 13 | CSRPKVAAL | 40.000 | 111 |
| 5 | 179 | SLRYDGAHL | 40.000 | 112 |
| 6 | 43 | LLRSDQEPL | 40.000 | 113 |
| 7 | 19 | AALTAGTLL | 36.000 | 114 |
| 8 | 55 | QVSSADARL | 20.000 | 115 |
| 9 | 163 | IVGGRDTSL | 20.000 | 116 |
| 10 | 140 | CPRGRFLAA | 20.000 | 117 |
| 11 | 20 | ALTAGTLLL | 12.000 | 118 |
| 12 | 409 | EASGMVTQL | 12.000 | 119 |
| 13 | 259 | ALVHLSSPL | 12.000 | 120 |
| 14 | 35 | ASWAIVAVL | 12.000 | 121 |
| 15 | 184 | GAHLCGGSL | 12.000 | 122 |
| 16 | 18 | VAALTAGTL | 12.000 | 123 |
| 17 | 222 | VAQASPHGL | 12.000 | 124 |
| 18 | 224 | QASPHGLQL | 12.000 | 125 |
| 19 | 265 | SPLPLTEYI | 8.000 | 126 |
| 20 | 355 | GPFVCEDSI | 8.00 | 127 |
| HLA B8 | | | | |
| 1 | 13 | CSRPKVAAL | 80.000 | 128 |
| 2 | 366 | TPRWRLCGI | 80.000 | 129 |
| 3 | 140 | CPRGRFLAA | 16.000 | 130 |
| 4 | 152 | DCGRRKLPV | 4.800 | 131 |
| 5 | 363 | ISRTPRWRL | 4.000 | 132 |

TABLE 8-continued

Hepsin peptide ranking

| HLA Type & Ranking | Start | Peptide | Predicted Dissociation$_{1/2}$ | SEQ ID No. |
|---|---|---|---|---|
| 6 | 163 | IVGGRDTSL | 4.000 | 133 |
| 7 | 331 | QIKPKMFCA | 4.000 | 134 |
| 8 | 80 | RSNARVAGL | 2.000 | 135 |
| 9 | 179 | SLRYDGAHL | 1.600 | 136 |
| 10 | 43 | LLRSDQEPL | 1.600 | 137 |
| 11 | 409 | EASGMVTQL | 1.600 | 138 |
| 12 | 311 | EARVPIISN | 0.800 | 139 |
| 13 | 222 | VAQASPHGL | 0.800 | 140 |
| 14 | 19 | AALTAGTLL | 0.800 | 141 |
| 15 | 18 | VAALTAGTL | 0.800 | 142 |
| 16 | 184 | GAHLCGGSL | 0.800 | 143 |
| 17 | 224 | QASPHGLQL | 0.800 | 144 |
| 18 | 82 | NARVAGLSC | 0.800 | 145 |
| 19 | 204 | CFPERNRVL | 0.600 | 146 |
| 20 | 212 | LSRWRVFAG | 0.400 | 147 |
| HLA B2702 | | | | |
| 1 | 172 | GRWPWQVSL | 300.000 | 148 |
| 2 | 44 | LRSDQEPLY | 200.00 | 149 |
| 3 | 155 | RRKLPVDRI | 180.000 | 150 |
| 4 | 213 | SRWRVFAGA | 100.000 | 151 |
| 5 | 166 | GRDTSLGRW | 100.000 | 152 |
| 6 | 369 | WRLCGIVSW | 100.000 | 153 |
| 7 | 180 | LRYDGAHLC | 100.000 | 154 |
| 8 | 96 | LRALTHSEL | 60.000 | 155 |
| 9 | 396 | FREWIFQAI | 60.000 | 156 |
| 10 | 123 | GRLPHTQRL | 60.000 | 157 |
| 11 | 207 | ERNRVLSRW | 30.000 | 158 |
| 12 | 209 | NRVLSRWRV | 20.000 | 159 |
| 13 | 14 | SRPKVAALT | 20.000 | 160 |
| 14 | 106 | VRTAGANGT | 20.000 | 161 |
| 15 | 129 | QRLLEVISV | 20.000 | 162 |
| 16 | 349 | CQGDSGGPF | 20.000 | 163 |
| 17 | 61 | ARLMVFDKT | 20.000 | 164 |
| 18 | 215 | WRVFAGAVA | 20.000 | 165 |
| 19 | 143 | GRFLAAICQ | 10.000 | 166 |
| 20 | 246 | FRDPNSEEN | 10.000 | 167 |
| HLA B4403 | | | | |
| 1 | 132 | LEVISVCDC | 36.000 | 168 |
| 2 | 91 | EEMGFLRAL | 18.000 | 169 |
| 3 | 264 | SSPLPLTEY | 13.500 | 170 |
| 4 | 310 | QEARVPIIS | 12.000 | 171 |
| 5 | 319 | NDVCNGADF | 10.000 | 172 |
| 6 | 4 | KEGGRTVPC | 9.000 | 173 |
| 7 | 251 | SEENSNDIA | 8.000 | 174 |
| 8 | 256 | NDIALVHLS | 7.500 | 175 |
| 9 | 294 | TGWGNTQYY | 6.750 | 176 |
| 10 | 361 | DSISRTPRW | 6.750 | 177 |
| 11 | 235 | QAVVYHCGY | 6.000 | 178 |
| 12 | 109 | AGANGTSGF | 6.000 | 179 |
| 13 | 270 | TEYIQPVCL | 6.000 | 180 |
| 14 | 174 | WPWQVSLRY | 4.500 | 181 |
| 15 | 293 | VTGWGNTQY | 4.500 | 182 |
| 16 | 69 | TBGTWRLLC | 4.000 | 183 |
| 17 | 90 | CEEMGFLRA | 4.000 | 184 |
| 18 | 252 | EENSNDIAL | 4.000 | 185 |
| 19 | 48 | QEPLYPVQV | 4.000 | 186 |
| 20 | 102 | SELDVRTAG | 3.600 | 187 |

Example 11

Hepsin Peptides as Target Epitopes for Human CD8$^+$ Cytotoxic T Cells

Two computer programs were used to identify 9-mer peptides containing binding motifs for HLA class I molecules. The first, based on a scheme devised by Parker et al (1994), was developed by the Bioinformatics and Molecular Analysis Section (BIMAS) of the Center for Information Technology, NIH, and the second, known as SYFPEITHI, was formulated by Rammensee and colleagues at the University of Tubingen, Germany.

Peptides that possessed HLA A2.1 binding motifs were synthesized and tested directly for their ability to bind HLA A2.1. This technique employs T2 cells which are peptide transporter-deficient and thus express low endogenous HLA class I levels due to inability to load peptide and stabilize HLA class I folding for surface expression. It has been showed that addition of exogenous peptides capable of binding HLA A2.1 (A*0201) could increase the number of properly folded HLA A2.1 molecules on the cell surface, as revealed by flow cytometry (Nijman et al, 1993).

Peptides that possessed binding motifs for HLA class I molecules other than A2.1 were tested directly for their ability to induce specific CD8$^+$ CTL responses from normal adult donors as described below.

Monocyte-derived DC were generated from peripheral blood drawn from normal adult donors of the appropriate HLA type. Adherent monocytes were cultured in AIM-V (Gibco-BRL) supplemented with GM-CSF and IL-4 according to standard techniques (Santin et al, 2000, 2001). After 5-6 days, DC maturation was induced by addition of PGE$_2$, IL-1β and TNFα for a further 48 h.

Mature DC were loaded with peptide (2×10$^6$ DC with 50 µg/ml peptide in 1 ml serum-free AIM-V medium for 2 h at 37° C.) and washed once prior to culture with 1×10$^6$/ml peripheral blood mononuclear cells (PBMC) in AIM-V or AIM-V plus 5% human AB serum. The PBMC:DC ratio was between 20:1 and 30:1. After 7 days, responder T cells were restimulated with peptide-loaded, irradiated autologous DC or PBMC at responder:stimulator ratios between 10:1 and 20:1 or 1:1 and 1:10 respectively. At this point, cultures were supplemented with recombinant human IL-2 (10-100 U/ml), and fed with 50-75% changes of fresh medium plus IL-2 every 2-4 days. T cell lines were established and maintained by peptide restimulation every 14-21 days. Responder CD8$^+$ T cells were purified by positive selection with anti-CD8-coupled magnetic beads (Dynal, Inc.) after the 2$^{nd}$ or 3$^{rd}$ antigen stimulation.

Peptide-specific cytotoxicity was tested in standard 5-6 h microwell $^{51}$Cr-release assays (Nazaruk et al, 1998). Autologous EBV-transformed lymphoblastoid cell lines (LCL) were loaded with peptide (50 µg/ml, 1 h at 37° C.) and subsequently $^{51}$Cr-labeled (50 µCi in 200-300 µl, 1 h at 37° C.). Peptide-loaded $^{51}$Cr-labeled LCL were incubated with CD8$^+$ T cells at effector-target ration between 10:1 and 1.25:1. Cytotoxicity was recorded as percentage $^{51}$Cr released into culture supernatants.

Hepsin Peptide 170-178

Figure 20:
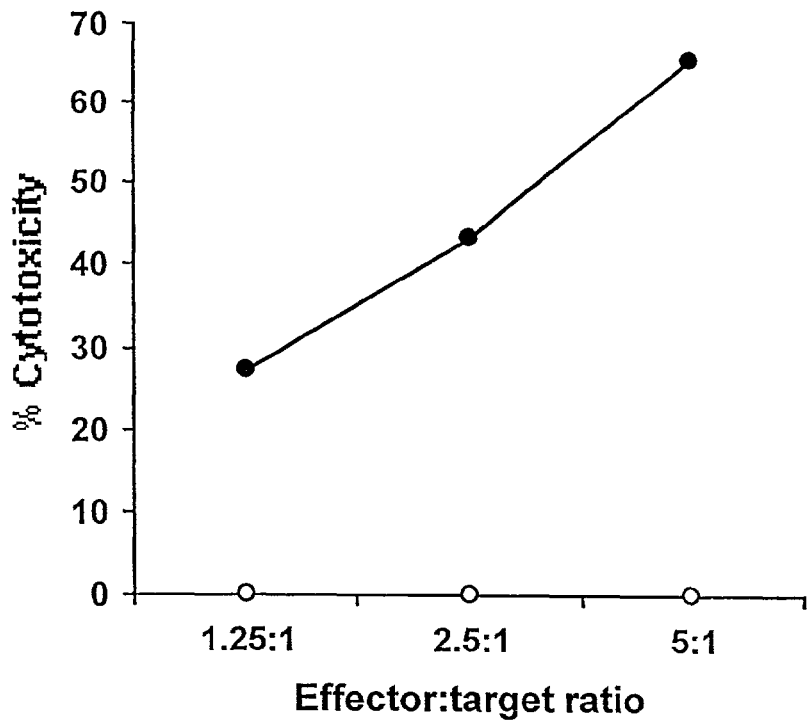
FIG. 20 shows CD8+ CTL recognition of hepsin 170-178 peptide in a 5 hr $^{51}$Cr release assay. Targets were LCL loaded with hepsin 170-178 (closed circles) and control LCL (open circles).

Hepsin peptide 170-178 (SEQ ID No. 28) is an HLA A2.1-binding peptide, as revealed by upregulation of A2.1 expression in T2 cells (data not shown). CD8$^+$ CTL specific for hepsin 170-178 killed peptide-loaded autologous LCL, but did not kill control, peptide-free LCL (FIG. 20). Heterologous HLA A2.1-expressing peptide-loaded LCL were efficiently killed, but targets lacking HLA A2.1 were not killed. Natural killer-sensitive K562 cells were not lysed. Cytotoxicity against hepsin 170-178 loaded LCL could be blocked with MAb specific for a non-polymorphic HLA class I determinant, confirming that lysis was HLA class I-restricted. Cytotoxicity was also blocked by MAb specific for HLA A2.1

Hepsin Peptide 172-180

Figure 21:
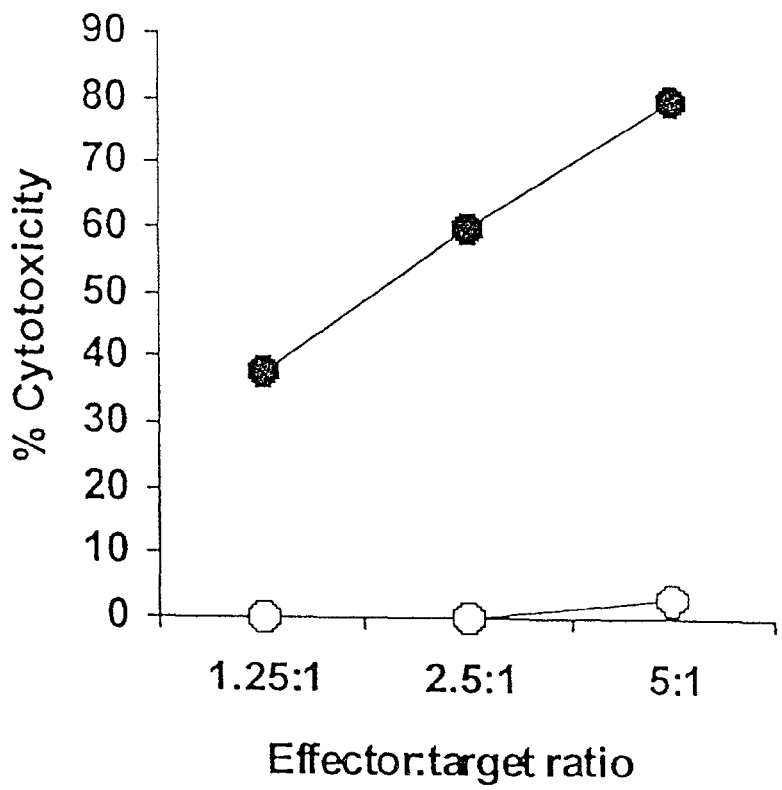
FIG. 21 shows CD8+ CTL recognition of hepsin 172-180 peptide in a 5 hr $^{51}$Cr release assay. Targets were LCL loaded with hepsin 172-180 (closed circles) and control LCL (open circles).

Hepsin peptide 172-180 (SEQ ID No. 148) was predicted by computer analysis to bind HLA B27. While this could not be demonstrated directly, cytotoxicity assays showed that CD8$^+$ CTL specific for hepsin 172-180 could kill peptide-loaded, HLA B27-expressing autologous and heterologous LCL, but failed to recognize heterologous peptide-loaded LCL that did not express HLA B27, or peptide-free control LCL (FIG. 21). Natural killer-sensitive K562 cells were not lysed. Cytotoxicity against hepsin 172-180 loaded LCL could be blocked with MAb specific for a non-polymorphic HLA class I determinant, confirming that lysis was HLA class I-restricted.

Hepsin Peptide 42-51

Figure 22:
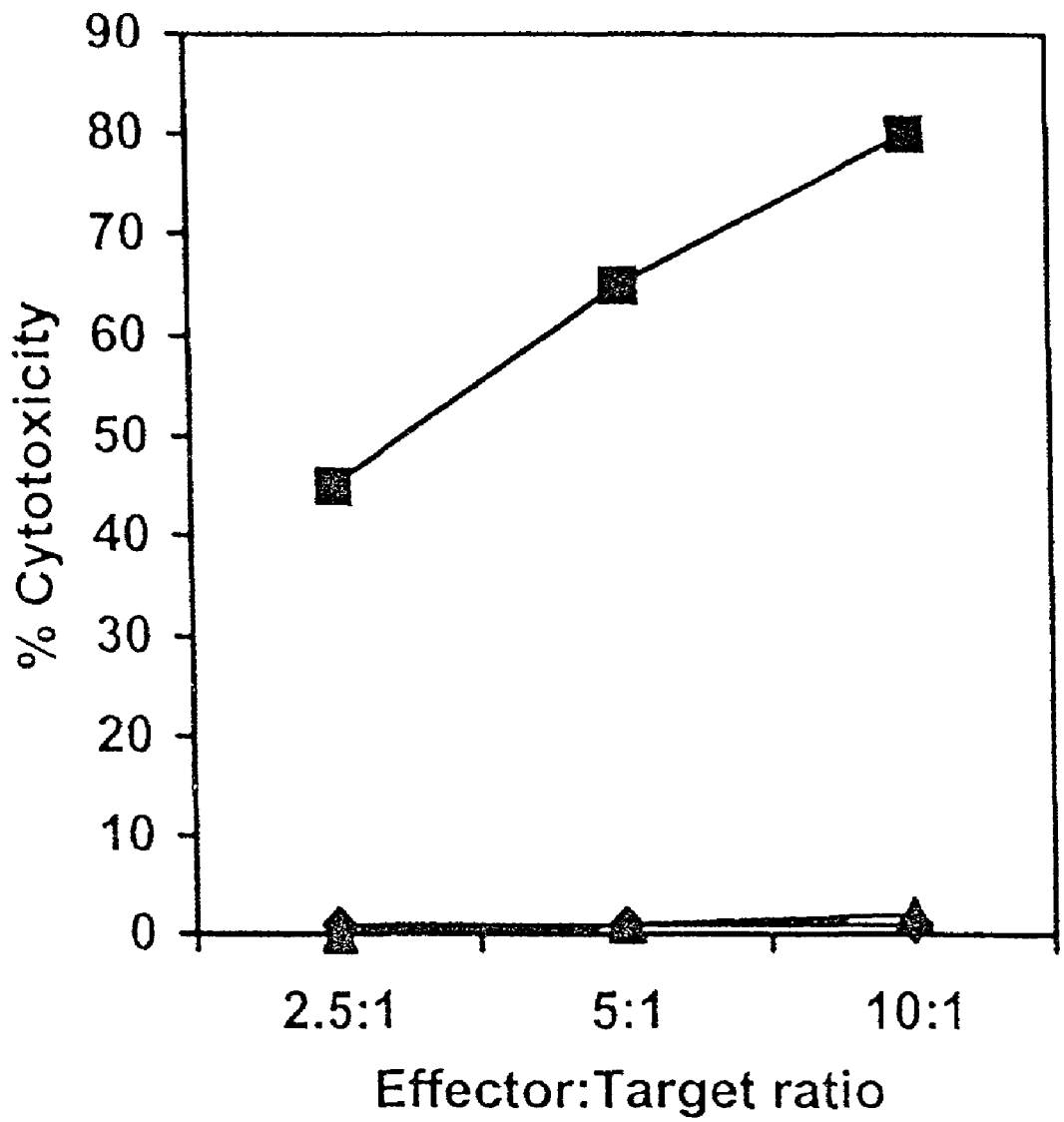
FIG. 22 shows CD8+ CTL recognition of hepsin 42-51 peptide in a 5 hr $^{51}$Cr release assay. Targets were LCL loaded with hepsin 42-51 (squares), control LCL (triangles) and K562 cells (diamonds).

Hepsin peptide 42-51 (SEQ ID No. 189) was predicted by computer analysis to bind HLA A*0201. CD8+ CTL specific for hepsin 42-51 killed peptide-loaded autologous LCL, but did not kill control, peptide-free LCL (FIG. 22). Heterologous HLA A*0201-expressing peptide-loaded LCL were efficiently killed, but targets lacking HLA A*0201 were not killed. Natural killer-sensitive K562 cells were not lysed. Cytotoxicity against hepsin 42-51 loaded LCL could be blocked with MAb specific for a non-polymorphic HLA class I determinant, confirming that lysis was HLA class I-restricted. Cytotoxicity was also blocked by MAb specific for HLA A2.1.

Hepsin Peptide 284-293

Figure 23:
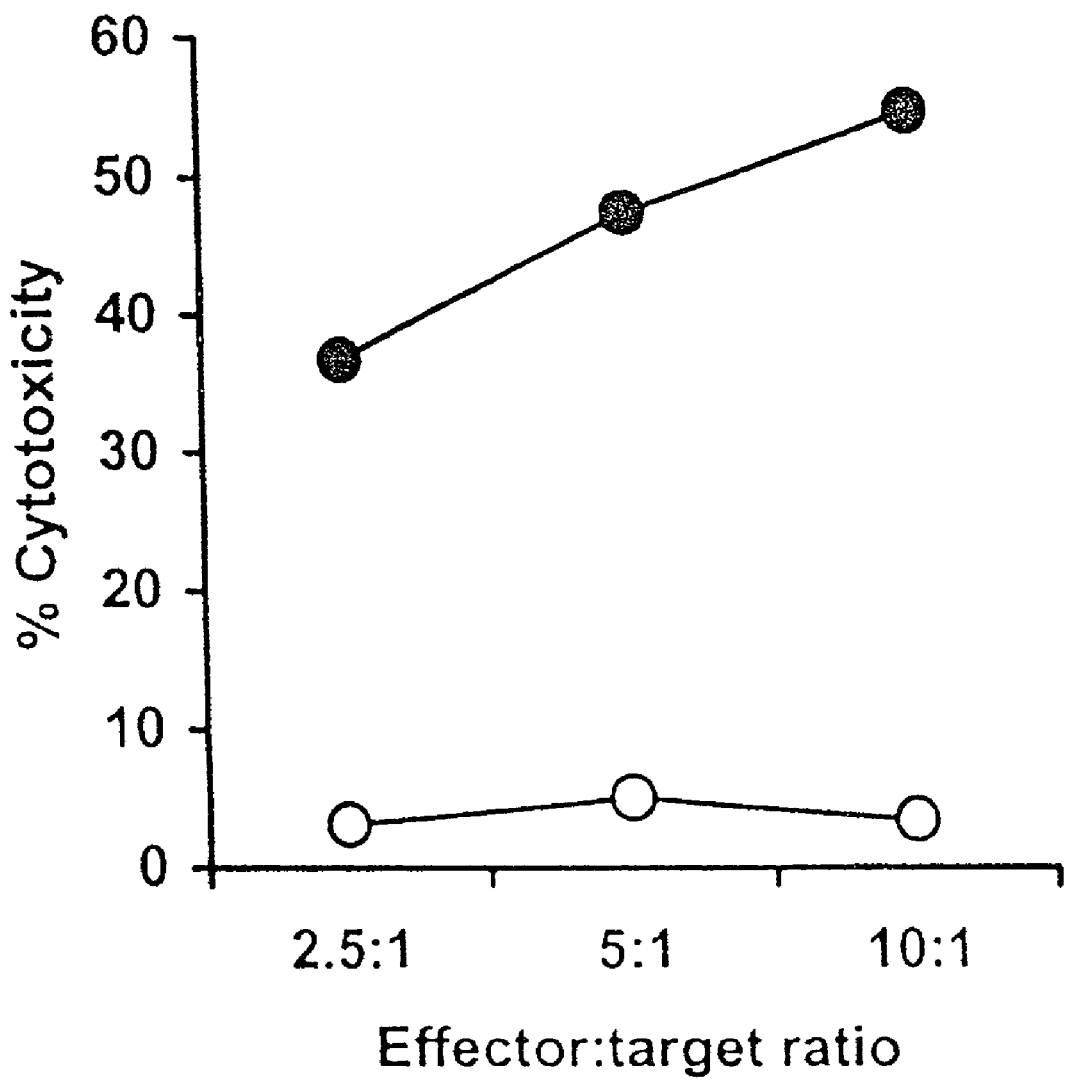
FIG. 23 shows CD8+ CTL recognition of hepsin 284-293 peptide in a 5 hr $^{51}$Cr release assay. Targets were LCL loaded with hepsin 284-293 (closed circles) and control LCL (open circles).

Hepsin peptide 284-293 (SEQ ID No. 190) was predicted by computer analysis to bind HLA A*0201. CD8+ CTL specific for hepsin 284-293 killed peptide-loaded autologous LCL, but did not kill control, peptide-free LCL (FIG. 23). Heterologous HLA A*0201-expressing peptide-loaded LCL were efficiently killed, but targets lacking HLA A*0201 were not killed. Natural killer-sensitive K562 cells were not lysed. Cytotoxicity against hepsin 284-293 loaded LCL could be blocked with MAb specific for a non-polymorphic HLA class I determinant, confirming that lysis was HLA class I-restricted.

Hepsin Peptide 308-317

Figure 24:
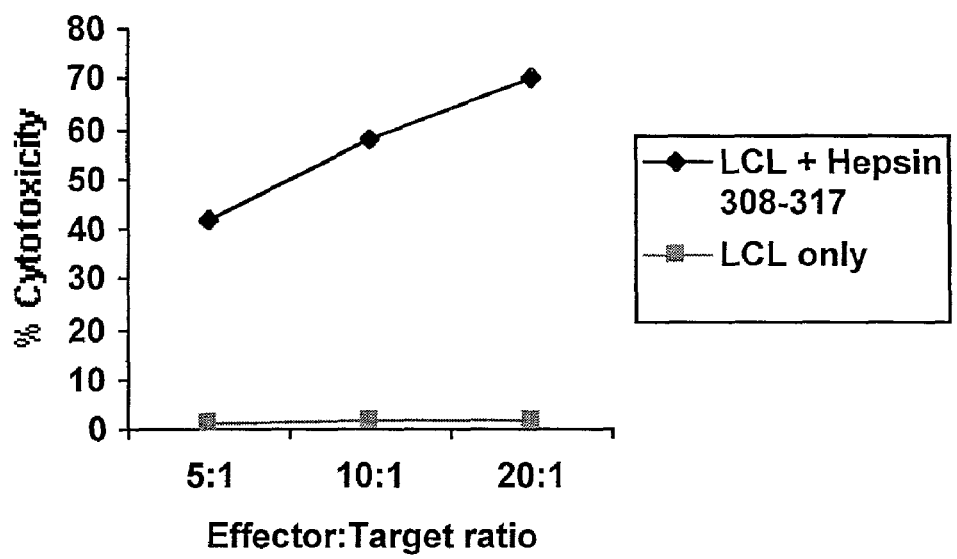
FIG. 24 shows CD8+ CTL recognition of hepsin 308-317 peptide in a 5 hr $^{51}$Cr release assay. Targets cells were LCL loaded with or without hepsin 308-317.

Hepsin peptide 308-317 (SEQ ID No. 191) was predicted by computer analysis to bind HLA A*0201. CD8+ CTL specific for hepsin 308-317 killed peptide-loaded autologous LCL, but did not kill control, peptide-free LCL (FIG. 24). Heterologous HLA A*0201-expressing peptide-loaded LCL were efficiently killed, but targets lacking HLA A*0201 were not killed. Cytotoxicity against hepsin 308-317 loaded LCL could be blocked with MAb specific for a non-polymorphic HLA class I determinant, confirming that lysis was HLA class I-restricted.

Example 12

Recombinant Full Length Hepsin Induces CD4+ and CD8+ T Cell Proliferative Responses Results disclosed above that show dendritic cells (DC) loaded with hepsin-derived peptides can efficiently stimulate HLA A2.1-restricted and HLA B27-restricted CD8+ CTL responses in normal adults suggest that hepsin may be a leading candidate as a target for dendritic cell-based immunotherapy of ovarian cancer. Furthermore, the utility of hepsin as a target antigen for immunotherapeutic purposes may not be confined to ovarian cancer. A recent series of gene expression profiling studies identified hepsin as a major tumor marker for prostate cancer. Hepsin was consistently highly expressed in prostate cancer, but not in benign prostatic hyperplasia (1-5). These reports strongly support the proposal that hepsin may also be a leading target for dendritic cell-based immunotherapy of prostate cancer.

However, the use of peptides restricts the response to predetermined HLA class I types, which imposes limitations on patient selection. The use of dendritic cells loaded with full-length recombinant tumor antigens circumvents this problem, and also offers the prospect of being able to induce both CD8+ T cell responses and helper CD4+ T cell responses, the latter of which may play a critical role in the generation and maintenance of effective anti-tumor immunity. A further, potentially critical, advantage of using full-length tumor antigen is that CD8+ T cell responses are induced against naturally processed epitopes, which markedly increases the likelihood that CD8+ T cells will recognize endogenously synthesized antigens that are also naturally processed and presented by the target ovarian tumor cell.

The following example shows that dendritic cells loaded with full-length recombinant hepsin are capable of inducing both CD4+ T cell and CD8+ T cell proliferative responses to hepsin.

Hepsin cDNA was cloned into the IPTG-inducible pQE-30 vector (Qiagen) and expressed in *E. coli*. Addition of a 6×-histidine tag on the amino terminus facilitates affinity purification with Ni-NTA resin. Dendritic cells were derived from peripheral blood monocyte precursors as described above. Mature dendritic cells express high levels of HLA class I and class II molecules, costimulatory molecules (e.g., CD86 and CD40), and CD83 (expressed on mature, but not immature, monocyte-derived dendritic cells), but do not express CD14 (a macrophage/monocyte marker).

To stimulate hepsin-specific T cell proliferation, mature dendritic cells were loaded with purified recombinant hepsin by DOTAP lipofection. Briefly 25 µg hepsin was combined with 15 µg DOTAP (Roche Applied Science, Indianapolis, Ind.) in 500 µl AIM-V medium (Invitrogen, Grand Island, N.Y.). This mixture was incubated with $1-2 \times 10^6$ dendritic cells for up to 2 hours at 37° C. Hepsin-loaded dendritic cells were cocultured with autologous peripheral blood lymphocytes from a normal male donor at a responder:stimulator ratio of 30:1 in AIM-V medium plus 5% human AB serum. After 7-10 days, responder T cells were restimulated with hepsin-loaded dendritic cells at a responder:stimulator ratio of 10:1. T cell cultures were supplemented with recombinant IL-2 (10-100 U/ml), and fed every 2-4 days with 50-75% changes of medium plus IL-2. T cell lines were subsequently maintained by restimulation with hepsin-loaded DC every 14 days. Before the $3^{rd}$ restimulation, CD4+ T cells and CD8+ T cells were purified by positive selection with anti-CD4 or anti-CD8-conjugated magnetic beads, as appropriate. Resultant populations were >98% pure by flow cytometry.

CD4+ T cells and CD8+ T cells were tested in microwell lymphoproliferation assays after the $4^{th}$ and $5^{th}$ passages, respectively. T cells ($2 \times 10^4$/well) were incubated with dendritic cells loaded with hepsin by DOTAP lipofection ($5 \times 10^3$/well) or control dendritic cells treated with DOTAP only ($5 \times 10^3$/well). The assay was incubated for 72 hours. Proliferation was determined by the addition of $^3$H-thymidine (1 µCi/well) to each microwell culture for the final 24 hours. Results are presented as the mean of triplicate microwells, calculated as a stimulation index (ratio of $^3$H-thymidine uptake by T cells cultured with dendritic cells versus $^3$H-thymidine uptake by T cells cultured alone).

Figure 25:
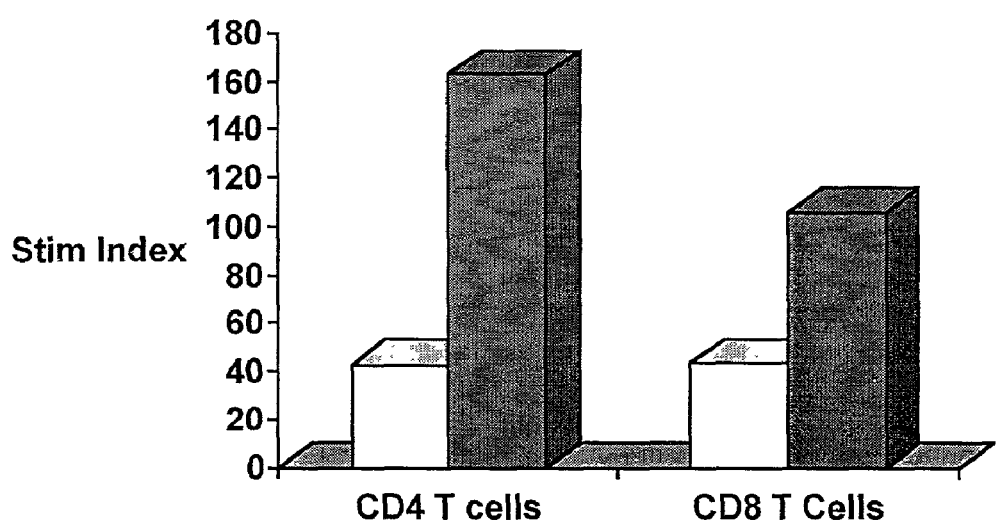
FIG. 25 shows hepsin-specific CD4+ T cell and CD8+ T cell proliferative responses stimulated by full length hepsin protein. Solid histograms represent the stimulation index for T cells stimulated with hepsin-loaded dendritic cells, and open histograms represent the stimulation index for T cells stimulated with control dendritic cells.

Although some background proliferation in response to stimulation with control dendritic cells was seen, this assay clearly shows that hepsin-loaded dendritic cells are capable of inducing a significant antigen-specific lymphoproliferative response by both CD4+ T cells and CD8+ T cells (FIG. 25). These results underline the potential for dendritic cell-based immunotherapy using hepsin as a tumor target antigen.

In summary, the present invention provides immunotherapeutic applications specially targeted at hepsin, and applied to the treatment of tumors that express hepsin. Target diseases will include ovarian cancer and prostate cancer, but will also include any other malignancy for which hepsin expression can be demonstrated. Immunotherapeutic applications will include, but are not limited to: Immunotherapy may take the form of hepsin-loaded dendritic cell vaccination, in which dendritic cells are generated in vitro from peripheral blood drawn from the patient, loaded with hepsin by lipofection or other means, and then given back to the patient as an autologous cellular vaccine, either in single doses or multiple doses. Hepsin may also be expressed in dendritic cells following transduction with a recombinant DNA vector, and such hepsin-transduced dendritic cells may then be used as a cellular vaccine.

Recombinant DNA vectors that express hepsin, either alone or as a fusion protein with other immunologically active components, may be used as a DNA vaccine for treatment of tumors that express hepsin. Hepsin-loaded or hepsin-expressing dendritic cells may also be used to stimulate tumor antigen-specific T cell responses in vitro, followed by adoptive immunotherapy, in which the patient will be given autologous hepsin-specific T cells.

Monoclonal antibody therapy based on hepsin are also apparent. Hepsin is expressed as a transmembrane protein on the surface of tumor cells. Construction of human monoclonal antibodies, or chimeric humanized monoclonal antibodies specific for hepsin offers an attractive option for immunotherapy of hepsin-expressing malignancies.

The following references were cited herein:
1. Luo et al. *Cancer Res.* 61:4683-4688 (2001).
2. Magee et al. *Cancer Res.* 61:5692-5696 (2001).
3. Welsh et al. *Cancer Res.* 61:5974-5978 (2001).
4. Dhanasekaran et al. *Nature* 412:822-826 (2001).
5. Stamey et al. *J. Urol.* 166:2171-2177 (2001).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An in vitro method of producing activated T cells directed toward hepsin, comprising the steps of: isolating dendritic cells expressing Human Leukocyte Antigen B27 (HLA B27) molecule from an individual with ovarian cancer, lung cancer, breast cancer or prostate cancer; transfecting said isolated dendritic cells with an expression vector encoding hepsin protein fragment consisting of SEQ ID No. 148, thereby producing dendritic cells expressing said peptide in association with said HLA B27 molecule; and exposing said peptide expressing dendritic cells to T cells, wherein said dendritic cells present said peptide to the T cells, thereby producing activated T cells directed towards hepsin.

* * * * *